United States Patent
Sweeney et al.

(10) Patent No.: US 12,168,803 B2
(45) Date of Patent: Dec. 17, 2024

(54) COMPOSITIONS AND METHODS FOR SCREENING AND DIAGNOSIS OF PROSTATE CANCER

(71) Applicant: DANA-FARBER CANCER INSTITUTE, INC., Boston, MA (US)

(72) Inventors: Christopher Sweeney, Waban, MA (US); Philip Kantoff, New York, NY (US); Gwo-Shu Mary Lee, Newton, MA (US); Kazumasa Komura, New York, NY (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 645 days.

(21) Appl. No.: 17/350,833

(22) Filed: Jun. 17, 2021

(65) Prior Publication Data

US 2022/0042105 A1 Feb. 10, 2022

Related U.S. Application Data

(62) Division of application No. 16/066,876, filed as application No. PCT/US2016/069383 on Dec. 30, 2016, now Pat. No. 11,066,708.

(60) Provisional application No. 62/273,946, filed on Dec. 31, 2015.

(51) Int. Cl.
| | |
|---|---|
| C12Q 1/68 | (2018.01) |
| A61K 31/337 | (2006.01) |
| A61K 31/4166 | (2006.01) |
| A61P 35/00 | (2006.01) |
| C12N 5/09 | (2010.01) |
| C12Q 1/6806 | (2018.01) |
| C12Q 1/686 | (2018.01) |
| C12Q 1/6886 | (2018.01) |
| G01N 33/574 | (2006.01) |

(52) U.S. Cl.
CPC .......... *C12Q 1/6886* (2013.01); *A61K 31/337* (2013.01); *A61K 31/4166* (2013.01); *A61P 35/00* (2018.01); *C12N 5/0693* (2013.01); *C12Q 1/6806* (2013.01); *C12Q 1/686* (2013.01); *G01N 33/57434* (2013.01); *C12Q 2600/112* (2013.01); *C12Q 2600/118* (2013.01); *C12Q 2600/158* (2013.01); *C12Q 2600/16* (2013.01); *C12Q 2600/166* (2013.01); *G01N 2800/52* (2013.01)

(58) Field of Classification Search
None
See application file for complete search history.

(56) References Cited

U.S. PATENT DOCUMENTS

| | | |
|---|---|---|
| 2010/0016445 A1 | 1/2010 | Beer |
| 2011/0110926 A1 | 5/2011 | Luo et al. |
| 2014/0045915 A1 | 2/2014 | Skog et al. |
| 2015/0344965 A1 | 12/2015 | Luo et al. |

FOREIGN PATENT DOCUMENTS

| | | |
|---|---|---|
| WO | WO 2014/047285 A1 | 3/2014 |
| WO | WO 2014/144850 A1 | 9/2014 |

OTHER PUBLICATIONS

Jangravi (Year: 2015) Jangravi et al; Journal of Proteome Research, vol. 14, pp. 3492-3502, Jul. 2015.*
GenBank Accession No. BC132721; NCBI, NLM; 2007.
Crea et al., "The emerging role of histone lysine demethylases in prostate cancer", *Molecular Cancer* 11(1):52 (2012).
Extended European Search Report for EP 16882723.6 dated Jul. 15, 2019.
International Search Report and Written Opinion for International Application No. PCT/US2016/069383, mailed Mar. 23, 2017, 12 pages.
Jahngravi et al., "Investigation of Histone Lysine-Specific Demethylase 5D (KDM5D) Isoform Expression in Prostate Cancer Cell lines: a System Approach", *Iranian Biomedical Journal* 20(2):117-121 (Nov. 2015).
Komura et al., "Resistance to docetaxel in prostate cancer is associated with androgen receptor activation and loss of KDM5D expression", *PNAS* 113(22):6259-6264 (2016).

* cited by examiner

*Primary Examiner* — Jehanne S Sitton
(74) *Attorney, Agent, or Firm* — Mueting Raasch Group

(57) ABSTRACT

The present invention provides methods of screening for and diagnosing prostate cancer and methods of choosing a therapeutic for prostate cancer based on using KDM5D expression level to identify which patients with hormone sensitive prostate cancer benefit from primary castration and taxane and who with castration resistant prostate cancer would benefit from docetaxel plus an androgen receptor antagonists added to the ongoing castration. The disclosure also provides methods of screening for and diagnosing prostate cancer and methods of choosing a therapeutic for prostate cancer based on a lower KDM5D expression having a more aggressive clinical course of prostate cancer in human patients.

19 Claims, 24 Drawing Sheets

Specification includes a Sequence Listing.

Figure 3
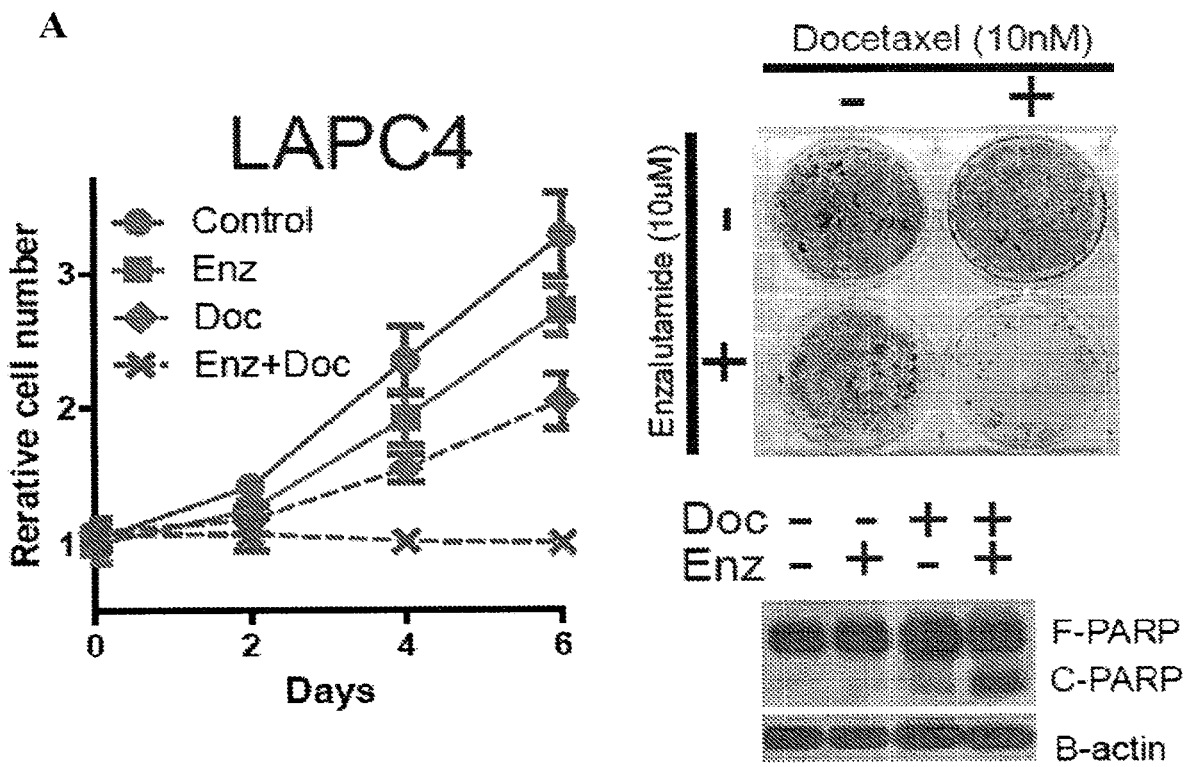
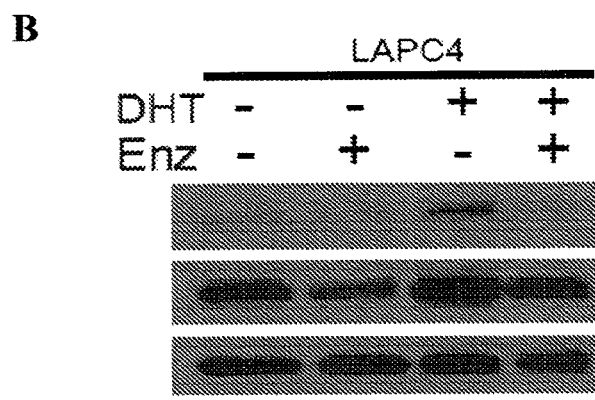

Figure 4
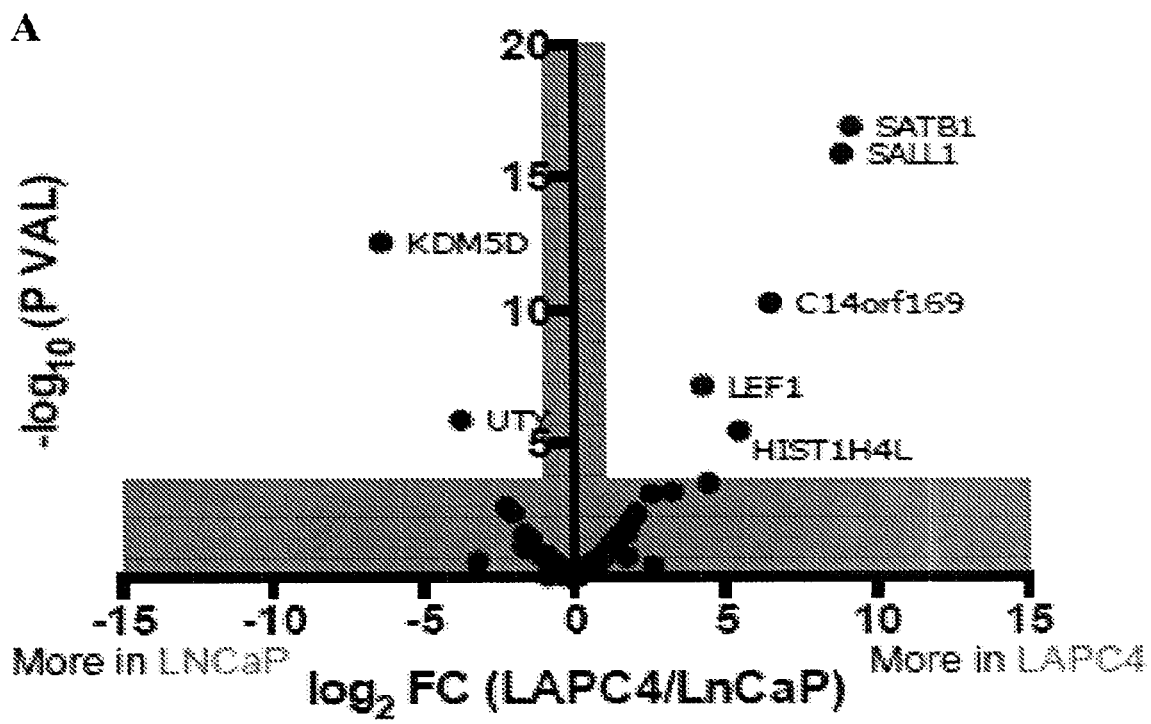
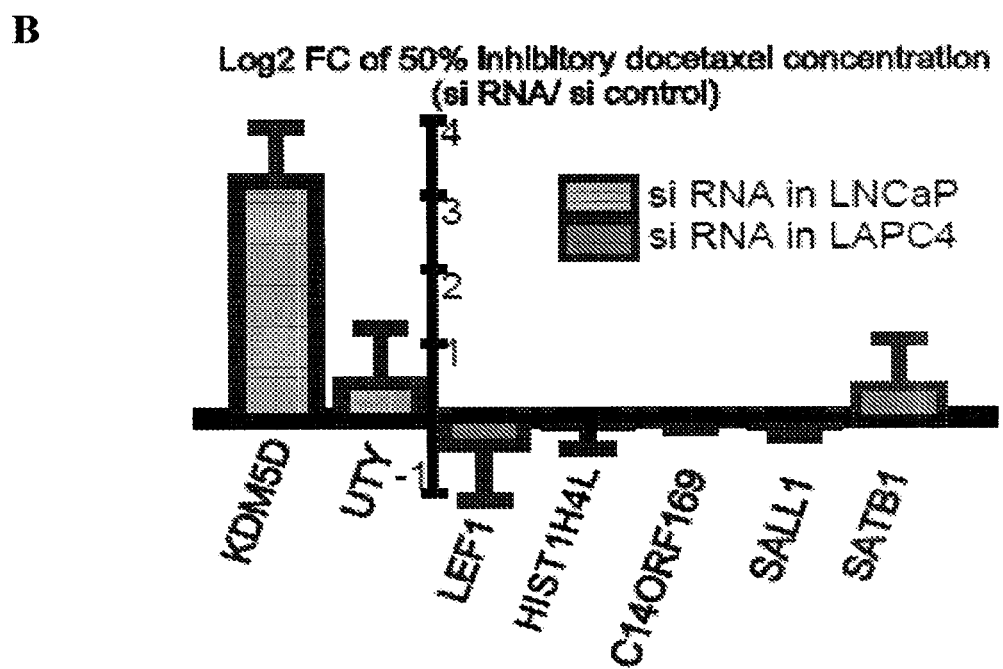

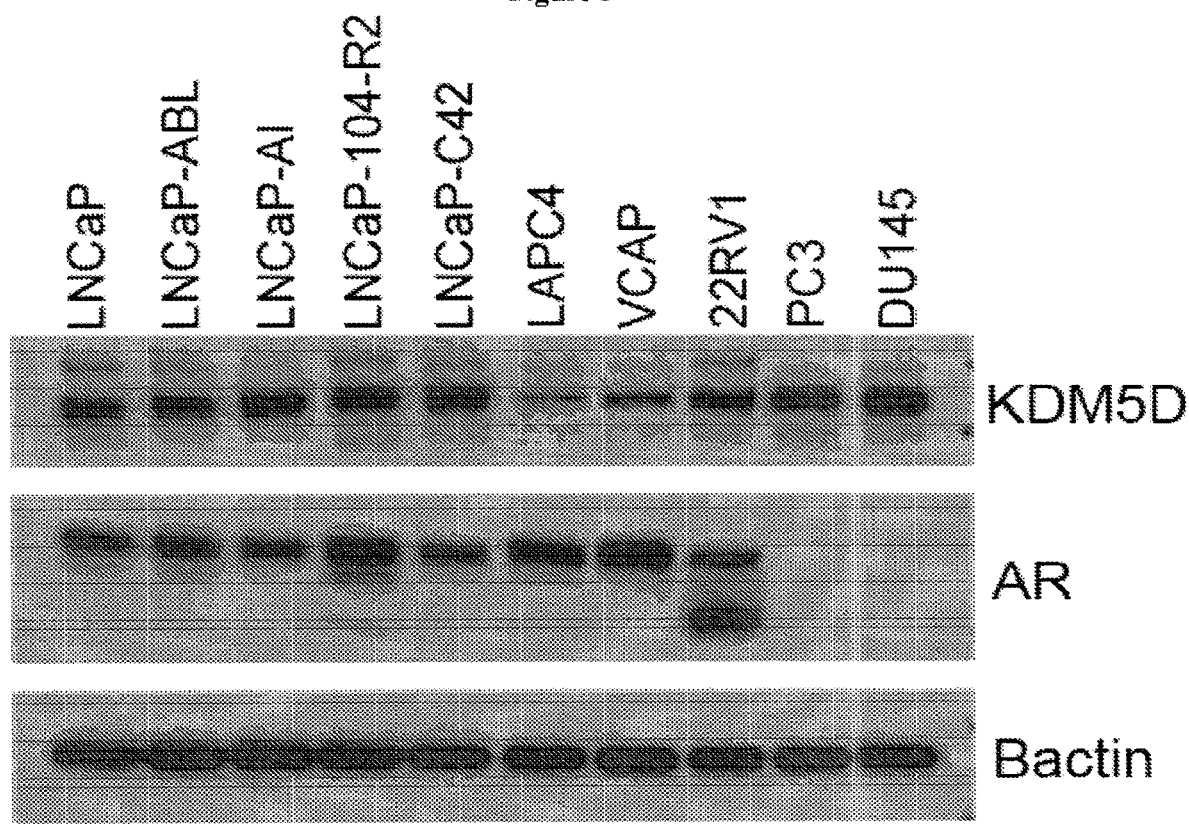

Figure 10
A  LAPC4 pLenti-KDM5D (C-terminal FLaged)
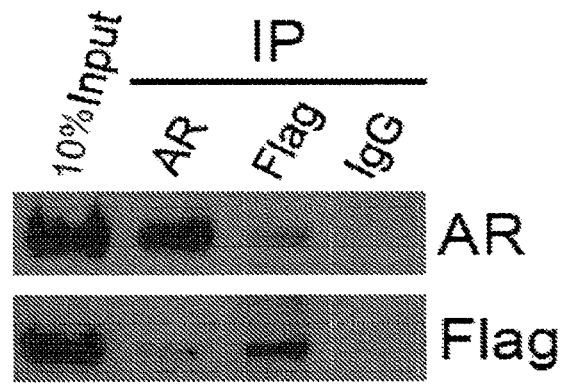
B
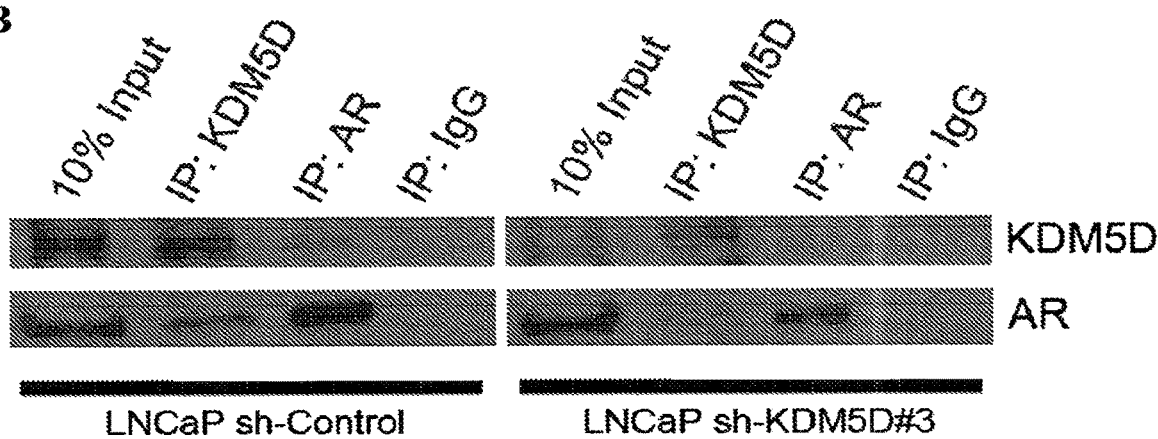

Figure 13
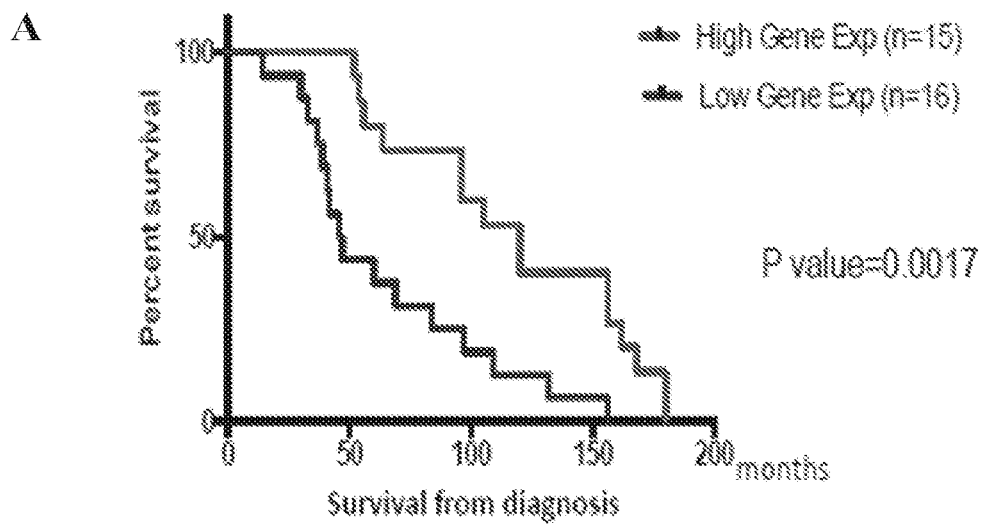
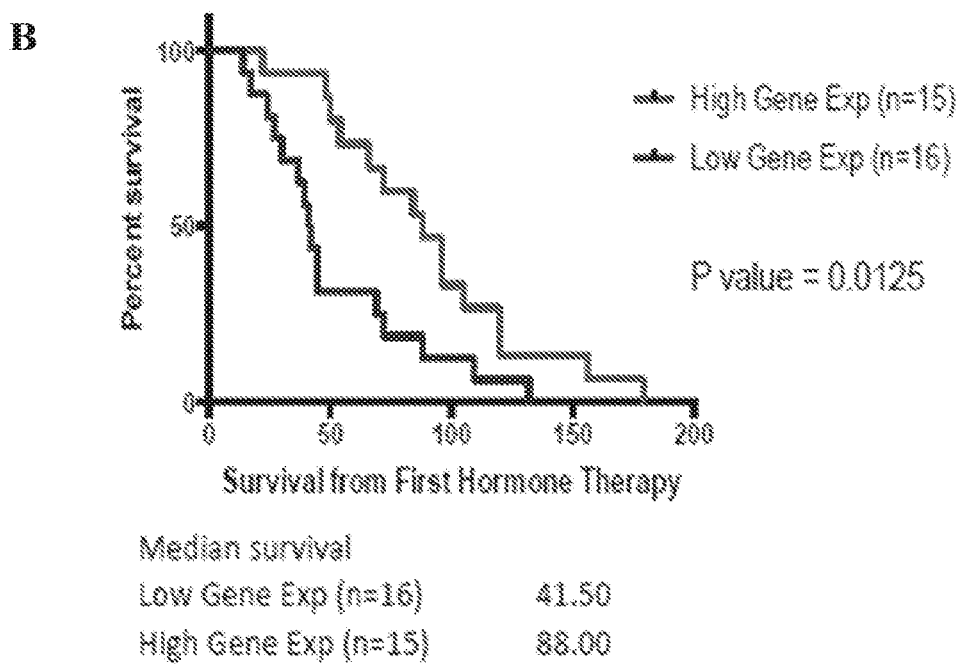

Figure 13 (continued)
C
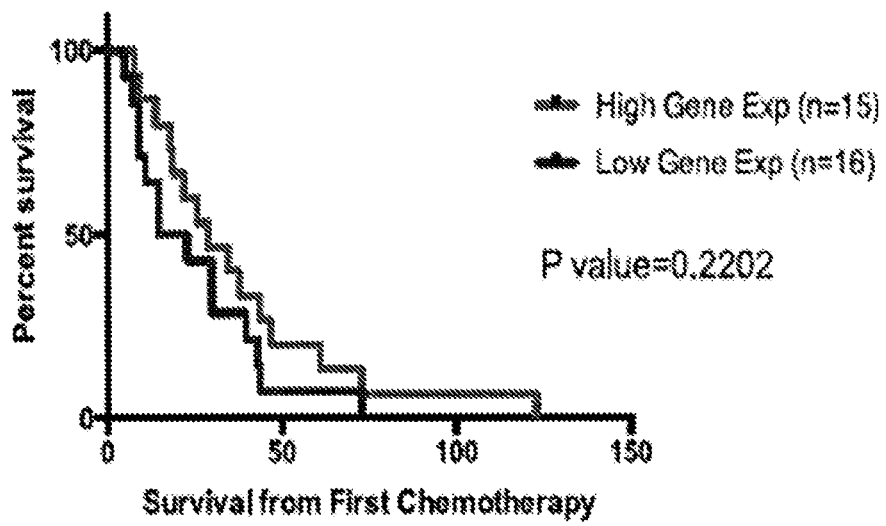
Median survival
Low Gene Exp (n=16)   19.00
High Gene Exp (n=15)   29.00
D
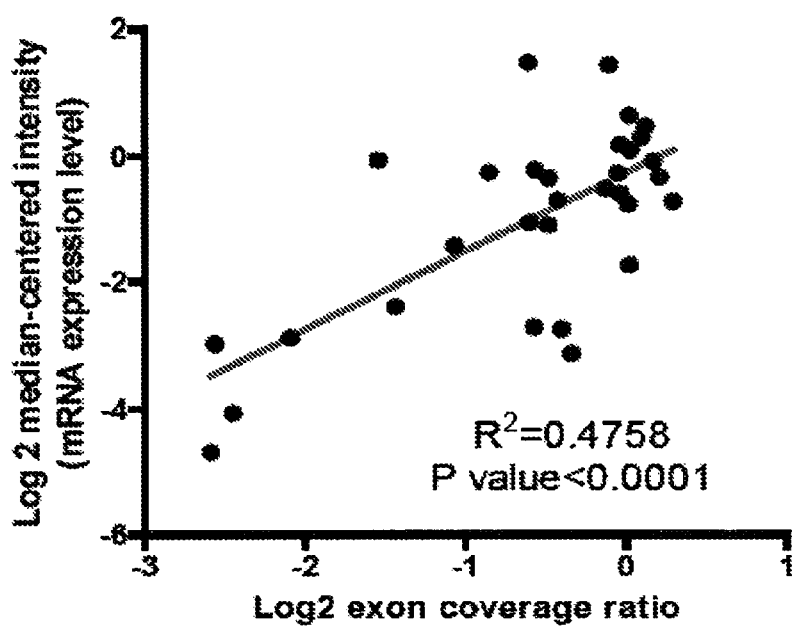

SEQUENCE LISTING

```
<160> NUMBER OF SEQ ID NOS: 9

<210> SEQ ID NO 1
<211> LENGTH: 46525
<212> TYPE: DNA
<213> ORGANISM: Homo sapiens
```

<400> SEQUENCE: 1

```
ccaccagctt tcccatataa gcagcaactt ttctctgcac acaggatttt ctctttgtta      60
gaatccctct tccccaactc catatctgta agggtacctg tttgcttctt ccttgcttct     120
ttcttattaa agtttccact ccttaaaacc actcacgtgt gtccgtgtca ttttattcaa     180
ttcagtgcaa gaataaggat cctagtgcta ctccacttat cggggccata tctggaacat     240
acctcaaaat aatgtaatga aagtcatgta tgaaaaccc actgcaaaca tcatactgaa      300
aaggcaaaag ctggaatcat tttccttgaa aactggcaca agacaaagat gtcctctgac     360
actacttgta tccaatatag tattgaaagt tctgggcaat caggccagag aaaggaataa     420
aagatattga ataggaaga gaggaaatca aattatccct gtttgcaacc aatatgattc      480
tatatgcaca caaatccatc atctcagccc caaagctttt taagctgata aacaacttga     540
gcaaaatctc acaatacaaa atcaatgtgc aaaaatcatt agcgttctta tacaccatca     600
atagtaaagc caagagccaa gtcatgaaca aactctcatt caccatagcc acaaaaagaa     660
taaaacacct aaagtacagc taaccaggga agtgaaagac ctgtacagga agaactatta     720
atacaaatca ctactcaaat aactaagaga tgacataaac aaatggaaag tattccatgc     780
tcacagatag gcggaatcaa tatcactaaa tggccactct gcccaaagca atttatagat     840
ccaatgctat acccattaaa ttaccattaa cattcttcac agaactagaa aaatctattt     900
taaaattcat gtgaaaccaa aaagagact gtacagccaa ggcaatttta agcaacataa      960
tcaaaactaa attcatcatg cttcccaact tcaaactaca ctacagaagt accgtaaccc    1020
aaacagcatg gtactgataa aagaacagac acatagacca aaggaataga atggaaaacc    1080
cagaaatatg actacatgct tacaagtatc tgattttcaa gaaaatttac aaaagcaatg    1140
gtgaaaagac tctctatta ataaatggtg ctgtgagaaa ctggctagcc atatagagaa     1200
aattgaaact ggaccttttt attactccat atacaaaaat taactcaaga tggattaaag    1260
acttaaatgt aaaacccaaa actataaaaa ccctagaagc aaatctaggc aaaaccattc    1320
agaacatagg caggagtaaa gacttcttga agaagatgtc aaaagcaatt gtgacaaaag    1380
aaaaaattaa caaatgacat ctaattaaac taaagagctt ctgcactagc aaataaacca    1440
tcaacaaatt aaatagacaa agtacagaat gggaaaaaat tgtaaactat gcatctgaca    1500
aaggtctaat atctagcata cacaaagaac ttatacaaat ttacaaggaa aaacaaaga    1560
acctcattaa aaagtgggca aaggacatga acagacaatt ctcaagacat acacatgtag    1620
acaacaaaca tcttaaaaag ctcaacatca ctgatcctta tagaaatgcg catcaaaacc    1680
acaatgagat agtatcccaa acctgtcaga atacctatta ttataaagtc aaaaaataac    1740
agattcaggt gaggttctgg agaaatgaaa atgcttttac actgctggtg ggaatgtaaa    1800
ttagttcagc attatggaag acagtgtggc aattcctcaa agacctaaag atagaattat    1860
cattcaaccc caccaatccc attactgggt atatcccaaa ggattataaa tcattctgtt    1920
ataaagatac atgcacatgt atgttcactg caggtattca caacagcata tgtacattca    1980
ctgcagctat tcacgaaagc aaagacaatg gaatcagccc aaatgctcgt cagtgataga    2040
ctggataaag aaaatgtggt aaatatacac catagatttc tatgcagcca taaaaaaga    2100
caagatcatg tctttgcagt aacacagctg gagaccatta tccttagcaa acaaacgcca    2160
gaaccgaaaa ccaaatactg catgttctca tttataagtg ggtgagtgga gcacaggagg    2220
agggagagaa gcaagaaata taactaatgg atattaggct taatacctgg gtgatgaaat    2280
```

```
aatctgtaca acgaaccta tcacacaggc ttacttataa acaaaccat catatagtgc    2340 acatgaacct ctgaacttaa aagttaaaaa atatatgtat tacaataaat gaagttagca    2400
aggtgccaga acacaagatc aacatacaaa aattaatcat atttctgtgt atcactaaca    2460
aacccttaat aggggaaatc ttttaaaaat ttgattcata gtagcagaaa tagaataaga    2520
taatctgaag taaattaatt tcaaatatat ataatacata ctaaatacta atatacaaaa    2580
aataccaaaa actataaaac tttgttgcag gaaaccaaag aagacctaaa taaattgaaa    2640
tacatgcttt gtccatgtat aggaaactta gatggaaata tttcctaaat ttgtctgtag    2700
attcaacatt tctgtctcag tcccagcttg cttgtctgtt gaaacccag cttgttctc    2760 tgtagaaaca ggcaaggtaa taaaaataca agaaacaaat aatagccaaa cagtctcgaa    2820
aaaaacaaga agaaagttgg gattactcac ttttcccaat tcaaaccttc cacaaactac    2880
agcaataaaa acaatatggc attagaatat atacatacat ataaatatgg aacgaaattg    2940
agagtccaag aataaaccca tacatttatg gccaacggaa tgttatcaag agtgccaaga    3000
acaattaatg aagcaataat aatgtttcca acaaattctg ggacaactag atggcaacac    3060
gcaaaaatat tgagttggat cattacttca cagtgtttac acaagttaac tcaaaatgta    3120
tcaaagactt taatgtagaa gctaatacta taaaggtcct agaatagagg agaagagtac    3180
atccttgtga ttttgggtta gacaaaatcc cctcagaggc aacactgaaa gtacaagtga    3240
caatagaaaa aagcaaactg gataaagatc aaattaaaaa tctttctgtt caaagtttac    3300
tattaggaaa gagaaaagcc agcttacaga attattttt ataaaaatca aatatttgat    3360
aaaagaatca gataagatta caactaaaca aaaaaagaca aaccaatgtg aaaagagcca    3420
aaaattttga atagacattt ctccagagaa ggtatataaa gcatatgaac aagccaacaa    3480
ccttacgaaa agatgctcaa cactactgta tcattagtaa ttcaagaagt ccaactcaaa    3540
actctatgag atctcataca cattgtaatg gtcaaatcag taagtcatgt aattatagta    3600
ttggtgagga catgaagaaa ctagaacggt attccacttt agatggaaat taatgatga    3660 agatgctttg gaaagaaaa gtttaaacct aaagttccca tataacccac taattctact    3720
tgtaggtgta tacacacgag aaatgacact aagcatgcac acaaaaaccg gtacacaaat    3780
gctaatagca acattataat agctaaaagt agaaattgaa atatctatt actaatgaat    3840 tcataaaata taaagctgta ttataatgaa ttatcttgaa cagagaaaaa agatctcatc    3900
atttgaaata atacaggctc tataactaat tttatgaaat agaactctat aactctaact    3960
ttatgaaaca gaaaagtat gtagataaaa ctaggaaaaa gaaagcagaa aattaagtaa    4020 caactttga aacaggaata tatatgtaat gtagtataat aaactcatga agccgataat    4080
ctagatgaaa tggataaatt gttaaaaaaa aaacggaaa tgccaagaat cgtacaatac    4140
gaaacaattg tcaaactatc aaactttaag gcacttctgg cagtgccctt ccaaataaaa    4200
tctaccattt gattttaaa acttacctt gcgtatttt tcaaaatat atggagaaca    4260 aaaagatact acagtagtga actgattaaa aaaaacaga atagcaatgt aggggattt    4320 ttgcttaacg ggtgtaaaat attgtaaata aaattatagg aaataaagtg taacatcttg    4380
ttttgaaata aacatcgca ataaagtata atttcccta aaaacagcat gatatttcca    4440
catcaaaaaa cggatcatta gcagtgtgtt tcttttgatt tatggtacgt gtgtttagcg    4500
atgttgaagg tttactgtaa tctgtccagg tctttgtgat catttaaaa tttaagggtgc    4560 tcctaggtaa tttttaaggg atgttatca tgtgcagtaa aggttttatt caaaacatt    4620 tagcacttct ttccccgtc ctaaagtcca agctcgagtt ggtaaaaaat ccaacgacaa    4680
```

-continued

```
atgtgcccac ttgaagtgca ctgttaatgc aacagtttac aagaacataa atacattgta    4740
ccggcatcct gcctcctaaa cgtcttgtga caggaacgtt ctcgagctga gaacccagtg    4800
agtcttcaga gaatgttagt aaacactttc acatgaacgg atatcgccgg cggtttgtcc    4860
tggcaggaaa aaaaaaggt gcgttttctac ggacatttcc gcaaggagg aattttctcc    4920 gagaaatcct tcgttgatca gcaccacagc cttttacggt ccttccctgc aatacgcagg    4980
cgtaacttgc gcagtggtcc cattttaaaa aagatccggc catactattt ttatcttgct    5040
ttttcgttct gtcgcagtac tgtttaatat gagtccagcg acggctctgt gactgttttc    5100
ctctggtaaa atcgctcttg cgtcctcagc gtttatctca ggtgcggaag gtctcacagg    5160
tttggaaata gcgccggaaa atcgatccg cggagtgaga cggctcgtac cacactgcag    5220
ggcccggagg tcaagatggt ggctgtaaaa ctaggatccc tgacgattgg taagcagcta    5280
cgggattaaa gtaaccttga aattctcaag aaaatgaaat tttcataggc cttttagtag    5340
gaggaaccag cgcgtcatta aagacaatgt gattcttatt ttacagctta gcattaaggc    5400
ccgacatgga accggggtgt gacgagttcc tgccgccacc ggagtgcccg ttttttgagc    5460
ctagctgggc tgaattccaa gacccgcttg gctacattgc gaaaataagg cccatagcag    5520
agaagtctgg catctgcaaa atccgcccac ccgcggtaag tctttgaaac aaaatttggg    5580
aatgggtagc ctttggtttg aacgttgggg cagtttacca cttggcgagg cgttatttac    5640
actcatgacc agaaaccctt agcaccaaat ttctcattta acttttctga cccgaacaag    5700
ctggcatcag aatattagta tcagatcgcc acattccacg gggttctaaa catctgactg    5760
ctgtagggac aaaaatataa gattcaaata tttctacgtt ctgctgttat taaatatagt    5820
ttaggcatac acaagctttt attacattta accgcaaaaa aatagcttac tcagaagtac    5880
ttgatctatg acagaagcaa gttatataag cttgtgtgtt aaccacttgg actggtgttt    5940
tctttctttg atatgacctt agatgtatgt agcaaatata gcaaataatg ggagtgatgt    6000
ggcatccttt gccatcaatt aaatttatta ttaaacgtag accattttgg gttgctatac    6060
tgaaaactac taaatgaacc tcgtagaagt ttgactgaat taagaatgta aactgaaata    6120
agcctgggct gtcgtcgtga acaactaaca caatattcag agaagtcaaa aagttttcgc    6180
agagcataca gcttttttct catatattga accaggctgc aacgttattt ttatgtggat    6240
gttcgcactt ctcagcattt gcaattaaac ttttcgtac tgctgggagt gggaagagat    6300
aatggcttag gttttaaaaa gtgaaacaat tttttatctg cattacattt atcttcattt    6360
tagtaaggac tcataaccca aatagcatag tgtttgttca gatgtgcgtc attccttgga    6420
agtcgagtcg ctttctagcc ttgggattat agaggttttt tttttttttt tcgtctgtta    6480
cgaaggacac atatcaagga gagttttgga tttgcagggt ttttccttt tttttttttt    6540 ttgcagttaa tcttgattat gaagaaggaa tcatttgagg cccttgtgta caaaaatggt    6600
taccagaaga ctttaaaaga gtgggaacaa atgattgtgg ttttcactat cttcatcctt    6660
tactgtgcca tagttaccag gtccttacac tttcttctag gattggcagc ctccttttgc    6720
agtagaagtt gacaatttca gatttactcc tcgcgtccaa aggctaaatg aactggaggt    6780
aagattggga ggcacacttt ttttaaagga atctgatctt taatcttgcc gttgtagttt    6840
cataataatg tagaacttaa gttttgaaat ctaatgtatt gaatttgaac ccgaactcca    6900 ccatttttcca gaatactgat tttggagaaa gtcttctata aaatacataa tttatgtcca    6960
caaaaatggt agaacacaaa ggctttaaat atctgaggaa gaatgatgca ttgtttcgct    7020
```

```
gttcaatagt ttcaggttag aactatcaaa atgacagtac ctttcccatt ttgtcttctc    7080
gtactcacat atttaatgaa tgaatttttt tttttgaaac agagtctcac cctgtctacc    7140
aggctggagt gcagtggcgg gatctcgcct cactgcaacc tccaccttcc aggttcaagg    7200
gattctcttg cctcagcctc tcaagtagct gggattacag gtgcacacca gcaggctcag    7260 ctaattttg tattttagt agagatggag tttcaccgat ttggtcatgc tggtctccaa     7320
ctccaaacgt taggtgatca gcctgccttg gcctcctaaa gtgctggggt taccggcgta   7380
agcccctgca cccagtgtga ctaaattttt tttagttctt aacagaagc agagttcaga    7440 caagaaatag gatcttttaa atatccagca acagagtgat ggtattacat atgttctgct   7500
ttaataaaat gtcagaggca aacttgctct ttaaagcagt caactcagtc ttcacagttt   7560
agtattcaat atagaaagta tatgaatgat ttgtcatttt cttttactct taggattttg   7620
actatgatca gtagctagaa gctgtgtatg agttagagta agaaagcagt gattcagaaa   7680
ctggttttgt gtccagctct tttacatgaa ctagaaaaat attttaattc tttgaattat   7740
atatcagtac attctaaatg agtgtcttga tgatattgag tctaaatact gttggagcct   7800
acatattttt ggtcaagcca cctttaagtc caagaataat tccttaaatt tagacatgat   7860
gttgatccta agacggcaca ttcttagctc tttatagatt aaagactcag cttatttgag   7920 cttttttgtgg accccgctgg tgagataaga cagtgaagct ggggctccgg cacgttggtg  7980
gagaagtgta gatagcatag aataatactt gttcatttac tgcatactcg atgaagtcag   8040
gttaaggagt atgccaatct tataaggccc tctctttccc aggcccaaac tagagtgaaa   8100
ttgaactatt tggatcagat tgcaaaattc tgggaaattc aaggctcctc tttaaagatt   8160
cccaatgtgg agcggaagat cttggacctc tacagcctta gtaaggtaag agtagtctac   8220
tttctaaagg aaaaacaaaa agccttgcct caaggatctt ctgtggtaga aacaataggc   8280
aggaaaggaa agaacacaga gcctggcagc gtttcttgac gtaatctttg agtcttgcaa   8340
tgattggtgt tggggaagg gcacagcccc ccatattcaa gtctcattgt tgtgttggta    8400
gccctttcca gtctgttcac agttcatcca tattgtttct tatactttca gattgtgatt   8460
gaggaaggtg gctatgaagc catctgcaag gatcgtcggt gggctcgagt tgcccagcgt   8520
ctccactacc caccaggcaa aaacattggc tccctgctac gatcacatta cgaacgcatt   8580
atttacccct atgaaatgtt tcagtctgga gccaaccatg tggtgagggc ccttaaactg   8640
gtttgtggcc tgatgtgatt ttgttttctt ttgtattttt tctttggatt ggacttttct   8700
cttgagtagt cagggtctat agattctaaa tctctagagt gaaagatgtt caggaattgg   8760
ccctagaaaa tactttgcag cctctttatg tggcatagtt ttattcctgc tatacataag   8820
taagaactag agtaacccttt ctatcttatg aggttgatgt ttactaagat cttttttatgg 8880 agaagatctt aaactagaag ttagaggaaa ccatttccta ttttaagtat cttacatgaa   8940
aaagataatc tttttttttg aaatggagtg ttgctgtgtt gcccaggctg gagtgcagtg   9000
gcaggatctt ggctcactac aagctcctcc cgggttcacg ccattcttct gcttcagcct   9060
cccaagtagc tgggactaca ggggcctgcc accacgcctg gctaattttt ttgtgttttt   9120
agtagagaca tggtttcacc atgttagcta ggatggtctt gatctcctaa ccttgtgatc   9180
tgcctgcctc ggcctcccaa agtgctggga ttacagacgg gagccaccat gcctggctga   9240 aaaagatat ggtgttccta agctttcatg aggctggttc acttgaagat agtttaggtt    9300
aaaagcttgg tgtgacttgg gtttaactca gggtgtggaa actgatttag cagggtaatt   9360
ttacataata agttaattgt ttttgtttgt ttgtttgttt gttttgtttt tgaggcagct   9420
```

```
tatcactctg gccaggcggc ctccacctcc tggattgaag tgattctcct gcctcagcct   9480
cctgagtagc tggggctaca ggcgcgtgac tatgcccact cattttttgta tttttcgtag   9540 agatggggtt tcaccatgtt ggccaggata gtctcgatcc tttgacctcg tgatctacct   9600
gactcagcct tccaaagtgt tgggattaca ggcatgagcc accacgactg gccagttttt   9660
aggttttatt atccgtaaaa ctttaaaata ttttataaaa actgtgtatt tatgtttata   9720
aacatgtttc acttagcgta cataattcta aagattcagt attttgtttt tgttttgttt   9780
tttgagacag tctcactctg tcacccaggc tctactaact tttgtatttt accgagacag   9840
ggtttcacca tttggccaga atggtcttga tctcttgacc ccatgatcca cctgcctcga   9900
cctcccaaag ttctggaatt ataggcttaa gccaccacac ccagattgag tatttttatt   9960
acttgttttt catccaggaa attgaagcac aaagagagaa gttcagtatg tttgctgaaa  10020
gcacacagag aataagagta aaaacccaga ttgatatcaa tacagtccaa agaccatgtt  10080
ctttcatatt ctgtgatgct cattcataag cagaggcacg aaaattgtca ggatatgtgc  10140
tctatccaaa gaacaagagg agtggacctg tgtaatttag aaagaactac agctttatt t  10200 gctagagttg taaatgaagg aatcacttat tacaaatatg actcaatttc tgattctata  10260
tatttttttc tctctagcaa tgtaacacac acccgtttga caatgaggta aaagataagg  10320
aatacaagcc ccacagcatc cccccttagac agtctgtgca gccttcaaag ttcagcagct  10380
acagtcgacg ggcaaaaagg ctacagcctg atgtgagtga ctgttactcc tgttattctt  10440
cctatagctg agaaggttca tctagacctt gatattgggg aaaattcatt gctgaatgca  10500
ttgttttaca tatgtctggt tcaggataaa attaattgaa atgaattatt aattattttg  10560
ttcataggtc tggtttataa tattttgtct ttgtagttt t gctttataa atttt aaaac  10620 atattgctat tgttttaagt gatggggtct tgctgtgttg ctaggctatt ctcgaactcc  10680
taggcttaag tgattctccc tctacagcct tggagtagc tggggttaca gaggttagcc  10740
atcatgcccg gttataaggt attgttaatt tctgtgaatc ttggaacgat ttttgcaaag  10800
cacactgtac aaatcagtta ttgttaactg tttgttctat tctatggtct tccatgtgat  10860
ggtcagtagg tgtgaccaca gagactcagg aaagcaaagt ttattattat cacaggcctt  10920
agagaggtag tcactatatg ctacacagtg ctagagagga aaacctatct tggatatgca  10980
gaagaagcag gaataagaaa agcacctagg ccatagccta tattgggttt accaaggaa  11040 aggcaagaca gagcaggata agaagtatgg gattggctag tttgaataat tttggcaggc  11100
tctaggctac agcagtattc cctagttgcc tgaccctaga attaaagcag aggaactttg  11160
cctcatgaat tgtatgggct gaatagataa ggattagctt tggatttgtc agtgaacata  11220
ttaaagacac attaaagtca tactcctggg tgagccatt t ggtatttgta ggagtagcta  11280
accctgggag acaatctgt cataaccaga aagatttaag atgttaaaac atcataatat  11340
tcagaaaatg aaaatacaaa caatatattt ttaataactt ttatataagt gtgttttcac  11400
tgctccatat gcaacatttt cataagattt ggatgttttt atttctgaaa taccttaaat  11460
aaggcaatgc tgtgttatct ttaggtgttt tctggataat tctaacaata tttaaatttt  11520
gagatattgt aatattagaa attagaccaa agtgagaaat tttatctagt taagattatt  11580
gaaatgcaga tggattctgt attagtactt tagttctta tagtaagaat tatgtctgga  11640
agaaactgaa taagaaaaat gaacatgtaa taactaggaa accagtaaaa tttgtttcaa  11700
gttgtaaata ccagtaaaag gtctaaacat ttttccagat aaaatggatc cttagacact  11760
```

```
tttttggcag ggagagttca ttgtccattt tgcaggaaag gttttaaaaa ttgttgggcc    11820
aggcacagtg gctcatgcct gtaatcccag aattttagga ggctggggttg ggtggattac   11880 ctgaggtctg cagttcgaga acagcctgac ccatgtggtg aaacccatc tctactaaca    11940 atatgaaaat tagttgggtg tggtcgcagg caattgtaat cctagcttct caggaggctg    12000
agacatgaga atcacttgag cctggaagac agagattgca gtgagccaag atcatgccac    12060
tgcactccag cctgggtgac tgagcaagac tctgtcaaaa acaaaacaaa atttaaaact    12120
gtacagtgta caaaaatcga cagtacttcc aaaatataaa gaaaaaaaa gttacaaatt    12180 ctgcataaag caagaaagga gaaataagga ctaacacatc ttttctattt tatgtgtgtt    12240
tgtaattcaa gaatgggtag tagactgtcc gaaatgtaga gtagtatggt attactttat    12300
tctaaaacaa gcaaatacca gctcttttaa aaagtattta atggttagaa caacctatg     12360 taacattaat gtaaaatcta taatgtacat aatacaatat tttgtgtata aaattatata    12420
ttgtgcttaa aagttgtaga agcacgaaac tgattgaatc tttttctttttt tatcatagct  12480 tattttcagg tttcctttc cagcaacccct gatgaataat aaatcaaaag tgtttaacct    12540
cacttataca ttgaaaatat gaagtaacca catatccctt tcacataact ggttaggaaa    12600
tggccaaaat gtgtcaagga tatgaggaac taggcattgt gtgcactctt tgtagtagtg    12660
aagggttgta ttaaaattaa aatttgaagt tactaaaatt ttaaatgttt acatcctcct    12720
gcttaacttc tgttaattgt cttttgagaa gaataatgca gcaagtacat aggtactaat    12780
gatttgtgcc cgagtcttaa tttatagaca tgattcagta atggtgagat ggagaggtca    12840
atgctaaaag tttagtgttg ctgactgttt atttccaaat gagatgtaca acataccca    12900 cagagccaca gtaatcagtc aggaggtaaa aggtaaggtg aaaggcacag gtcacagcct    12960
ttattggtat ttctgtgaga caggcaaggc agggcaatca aatgtcagaa ttggctagtt    13020
tgttagaata attccaggga tctgtgaggc atagtggatg ccggtaggtt tttggtacat    13080
ggctctgagt tggtttacag aagggggaaat actggttcta tatgatagtt aaataaagga   13140
aatagttaga ggtttggact cgggattgtt tggtttatat ggtaaaggta tagtttagtt    13200
tagccagctc tgaaagagct ggtctcccta gcccacaagg tacccagaa atgtcaaaac    13260 catataaggt atataaaata aaaattagat taatacagtt agttacttag ctcttcagaa    13320
tgtcaaaaag tgggaaacag cctcaatgtt gtataattaa aaagttagtt aaatgattgc    13380
tggaatagta ttataataag caatgtattc tcatagacgt aatgcaatat acgtttctgc    13440
ttccagaaat tgccgtggga ataaaaaaaa agcataaaat atgttactgt gtctctctgt    13500
gtatacatgt atgtttatat atgtaaatag aagaaaactt acctctgtat agaaaatttg    13560
taagaataaa gctttaaaat aaacggaaaa tgtaatagag cttaatttca aaatataaca    13620
aattatttta aacaatgata aaatatattt tacagtgtcc tctaagaaga gacaagtgct    13680
gaaaatggta tataatatat gtggcatatg atttgtattt tgatacttaa tgagttttcca  13740 ttttcccagg tttgtgatta tattgtggtc tgaaagcagt tatgattcta atgatatgag    13800
tttaaatgga atagaatttt tcctgtctta actgttttcca tcttgaactc agttggagag   13860
gggggcttat ttttaattac aaaattctct gttgtaaggt ataaatttct gacatttaag    13920
cttcactagc cttggaagcc ttggattatt ttgtcatttt tttcataaca tgaaaaagt     13980 tgaggaaatt cattactttc caaatttatc catttgctcc tacctggcca taccacactc    14040
acagtaaaaa tgtggttaat aaacattcaa aaatggataa aggatgttag ttgatttag    14100 cccatctgac ttgtccagac cttgcctata aagtatttat acctgcataa gtaaagctaa    14160
```

```
cttcgttgtt tgaatctttt ttaaaacagc cagagcctac agaggaggac attgagaagc    14220
atccagagct aaagaagtta cagatatatg ggccaggtcc caaaatgatg ggcttgggcc    14280
ttatggctaa ggataaggat aagactgtgc ataagaaagg tgaggaactt taacagattg    14340
gggaagtgtg aggggtaaaa tagtaaagtt tcatgggaga aatagtttgg taatcttgat    14400
gcaggagagg attggtttca tagttgtttt ttacttccct agtcacatgc cccccaactg    14460
ttacggtgaa ggatgagcaa agtggaggtg ggaacgtgtc atcaacattg ctcaagcagc    14520
acttgagcct agagccctgc actaagacaa ccatgcaact tcgaaagaat cacagcagtg    14580
cccagtttgt aaggactcat gattttgtaa tattctactt tgaaccgtca agattatatt    14640
gaacctaaaa tgaattcatc atactttcct ttttttcttc cttctttctt cttatttatg    14700 agcccttttα tctgaagaga cgggtggcta gaaatgggag gaaatgtttt caagatagct    14760
aaagtcaaaa gcaaaatttt tatgtctttt tagatagaac ttttcaccaa actatactct    14820 gttttttcaac tctattagca ttttctgaac ttttacagct taatatagga gataatgtga    14880
tccaatataa attatgttaa agagctgttt atttgttttt ggcaaattcc tccagactct    14940
caaatcatca catttcatat agtagtgaca gttttctatt atcttctttt acttttgtcc    15000
cttgtatgtt tacatcttct tttattcttt ctacatctca cttggaagat ttttataatg    15060
tcttacatat ttaagtctgc actacaagaa aaaaaaaag acaaaaattc ctaccttcct    15120
ccttactctt tagctaatct caccctgttt tgataatttt tgtttgcctt tcctttatgt    15180
aaatgatgtt tccagaaaatt tgttctcaa acagacttct gttttgagct gcaaattcct    15240
gtgtttctct tagtcatttc cacctgatga ttgggagatc atgtttacta ccactgtcct    15300
gttcccactt gtctcactgt tttgcatttt atagacacaa ggtagagctg tcatcagtct    15360
ggaagtgtag gagtcattga tcactacttt ctaacccttα cagctagtag ttaacttcat    15420
tccattgctt ttgttttttat ttctgtgtat cacccataca caaaaatatc tggattactt    15480
ttacttgttc gtgtactttc aattaatcac ctcttttgta ttggcttctt cttttagtgg    15540
ttcaaaaaat gcatttatat ggttctatta atgctcacgc ttgtgttcta ttaagtgtag    15600
ttttgttagg catagctttt tttctatctg ttttaccatt caacttttgg tagttaccaa    15660
tttttggcta tttcaagtaa ttctgtggat attaaagtat atgtttctag gtaacgtatg    15720
tagacatttc tgttacctag atagacagga tagaattgct gtgactgaga ctatgtatat    15780
tttcactagt ggattattgt cagactgttt ttacaaatga ttgacgagtt tatcagctag    15840
tattggatgc cagttctggt taccacatgt cctcactaac acttagaatt gacagttttg    15900
ttttcatttt agccattctg ggaggtgtgt agtatttcat tgtaattttt atttgcattt    15960
ccctggttta cagttttttα tattgagcat ctttcataag tttaaagat ttttattta    16020 tgaaacctttt tcctgataat tctgttgaat ttttttcttt tttctgaga tggaatctcg    16080 ctctcgccca ggctggactg cactggtgcg ctctcagctc actgcaacct ccgcttccag    16140
ggttcaagca attcttctgc ctcagcctcc caagtagctg ggtctatagg tgcaagccgc    16200
cacaccctgc tagtttttttt tttttatttt agtagagatg aggtttgacc ttgttgtcca    16260
ggctggtcgt gaactcctga gctcaagcaa tctgcccacc ttggcctctc aaagtgctgg    16320
gattacaagc ttgagccacc gcacctggcc tcttatgttt ataaatattc tgatttgtca    16380
tatgcatgtg tgtatatgcg tgcatatgta tgtgtatata tgcatgtata tatgtatata    16440
tacacatata atttgtgtgt gtatgtttgt gtgtatatat atttaaaaat atatttatat    16500
```

```
tttcacacag tttcttctgc tcttgagtta tctttaaaat tttctcttta ttgatcagtt   16560
tacttctaga ttcttgtaga aaagcccatc ctacttattg aaggtaattt tttcaaaatg   16620
taagtgtacc ctgctaaaaa tcttaccact gcgttttctt tttaaactgg taattattac   16680 tagattttt tcaatagtat gtaagaatca agttatttag cctttgcttc atgtttctct    16740
tctgtgacat actacttgag tgactattta taattcatca tctaatctaa gataacccrt   16800
tataatgaaa gtatatgtct atcaaacttt tcaacagagg aacaactata actggatatt   16860
cggtcacttg accttttat gttcaacttg ccctctgtgc cagataaatt tttaactatg    16920
taattctctg atctatgctg ctttatacct ttatgatttt tgtttacgcc gttgaacctc    16980 tataaaagt ctactttgcc cccatggttt ctttattaac ttactgtatt atagtgtaat    17040
tatttcctgt catagtttgc actaggtagt aagctcataa atacaacact gtatagttat   17100
tgactaatga tagatgttca tgaatggtct agaaacctgc gataaggtgt cagggaacaa   17160
gcagctaaat ttttactttt ttttttttt ttggtagatt gactcatata tttgccaagt    17220
atgctcccgt ggggatgaag atgataagct tcttttctgt gatggctgtg atgacaatta   17280
ccacatcttc tgcttgttac caccccttcc tgaaatcccc agaggcatct ggaggtgccc   17340
aaaatgtatc ttggcggtaa gatctgtctg tcacagatgc tttattttg gttggtgatt    17400 ttctgtaatc tccccttctg ggttttggga aggtagtttc tgcccttta taagttaata    17460 tttgtgttag gttttgatta agctatcagt gagctactat acaagaacga ttgaacacac   17520
taactctaga atgatagaga cttgactgaa ccagaggcaa gggactataa ttcaaatggc   17580
atgaagcatg taaggaaaga ttataaaata atgtttaata cctactgaag aaacaaacct    17640
acctggaaac atatgaaaat gcagaattat tgcatgagat attgaatgta acatgaaaaa   17700
tttatctccc cttagctctc ctgtttttt ggatctttat tcccttgtc ttgctgaaat     17760 atattttatt tcaggagtgt aaacagcctc ctgaagcttt tggatttgaa caggctaccc   17820
aggagtacag tttgcagagt tttggtgaaa tggctgattc cttcaagtcc gactacttca   17880
acatgcctgt acatgtatgt gatctgaggg ctggactata gggattctgt tgtggtagtc   17940
ttagttctca tggagacatg agtccaaagt atagtgggct atgataacct tttacatgtg   18000
ttttcacaga tggtgcctac agaacttgta gagaaggaat tctggaggct ggtgagcagc   18060
attgaggaag acgtgacagt tgaatatgga gctgatattc attccaaaga atttggcagt   18120
ggctttcctg tcagcaatag caaacaaaac ttatctcctg aggagaaggt aatacggttg   18180
gtagttcatg ttaacattaa ctagggaaac tcattttagc atgtaaaatt actttcctag   18240
gttctcccac acagtgttgt cttcacatat ttcggataat aatgaggttt gatgatactg   18300
gttcatgatc tgtcagtgaa ccggaatatg gacagtcatc gtatttttt tctcttgaaa    18360 ctctgatgga gatagataaa aggaacagta taaatcttga tattatcaat gaagagctat   18420
agtgttcctt cacctttcct taaatctaaa tattggaagc ttaccatctt tttatgaaaa    18480
gcaagtacta tgaccagctt attttgaaat atttggaagg gcggaaagaa gtatctttgt   18540
taagtgtatc aatttgtgtt catgtcgaac atacggagta atgcagaaac cactgatttc    18600
attcattaca aagtgatttc ttgtattagt caaagaaacc catacagcca tcctaaattc   18660
tgactcatca catttacatt tctcctgtag tggagaacca aaaaaaataa tgcctgaagt   18720
aacataattt ggggagagaa agctaaaatg tagccgtcct tatgcattat ttgaacattt    18780
gagaaattaa ttctatttcc tgttttacca tgttggccag aaccaaaaga attagtattt   18840
ggcattgtat atagattagt cttacaagag ggttgatcca gacagaaaaa atagtggttt   18900
```

```
gaggataaac ttagctaata gctgtgacta acattttag  gaagtcttac tctgatttt  18960
ctgtatatat actgtttgtt catggagatg tctgtatctg gataagcgct attttatagt 19020
cggtcatatg ctgcataaca ttttgagttt aataaaggag caatactgta ctttcactat 19080
atcttttctg tgtttagagg cacagatact taaaccattg tgttacatgg cctataatat 19140
tcagtacaat agtgtcgcac taatttgtag cctaggagca atagttatat accatatagc 19200
gtaggtatgt agtagattgt ttcttcttgg tttgtgtgag tatactctat gacgttcaaa 19260
aaaggacaaa atttacctct tttgttaaga gatgtgtagc tgagtatgat agtgcttaaa 19320
agtcttacag atagtttggt tatagttctt aaaatagaag taagttaaaa ttactgaggg 19380
attgaaacta taaattaagt aattggaagg caatcaccta tagcctccat tggtaacttt 19440
ggtctgtttc taattccctt tttgaaacaa ccaaaaaaca aattgtattt tgaagccata 19500
gacaagtcct tttgtcggta taaagcatgg tattaagtaa tatccctgag ctaacttttg 19560
aacataagaa ttgaagtttt gtgagataat atctctccac aggcttttct gcaagtcata 19620
cctccctctt tctctccact aacacctaaa tgttccaccg tcatgggttt gtcataataa 19680
aaaaaagtgt agtgtttgat tacatatgta tgtattttta aaagaatat  taattttcaa 19740
gctttgctaa tgttacgttg tgtgttctct gacttgttct gtcagtattg tgttaggaaa 19800
attcatttat attgttgctc atagctttaa attatctgtt ttttcactat tatataaat  19860
tgcatgctgg gattacatct catttatctt tctttctgtg gattgcttct ggtgtttagc 19920
tgttactaac agtgtatgag cattgtttta caggtctcct gaaacaacag tttctaggtt 19980
ctatgtttag aagtggaatt gaacgatact ctgaattgtt ttacaaaagg attctgacag 20040
gttacactga aactaatgag agaactggtc atccatatgt ttaacagagc acttcatact 20100
gttacctact tttgtgggta tgatatgttc ccacgtagca ctatttcatt gattactaag 20160
gtcaaacact ttccattagc ttattccaat ggcaagcctt taagagcatc agattatccc 20220
atctgctaaa ttattggaca caccatttat gcttaactaa tacatatata tgtgtataga 20280
tatttgagta tatgcagaat atttgtatta accccttca  taatgaattt gtactggtat 20340
taattttta  acttttataa aacaaataaa tactttggtc tctatactgc ccctcagtcc 20400
cgttcctgct agtttccttt ggatcttaga tctagtttat ctttctgtat acataggctt 20460
taaatgttta acttgtaact aatgcagaat tgattttttt aatccagtga gttttatt  20520
tttaattagt taattttcat ttattgtgac tgatgattgc atccatttt  tgctatctta 20580
ttttgaactt agtttctgct gccttttctg ttatcttttt tttgcctttc ttattccatt 20640
ttagccactt gtaagtttag caacttttgt atgctagttt taatactatt ttattttatt 20700
tcattttatt tatttatttt tttttgagac gcagtctcgc tgtgttgccc aggctggagt 20760
gcagtggcat gatcttccct cactgcaacc tccacctccc aggttcaagc aattctcctg 20820
cctctcagcc tcccaagtag ctgggattac aggcgtccac caccacgccc agctaatttt 20880
gtgtattttt agtggagatg gggtttcgcc atgttagcca ggctggtctc gaactcctga 20940
ccccaggtga tccacccacc tgggcctccc aaagtgctgg gattacaggc gtgagccacg 21000
gtacccggcc taatacttta ttttacatat aacctaacat ttaatttttt ttttacttct 21060
cccaagtaat attagactat ataacttact cttcagttct cttctgacct ataaaatttt 21120
tgtgcatgtt tttaaagctt tttgctcaac aaaatggatg ctgttttgt  ttttatactg 21180
catatagatt tatccacaca tgattttttc ttttgattat ttgaaattct tgcaaccatt 21240
```

```
ttctttgttg ctgaagtaaa ttctttagaa atttcttaaa aagcccaggc gcagtggctc   21300
acgcctgtaa tctcagcact tgggaggcc gaggcaggtg gatcacgagg tcaggaaatc    21360
aagaccatcc tggctaacac agtgaaacca tgtctctatt aaaaatacaa aaaattagcc   21420
aggcgtggtg gcgggcacct gtagtcacag ctgttaggga ggctgaggtg gaagagtggc   21480
atgaacttgg gaggcagagc ttgcagtgag ccgagatcgc accattgcag tccagcctgg   21540
gtgacagcgt gaatctctgc ccagaaaaga aaaagaaaa aaagacattt attgaacaga    21600
ggcatttgtg aatttttatt cttataaagg tatttctctg tatatatacg gatgtggttt   21660
gataattgtc ttttcacagt acattagaaa tctgttttgg cttttgacaa gtcaattctg   21720
aatcttacat taatttgtag tagtctattt tgcttttcct atttgactgc tataatatct   21780
cttttagtgt cttgcaagtt ttcttgatgt gtggaatgtg acttttttact taatatttct  21840 gggaatagat aggaattctc aaacttgaga attcagcttt taccacttct gaaaaattct   21900
tggtcatcaa cttttacagt ctgtaattta tttctcctgt tagctagaac cttactgttc   21960
taaggttctc ttgtatgtgt ttcttcacct ttcattttt tttaattctt ttgctgctgt    22020 tgtctttttaa gtaacttact taaagcaact taaaaatgta ccagttttta aaatacctaa  22080
tctattaaac aacttagttt ataattttta atgttatgtt tttatcttta gaattctga    22140 ttattttttca gactttccta gttaatattg aaaaccttttt tctgctcata cttcttttat 22200
cctcttattt aaattaaact gatttatct tcaacaccta gttattatag catattctga    22260
gaactaatta tagcttgatg ttttctcaac aaattttac tcattttaca accccgctc     22320 catattttat ggctttgatt taattagtgt ttttcgttgc tgttgttttt gttttctgat   22380
gaacttgtat ttctttgaac aacatgtatg ggaatttttt cagaaaccta gattttaatg   22440
tccagctaca gaatagactg tttctgttta atgttaagga ttcccttaag acgataaaaa   22500
atttttagct tcacatttcc aagtaaatgt gaatagttgt gttttcaagt aaatatgaat   22560
tcttgtgtgg atggctgata gataagaact cttaggagta tctttccttt tcttcttgtg   22620
gaaacagtac caagataagg aaagtattta atatctgttt cttcaggatg ttttttcacct  22680 ccttcagttt tatagctaaa aggataatag tactgtcacg ttgtaagtta aagaccctaa   22740
tatgaccttc tttggaagct ccaaattttc tcttttatgg ttgacccgaa ttgtcatcag   22800
tttcagaact ttaatttgta catgttattt cttagtgtta ttctctgagg attttcctta   22860
ttttctaagc agctgagcca aaacatttaa aaaatacatt ttcttatcta gcatgttgag   22920
gtcctttgtg attcctctga acgtctaacc acaatgtagt tgaaaattga agttgtatgt   22980
attaaacttg taattcagaa gttttggaa ctattgtttt acaatactgc agataagtat    23040
aatcatataa ttttcttagt ttgtatattt agcttttttt ggaattttt tcaaatatat   23100 tcctgtcatg ttaattattt caaataataa aacatactga acacatgata cttttatcaa   23160
aagaaatata atatggcctt ttatttgacc aaaaattctc ctattattct gtagtttatt   23220
tatttatttt ttaattatac attaagttct gggtgcatgt gcagaatgtg caggtttgtt   23280
acataggtat gcatgtgcca tggtggtttg ctgcactcat caatctgtga tctacctacc   23340
ttaggtattt tccctaatgc tgtccctccc ctagtccccc agccctgaca ggcccccag    23400 ccctgacaga cagatgttcc ctgccctgtg tctatgtgtt ctcattgttt aactcccact   23460
taggagtgag cacatacggt gtttgttctt ctgttcttgt gttagtttgc tgagaatgct   23520
attaccagct tcatccatgt ccctgcaaag gtcatgaact catccttttt tatgattgca   23580
aagtattcca tggtgtatat gtgcaacatt tttttaatcc agtctatcat tgatggacat   23640
```

```
ttgggttggt tccaagtctt tgctattgtg aacagtgctg cattaaacat acatttgcat    23700
gtgtctttat agtagaatga tttataatcc tctgggtgta tacccagtaa tgggattgct    23760
gggtcaaatg gtatttctag ttctagatcc ttgaggaatc gccacattgt cttccacaat    23820
ggttgaacta atttatactc ccaccaatat tgtaaaagtg ttgtttgtcc acatcctctc    23880
cagcatctgt tgtttcctga cttttttaatg attgccattc taactgccgt aagatggtat    23940
ttcattgtgg ttttgatttg catttcccta atgaccagtg atgatgagct cttttgaaat    24000
atatttgttg gctgcataaa tgtcttcttt tgagaagtgt ctgttcatat ctttcggtca    24060 cttttttcatg tttttttttt tattcttgta aagttgttta agttctttgt agattcttga    24120
tattagccct ttatcggatg gatagataac aaaaattttc tcccattctg taggttcctg    24180
gcctgtcacc ctgatgatag tttcttttgc tgtgcacaaa ctctttagtt taattagatc    24240
ccatttgtta attttggctt ttgttgacat tgcttttggt gttttagaca tgaagtcttt    24300
gtccatgcct atgtcctgaa tggtattgcc taggttttct tctagggttt ttatggtttt    24360
aggtctcatg tttaattctt taaccatct tgagttaatt tttgtataag gtgtaaggaa    24420
gggatcaagt tttagctttc tgcatatggc tagccagttt tcccaacacc atttattaag    24480
cccattgctt gtttgtgtca ggtgtattaa atatcagatg gttgttgatg ggtggtgtta    24540
tttctgaggc ctctcttctg ttcagttggt ctgtatatct gttttggtac cagtaccatg    24600 ctgttttttct tgctgttgcc ttgtactata gtttgaagtc aggtagcttg atgtctccag    24660
ctttgttctt ttggctttgg attgtctctt ggctatgcag gctcttttt cattctgtat    24720 gaaattgaaa gtagtttgtt ccagttttgt gaagaaagtc agtggtagct tgatgggtat    24780
agcattgaat ctgtaagtta ctttgggcag tatggccatt tcacgatat tgattcttcc    24840 tattcatgag catggaatgt ttctccattt gtttgtgtcc tctctgattt ccttgagcag    24900 tgcttttgtag tcctccttga gtaggtcttt catatccctt gtaagttgta ttcttaggta    24960
ttttattatc tttgtagcaa tagtgaatgg gagttcactc atgatttgac tctctctttg    25020
tctgttattg gtgtataggg atgcttgtga ttttggcaca ttgattttgt atcctgataa    25080
agttgcttat cagcttaagg agattttggg ctgagacgat ggggttttct aaatatataa    25140
ccatgtcatc tgcaaacaga gacaatttga cttcctcttt tcctaattga atattgttta    25200
tttctttctc ttgcttgatt gccctggcca gaacttccaa tactgtgttg aataagagta    25260
gtgagagagg gcatccttgt cttatgccag ttttcagaag gaatgcttcc agttttgcc    25320 cattcagtat gacattggct gtgggtttgt cataaatagc tgttattatt ttgagataat    25380
gttccatcaa tacctaattt attgagagtt tttagcagga aggactattg aattttgttg    25440
aaggcctttt ctgaatctat tgagataatc atgtggtttt tgtcattggt tctgcttacg    25500
tgatggattg tgtttattga tttgtgtatg ttgaaccagt cttgtatccc agggatgaag    25560
ctgacttgat cattgtggat aagcttttat tttaagttca ggggtacaag tgtagtttta    25620
ttacataggt aaacttgtgt catggggatt tgttgtacag gttatttat cacccaggta    25680 ttaagcctag tacccattag ttattttcc tgatcgtgtc tctccccccca ccctccaaac    25740 tccaaaagtc ccttatgtgt ctgtgtattc tctcatcatt tagcccctac tcataagaga    25800
gaacatgcag tgtttggttt tctgttcctg tgttattttg ctaagaataa tggcctccag    25860
ctccatccat gtcttagcaa aggacatgat cttttttatat gcttgttggc cacttgtata    25920 tattttttaag aggagtgtct actgatgtcc tttgcccatt tttaatggag tgattgtttt    25980
```

```
ttgtttgttg atttgtataa gtttgctgta gattgtgaat gtcaggatttt tatcagatgt   26040
atagcaaata tcttctccat tctataggtt gtttattctg ttgacagttt cttttgctgt   26100
gggaagctct ttcacttaat taggtcccac ttacctattt ttgttgcatt tcctcttggg   26160
ggcttagcca aaaattattt gccaaggcca ctgtcgagaa gactgtttcc ctaggattac   26220
tgtagtttga ggttttatgt ttaaataaat ctttggttca ttccaagtta atttcttttg   26280
agacacgatt tctctgtcac acattctggc gtgcagtagc acagtcatga ctcaccttat   26340
tgcagcctag aacttctgag ctcaaacacc cctcacactt cagcctccct agtagctggg   26400
agctatcaca ataaaagttt tataaaataa gaaattttta caaagttgtt attttttaca   26460
ttagtagcta ttatactttt ttaatatttt taaatttttt ttttagagac aaagtctcac   26520
tgtgttgacc aggctgatct caagcttctg ggctcaagca gtcctcccac cttggcctcc   26580
caaagtgttg ggattacagg tataagccat catacctggc cttgagttac ttttttgcaca  26640
tggtgaagta taggtgtcca ccctcagtct tcagcatgtc ggtagccagt tactccagca   26700
ccatttattg aataggaagc cctttcccat tacttacttt tgttggcctt gtcaaataac   26760
agatggtagt acgtgtctgg ctttatttct gagttttctg ttctgttcca ttggtctttt   26820
tgttggtctt tgttacagta ccatgctgtt ttggttactg tcgcttcata ttatagttca   26880
aaatttgggt agtgtgatgt ctacatcttt gtcttttggc ttaggttggc tttggctagt   26940
tggggctctt ttttaagtt ccaaatacat tttagaattt ttttcaactt ctgtgaagaa   27000
tgatgttgat ggtttgatag aaatagcgtt gaatctgtaa attgctttgg gtggtatggc   27060
catttaatt atattgaatc tttcaatata tgggcatgga atggttttcc atttacctgt   27120
gttatctctg atcttttata gcagtgtttt ctggattttc tggtagagat ttttcaccta   27180
cttggttagc tgtatttcat agtatttcat tttctttatc ttttgctcat ttttaattag   27240
tttttttttt tcctattgta tttgttcagt ttcttacgtt ttggatatta accttttatc   27300
agatgcatag tttgcaaata cattttttcca ttctgtaggt cgttgcctta ttctgttgat  27360
gtttccttca ttatgcagaa gcttttagc ttaatgtaat accatttgtc tgtttttgct   27420
tttgttgctt atactttga ggtcttaatc cacaaaattc ttgccaagat caatgtcatg   27480
gagctttcct cttatgtctt cttttagtag tttgataatt ttggatttta catatttac   27540
atttaagttt ttacttcctt tggggttggt ttttgtacat ggtgaaagat gggtcaagtt   27600
tcatcctttt gcatgtggat atccaggttt tccaacaatg gatactgaag agacttttcct  27660
ttcctctctg tgtgttcttg gtgtcttttgt ggaacttctg ttggctgaaa atgcagagat   27720
ttatttctgg gctattattt tccatggagc tgtgtgtttg ttttttaatgg cagtactaag   27780
ccctttagt tactatagct ttgtgatata atagtaaatt agtgtgaata ctctcagctt   27840
ttttgtttgt tggtttgttt tgtttcacat attgctttgg gtattttgag tctttggggt   27900
tccatatcaa tttaagggtt gcttttttga aaatttctgt gaaggatgct gttattttttg  27960
acagggatta aattgaattt ctagatcagt ttggatagta tggacatttt agcaatatta   28020
attcttgtgg tctgtgagga caaggtgtct taaaatttct ttgtgtgttc ttcagtttac   28080
ttcatcatta tttgtatagt ttgcagtgta gttattttt tacctcttta aatttattgc   28140
tagagatttt tttcagctgt tacaaatgaa gttttatttt tgtttttttc agataatttt   28200
ctactaatgt atacaaacac cactgatttt tatattgatt ttgtatcctg caaatttact   28260
gaatttgtta gttctaacac catttttacg gaggccttag catcctctta aaaagaagt    28320
gttttcttta agactttttt ataaatcttc aaacagggat aacataactt tctctttttcc  28380
```

```
aatttgaatg ttttttttaat ttctttttcct gcctcattgc tctggctggg acctccggca   28440
ctgtgttagt tgacagtggc aaaacagggc attattttttg agtttacaat atggacctct   28500
tgtgaccagg aataccagag gcagcatgtt ctaagacaca gttgtcttct tatgtatgtt   28560
ttgctcagtt tgcctctcct catcgtatcc tactccctac tcactctggc aaatctctga   28620
cccaacagga gtatgcgacc agtggttgga acctgaatgt gatgccagtg ctagatcagt   28680
ctgttctctg tcacatcaat gcagacatct caggcatgaa ggtgccctgg ctgtacgtgg   28740
gcatggtttt ctcagcattt tgttggcata ttgaggatca ctggagttac tctattaact   28800
atctgcattg gtgagcatga ccccaatggc tcagttggat atcaagactg ccctcatatg   28860
caacgatgta tatagacttg acgtgtcttc tgtctacgtg agcaggggtg agccgaagac   28920
ctggtatggt gtaccctccc tggcagcaga gcatttggag gaggtgatga agatgctgac   28980
acctgagctg tttgatagcc agcctgatct cctacaccag cttgtcactc tcatgaatcc   29040
caacactttg atgtcccatg gtgtgccagt aagtaccaag gatcaaaaca attttaatttt   29100 tcttccctgg ggtgagaagg gaatgagaaa gaacttagtt ttggaagaaa taaaaccata   29160
tccattttgc tatggagatt aggcttagca tcacacctct ttgccttccc ttgctgactt   29220
caagttgcag atcagtaccg ttagctggga cacttaagag aacaagtaaa agagagatta   29280
gataattact taacagaata gaaattaaaa cttggatcct ggccttttta tctgccttct   29340
agtctaggat tggttttctc ttaatatttc tgaatataat tcttactttg caaaacccag   29400
gagggactgg tttcagactt ttgagtattt ctaggagtgg attgtatcag ctcattttgc   29460
taaagaataa gctagcaatg tgtatgtggt acatggactg ggtcactgtc ttgttacatg   29520
ctatgccttt tctcctttga aattctgtaa gctttgagtt aaccgcttta taagcttta   29580 taacttttcct ggccatcttc ctcagttttt tcatctcaac aaaatgtgct tcatgtctcc   29640
aaaggccctc ttcgtttcct gacattttat acattttatg aattctaact tgtacctttt   29700
ttttcctagt attcctcgtc tcacaagaaa aatatattga tgataatgag ctcatcaagc   29760
aatctaatta acaccatttg tcttgctttc tgattctagt tctgaactaa ctatattttt   29820
tttgtctctc gtgctgtata tgtaatacta acttttatat ttttttttata gttgcctttc   29880 tcagggtat tactttcttt atgtagctct gaactactca gtaatatcct ttcatgtcag   29940
cctgaaggag tccttctgtt ttccctgtag gcacatcttc tggagacata cttccacaat   30000
ttttaattct ctgtcaattt atttaatttt ttttcccatt gcatgacttt taacgtgtca   30060
tccaactggc ttctggcctc cgttatttct aatgagaaat ctattgataa ttctattaag   30120
catccattat atgcgaagaa tcatgtctgt catactgctt tcaaactcca tcttggtgtc   30180 ttacctttttg ttggttcgac tatgttgtgt ctcctggagt ttatctagtt ggagtgcact   30240
gagcttcttg gttgtagact ttcagggctt tccacaaatt tggaaattgt ttaaccattt   30300
ttgcttcaac tgttctgcct ttttccttct cttttcttac gaaattccca ttctgcatat   30360
atgggtgcac ttgatggtgt tacacaggtc tcttaggatc tgattaatat tcttctcttt   30420
ttaccccctg ctgatttatt tcaattgaca tgtcttagag ttttctgatt ctttcttctg   30480
cctgctcaaa gctcctgttg aaaccatctt gtgagttttt cacttctgct atgggactga   30540
gagcttcaga attttgactt gtttcatttt tgtaattta gtgcctttct tgaaactctt   30600
atttggaggg acattattct cctgatacc attagtcctt tgtgtgttgc ttcttaaggc   30660
atttaagcct gtttgagagt tgatagactt tagtaagtaa gtaagcctgg gctatctgag   30720
```

```
agcttttttc ttttaaccga agggctatac ttctttctttt tttttttttttt gagacggagt    30780
ctcgctctgt cgcccaggct ggagtgcagt ggtgggatct tggctcactg caagctccgc    30840
ctcccgggtt cacgccattc tcctgcctca gcctcccaag tagctgggac tacaggcgcc    30900
cgccactacg cccggctaat ttttttgtatt tttagtagag acggggtttc accgttttag    30960
ccgggatggt ctcgatctcc tgacctcgtg atccgcccgc ctcggcctcc caaagtgctg    31020
ggattacagg cgtgagccac cgcgcccggc cagggctata cttcttttct ttgtatgcct    31080
actaatgttt taaactgaac acttttcaga gtattgcttc aactctgaaa atcgtattat    31140
ccccccttgtc ttctctcaaa aaatttgttg ttgcttttat gtacaatagt tgttgtttgg    31200
ttagtaaatt ttctgaactg gttttttggg gggatatgtt ttaaaggtga aattcacata    31260
acacaaaacg aaccatctta aaccgaacag tttggtctca tttagtacat tcacagtgtt    31320
gtgcaaccac cgtgtctact taattctaaa acatttaat ttctccagaa aagtctcaat    31380
acaatttatt tctcattcat ccctgcttct aaccttggac cacaggttta ctttctgttt    31440
ctatgaattt attctgcgta tttcttataa atggaatcat acaatatgtg atcttttgta    31500
tctgacttct caaagttcat ctgtgctatg gcatgagtca gagttttatt ccttttccat    31560
ggctgaataa tattgcattg tatggacaga tcacattcta cttatccatg ggtctgttaa    31620
agcacatttg tgttgtttcc accactaagc tattgtgaat atttctactg tgaacatctg    31680
tgtgcaaata tttgttcaag ttcttccttt cagagttttg ggtatatacc cagaagtggt    31740
attggacagt catatggtag ttctctgttt caacttttttg aggaacttac tgctttccat    31800
agcagtgtca tagccatttt gcattcttac cagccatgct caagggttct aatatgtctg    31860
cattcttgcc aacactgtta ttttctacct ctttttgtat ggcaagaaat agtatcttgt    31920
gtggcaagaa atagtatctt gtggttttga tttgcatttt cctaacaact aaagatagtg    31980
agcaattctt tgtatacgtg agtaatcttt tagttttatg ttcttttttct gctttctgtt    32040
agcctgttgg tcatctacca acctaacaaa ctctttctta agccaaaaca ataatgataa    32100
taactaataa tagtattaac tacccagtct ttgcagattg tgtctgattg gtgaaacttt    32160
ttcgggggcta ctttaaaaac tattttagac tccaccttct gcttcggaag agcatgaaag    32220
tcagatagag gtgacgttag ggtcttagat cttttctgag catgtatctt gccctggatg    32280
tttaatgtgg ctttctcagt tctcaaatac tacgtggaag cttttttaga atcccttttt    32340
cccaaaatat ctctttctct aggatttgcc tcccaggcac ttaaaattat ctgttgtttt    32400
tctagtctct ctctttctct ctctctctct cctcccacc cccaccaccc cattttaaag    32460
ctggaggtgg ctgtgactaa tacgtttgct tttttatact ttccaaaaac acagcctggg    32520
aagtctcctg tcttctaagc gaactgtcag gcaggtgaaa gaaaatcagg cccttgaggt    32580
agtcctccag gaagccacca gacaagtcaa aacacaccac cttagttctt cgggaaaaag    32640
gttcacatca tggttcctgg caccaatcag ctgcaccagc atctcaggtt gctttcccac    32700
agtagctgct tacataggaa ttggggcaag tgtgtgtatg cagggaactt agtgcattat    32760
agcactcttg taccacaatg taaaagcttt taaaaatcca ttaagtgttc tcctgatttg    32820
ggttttttat tttattttat tttattgcac tgctctgaac atttcagcac tagatcattg    32880
tttgagtaga gggacaaagt tgtggagttt ccaacttcat cattttggt gacttaattc    32940
tatgacttta aaaatttgca tttctttgat tatagaagca aagagtcttt tcacttgttc    33000
gtggacccct ctatatttgt ttttttgaatt acacatattt tgagtacttt tctatgaata    33060
ccacttttaa attcacaatc tcatttttct tttaggacac gtacttgaag atagagcctt    33120
```

```
tccactcttc ctacatctgt tacagcatct agagacatct ttgagttcac atctggccca   33180
ttagttctga cccacacctc tttctgcttt tttctccttt ttaggttgtc cgcacaaacc   33240
agtgtgcagg ggagtttgtc atcacttttc ctcgtgctta ccacagtggt tttaaccaag   33300
gctacaattt tgctgaagct gtcaactttt gtactgctga ctgggtgagt gagcatgcag   33360
tgggcctgca ggtagaaagt ataaagaata tgggtaagga ttattgtgga gaagctatgc   33420
attgtggtct ccagatagcc acacacaatc ttgaacgcac ttgcagctac ctgctggacg   33480
ccagtgcatt gaacactacc gccggctccg gcgctattgt gtcttctccc acgaggagct   33540
catctgcaag atggctgcct tcccagagac gttggatctc aatctagcag tagctgtgca   33600
caaggagatg ttcattatgg ttcaggagga gcgacgtcta cgaaaggccc ttttggagaa   33660
ggtgggtggt caagagcaga gcttagggat ttagtcacat atattacgtt acagagacac   33720
agaccaacat tgagtaacca ctgtgtgcct gatctttaag tcatgcattt tgaaatgtaa   33780
agacagagtc tgtatgtgtt tatatttttt cttccaattt ctctacagct ttccttacaa   33840
ggttgagtcc acatcagggc tcagtgttgg ctgaggtggg gtgtccacaa ccctactcct   33900
agtctttaca gtatatgtgg gttgaacacc cccaggcgt cacggaggct gagcgagagg   33960
cttttgagct gctcccagat gatgaacgcc agtgcatcaa gtgcaagacc acgtgcttct   34020
tgtcagccct ggcctgctac gactgcccag atggccttgt atgcctttcc cacatcaatg   34080
acctctgcaa gtgctctagt agccgacagt acctccggtg agcatgggaa cactgtgggg   34140
acgtgaagga ggttttagag ctgggccaga tgtgtaccct tcccggcttt cttcctctag   34200
gtatcggtac accttggatg agctccccac catgctgcat aaactgaaga ttcgggctga   34260
gtcttttgac acctgggcca acaaagtgcg agtggccttg gaggtggagg atggccgtaa   34320
acgcagtgag tgacaggaaa tggaaggaac ccttgtgtaa gccttatttc tttcttttgg   34380
gtattctcaa ccttccttttt ctgctaacac tgcctacctg ttgcaactta cactctccag   34440
gctttgaaga gctaagggca ctggagtctg aggctcgtga ggaggagtttt cctaatagtg   34500 agctgcttca gcgactgaag aactgcctga gtgaggtgga ggcttgtatt gctcaagtcc   34560
tggggctggt cagtggtcag gtggccaggt acgtgagagg agaaggcaaa gaagggtgtc   34620
agtgtgtgaa aatgaataac aaaaatggat agactataaa cacacaatcc tgtttgaggc   34680
tgaggcagga gaattgtttg aacccaggag acagaggttg cagtgagccg agatggcatc   34740
attgcactcc agcctgggca gcaagagcaa aactccatct caaaacaaca gcaaaaaaaa   34800
agaagcacag actcagattt tactgagaaa gagtagataa cacatggaca aaaagcagta   34860
taatagaaac tagaaattac tgaactaaag tttctaacaa aataatgtgg caataagata   34920
taaatatata ctagcaaaat tgcagttttt tcctacttct taggaaatct catagcgtta   34980
tgcagacatc ggaattcca caaactttac ttttggctgt gtagttaggt aaaacttcag   35040
aggttaaaat aatcctagaa atttatttaa ctgttagttt ccaaatgtgt aagacaatag   35100
atacatatag ttttttagatt gaaaagtaag tgattatgta cagtcaggca tcacttaatg   35160
atggagatgt gttaggagaa aagcgtcatt aggcggtttt gtcattgctg catacgcacc   35220
gtctacttac ataaacctgg atgctgtgac ctcctacaca cctaggctgt gtgatagagc   35280
ctgttgttcc tagcctgcaa acctgcacag cgtgatactg tactgaatat tgttgtcagt   35340
tgtaacactg gtgagtattt gtgtatcaaa atacgcaaat gtagaattac tacaataaaa   35400
gaattgtgga agacataaaa tatggggcac ttaccatgaa tgaaacttgc aagacaggaa   35460
```

```
gtttctctgg gtgaggaacc gactggtaag agaatgtgaa gaccttggac atgactgtac    35520
actactgtag acctaataaa cgctttacac tttggctttg ttaaatttat ataacggtat    35580
cttaaaaaga gatagtaaat tagcctcagc tactgtaaat ttttaaaact tttttttcagg   35640 gtacatgtgc aggtttgtta tataggtaca tttgtgtcat gggggtttgt taaccccatg    35700
tacatagggg ttttatcacc caggtattac attcagtacc ccttagttat ttctcctgat    35760
cctctctctc ctcccacctt ctactcggtg atagtcccca gtatgtgctg ttccctctat    35820
gcgtgcgtcc atgtgttctc atcatttatc ttacacatat tagtgagaac atgtggtatt    35880
tgattttctc ttcctgtgtt agtttgctaa ggataatggc ctccagctcc atccatgttt    35940
cttcaaaggg catgatcctg ttcttgtaat atctgcattg taattccatg gtgtatatgt    36000
accagttttt ctttatccag tctatcatta atggtcattt aggttgattt catgtctttg    36060
cttttgtgaa tggtgctaca gtgaacataa cacgtgcata tgtcttcatg atagaacaat    36120
ttatatacct ttgggtatat acccagtaat gggttagctg ggtcaaacgg tatttctgcc    36180
tctagatctt tgaggaattg ccacactgtc ttccacaatg gttgaactaa ttttacactc    36240
ccgccaaccc tgtatagcag ttacttttc tccgccacct caccaacacc tgctatttcc     36300
tgactttcat aattgccatt ctgacaggtg ttatcaggtg gtacctcact gtggttttgt    36360
tttgcatttc tctaatgatc actgatgctg agcttttttt catatatctg ttggctgcat    36420
gtatgtctcc gtttgaaaag tgtctgttta tgtcctttgc ccactttgta atggggttgt    36480
tttcttcttg taaatttgat taggttcctt tatagatgct ggatattaga cccttgtcag    36540
atgtataatt tgcagaagct ttctcccatt ctgtaggttg tctgtttacc ctgtgtgtag    36600
acagtttctt tgtacaggag ctctttaatt aggactcgtg tcaattttg cttttgccgc     36660 agttgctttt ggcgtctcca ttgtgaaatc tttgcccatg cctgtgtcca gttgtcttcc    36720
agggcattta tggtttcagg ttttaaattt atgtctttaa tccatcttga actgatgttt    36780
gtataaggta catggcaggg gtcctgtttc agttttctgc atatggctca gccagatttc    36840
tcaacaggat atactaatta gggagtcctt tccccattgc ttgttttgt cagctttgtc     36900 aaagatcaga tggttgtagg tacgcatcct catttctggg cttttctatca tgtttcattg    36960 gtctatgagt ctgttttgt aaactgtttt tgtaaacatt taatttctat ttgaatgttt      37020
tactcttttc taataatggt tagcttaaaa cacaaatgca tcatagagtt gtacaaaaat    37080
attttctttc ctcatattgt cattctgtaa acttttctgt gtaaacaatt tttaagtttg    37140
ttttccattt taaacatttt tgttaaaatc taagatgtaa agacacacat tggcctaggc    37200
ctacacagag tcagattctg aatgttacca tcttccccca tctatatctt attttagtgg    37260
aaggtcttca gggcactgac acacgtagaa agggatctgt taagataacc atgccacttc    37320
ctggaatact tcctgaaata cttttgaggc tgcctgacag ttaacttttg tttatagtag    37380
gagtatattc taaaataata gtttagaaaa atgtggtgtc aagcattaac cagtatatgg    37440
ctgtttgtta tcaggtatta tgtgatgcat gtgctagaca gattcttaca tgatggacag    37500
tgcattgggt tgtttatatc agcatcacca cagacacatg aggaatgtgt tgctacttta    37560
caactgctac gatgtcagca ggtgatagga atgtttcagt actgttataa tcttacaggc    37620
ccactatcat acatgtgatt tgtcattgaa atgtcatgtg gtgcatgaca atgttaaatc    37680
atgtatttgt agaaactcta tataaaaaat aataaagctg tgttagtagg aaggaatttt    37740 agataaaacta ctctatttaa aaaaaataaa gctgtgttag taggaaggaa ttttagataa   37800
agaagggatt ttttgtcat taggtttaag ggtcagaata aaggtatcaa gactctaaag     37860
```

```
caagggtata catttgaacc agtttctact tgagaatata agtaattttt tcaaaaaact    37920
ttaagaaaac atagaaagat tttgaagtgg agaagtacat agcagaatgg atatttgaaa    37980
tttattattt tgggcctatt tggaggatgg gtcccacagg atgtggcatg gtctgattta    38040
aattaaataa actgataagg aagcttttta aatagtccat cacataatta ttagcctgag    38100
ctataattga gatgctagat tgccttttg gcttttctgt gccacctaga tattcaatga     38160
cccatgctta cttagcttag tttcttatgt tttgtcttca ttctcatgtc tgtcatattt    38220
tagagacaca ttatttcaaa tattctttt ttttttttg agacggggtc tcactctgtc     38280
accctggctg gagtgcagtg gcacgatctc agctcattgc aagctccacc tcccgggttc    38340
aggccattat cctgcctcag cctcccaagt agctgggtct acaggtgtgt gccaccacac    38400
ctggctaatt ttttgtatt tttagtagag atggggtttc accatgttag ccaggatggt     38460
ttcaatctcc tcaccttgtg atctgcctgc cttggcctcc caaagtgctg ggattacaag    38520
catgagccac cgtgcctggc ccattatttc agtatttcct acttgttctt aaccttttt     38580 ctcattgctg cctctcttta aaacatggaa acttaaaatt ttagaataaa tttcactttt    38640
ctggataact cctttcccta ctgtggttca ggagaaataa ggcttttcca gattgaaccc    38700
atgataccca aataacatgc cctgcatttc cattttaatc tgcctcaagt tttcctcatg    38760
catttaactt cctggcctct tcagttttct ttgtcttgta ggcagttgga accaaagagt    38820
aaatctcaga agttgtcatc ctgtagtact attttgcttc tgacataatg aactctcatt    38880
tcttgtctag aataaattta ttattctgac catacttatc atcacttagc cctccttct     38940 tcgtaatcct cccattgcat ttgtacttca gtttctggct taatagatgt tttgtctcac    39000
tgtgaaagct actacttctg aatcctaatg gctgttttta catctcttcc tcattcttta    39060
actcttaact ggatgactga tgaaaatata acttaaacca tccaggggcc ttttcacatg    39120
tttcttttct cttgccccac ctatttgtat ttatttctgt tcttctgtgg aatggtacta    39180
gccaggtagt accgtggtgg catggtatta gtagccatag tggtagcaga ttaatactgt    39240
taacgttttc tcaggaagct ggactctctg actttgatat ctgtagtctc tattaactgc    39300
tgtcaaacgc ctacgggtgt tttttcaaat cttaacttgt cagtatcgct gaacttagaa    39360
aaaaaccttt gtgggtatta ctgaaatatg aaagggaagg aagtatatta aaagtctcaa    39420
attgtttgaa atgtgacatt acgaggtgtt ccttctggct cctataggat ggacactcca    39480
cagctgacct tgactgaact ccgggtcctt cttgagcaga tgggcagcct gccctgtgcc    39540
atgcatcaga ttggggatgt caaggtaagg aggggcctgg aaaggtggaa ttcttgttaa    39600
cagcaaatac tcaggaagtc tgacatgtca ggaaaacttg agaacctaat tattctaaac    39660
aaccttctca taataacagg ttcttttcctg gaagtggcgg agatatgtgt tcccatacca    39720
tctctgtgtg tacagcatgc aaggaaatat ccttccagac tgaaataatt aaaaactcta    39780
aactgggcct acataagaca ctggctcttg ggaatgggt ggagaggact gattggttgg     39840
ttggttgatt tccctccaga caccagagtc ttagaaagct tactagatgg ataagattgt    39900
attaaagtgg gtttggaaaa agaaatttag gtaattaaag gagaaaaatg tcattctagg    39960
taaacagagg gcctttgtta ttatcagata gatcatgttt taggatgtgg ttgagaataa    40020
gtattaagca ataggaaatg cctataagag aagatgagaa gtggagcaaa tctaggtggt    40080
tgagtattta tgtggctaaa gaatctgcat tttatcctat gtccttgcag gatgtcctgg    40140
aacaggtgga ggcctatcaa gctgaggctc gtgaggctct ggccacactg ccctctagtc    40200
```

```
cagggctatt gcggtccctg ttggagaggg ggcagcagct gggtgtagag gtgcctgaag    40260
cccatcagct tcagcagcag gtggagcagg cgcaatggct agatgaagtg aagcaggccc    40320
tggccccttc tgctcacagg ggctctctgg tcatcatgca ggggcttttg gttatgggtg    40380
ccaagatagc ctccagccct tctgtggaca aggcccgggc tgagctgcaa gaactactga    40440
ccattgcaga gcgctgggaa gaaaaggctc atttctgcct ggaggccagg tggggcgtag    40500
tctctccctg tctgtatctt gactataatc ctcaaagttt tggggtgacc ctaagtattt    40560
ctatggtgac ccttgggcaa cagactccca gttgggcatc tactaaactc taaaggattg    40620
gcatgacata tcatgtactc ccatctatat gacatgtcat gttgatgttt cactgttgta    40680
aaggcaacaa ttgggggaaat gttcttggat gacttagttc tcaggtgaat ggatgcagca    40740
tgtgacttac aagagatcta tagcccccc tgcaatgtta gagagttcct cagtgtggct    40800
tccttacttt gtcatgcaac acttttatt gcttatgttt ttagcaagga aacctaggac    40860
ttagaaaagg ggcatgtata cctgtaacat gtaatgatag attttctcttt ttcaaaaaaa    40920 atttaggcag aagcatccac cagccacatt ggaagccata attcgtgaga cagaaaacat    40980
ccctgttcac ctgcctaaca tccaggctct caaagaagct ctgactaagg cacaagcttg    41040
gattgctgat gtggatgaga tccaagtgag gatcagtatt tctgctttac tgcgtcaggc    41100
cagcagttag aagagagata gatatacttt atagttttta ctcggttggg ttgtgctaga    41160
aagtgaaggt gggaagttgg aggattcctt gaggtacctg agcgtgtcag aataggaacc    41220
aagggaagag aagcatgaat atgggtgtat acctaagcag agactattga tatatagaag    41280
tgtacagagg aagcaggtta caacagagta acttgcatat gtggaatttt tggtctgagc    41340
caattaaagt aggagttctg agagaaaaga gtttctatca cattttttctg ttgcagaaaa    41400 catctccaga ttttcagccc tgggattatg cagtataata cccagtatta cttaggacaa    41460
atttagacac aatattgttg acataattta aataaagttt ctttccccta ttccagaatg    41520
gtgaccacta cccctgtcta gatgacttgg agggcctggt ggctgtgggc cgggacctgc    41580
ctgtggggct ggaagagctg agacagctag agctgcaggt attgacagca cattcctgga    41640
gagagaaggc ctccaagacc tttctcaaga agaattcttg ctacacactg cttgaggtga    41700
ggtctgagac cctgacccac agcctcttct tcatctggcc tggctgctgt gagatggcgc    41760
atataatgag aacatagatt tttttagtgg gcacctggg aggaaggaga gggtgtagtt    41820
ggtgagggaa gcctggtcat ttcctgtatg tctgcctgcc tgcctcaggt gctttgcccg    41880
tgtgcagacg ctggctcaga cagcaccaag cgtagccggt ggatggagaa ggcgctgggg    41940
ttgtaccagt gtgacacaga gctgctgggg ctgtctgcac aggacctcag agacccaggc    42000
tctgtggtaa ggagcatggc ccagatgggg aaaagatggg ttctggtttt ctctctgaaa    42060
agaggagagc tgctgatgat agggtgtctg agccctgtta caggtctcct ggtttgggag    42120
ctgggcatta ggatgccaga caagggcgag ggtggactgc tgacctactt tcccctctt    42180 ctggatatgg cagattgtgg ccttcaagga aggggaacag aaggagaagg agggtatcct    42240
gcagctgcgt cgcaccaact cagccaagcc cagtccactg gcaccatccc tcatggcctc    42300
ttctccgact tctatctgtg tgtgtgggca ggtgccagct ggggtgggag ttctgcagtg    42360
tgacctgtgt caggactggt tccatgggca gtgtgtgtca gtgcccatc tcctcacctc    42420 tccaaagccc agtctcactt catctccact gctagcctgg tgggaatggg acacaaaatt    42480
cctgtgtcca ctgtgtatgc gctcacgacg gccacgccta gagacaatcc tagccttgct    42540
ggttgccctg cagaggctgc ccgtgcggct gcctgagggt gaggcccttc agtgtctcac    42600
```

-continued

```
agagagggcc attggctggc aagaccgtgc cagaaaggct ctggcctctg aagatgtgac   42660
tgctctgttg cgacagctgg ctgagcttcg ccaacagcta caggccaaac ccagaccaga   42720
ggaggcctca gtctacactt cagccactgc ctgtgaccct atcagagaag gcagtggcaa   42780
caatatttct aaggtgagct ttccaggcca gccattgtcc tcatatttct gtcttctagc   42840
ccctgtcctt cttgtagctc cagtcttgtc cctgttcccc agttttcaat ctcctttggc   42900 ctagtcccett tgctccattc tatacctatc cagatccta aactctgatc cctgttggaa   42960
gcctgtgtct actctgcttc aggagataga ggctcccaag ttttggagtt gtgggaggaa   43020
agataggacc tggttcatca gctcaattat tgttacccat tctttttttc cgataggtcc   43080
aagggctgct ggagaatgga cacagtgtga ccagtcctga aacatggct ccaggaaagg   43140 gctctggtaa gacaggtgtg gtttgggtag gctgttggct aaacataact gagtgaccca   43200
tgtatttgtc acctctgttg tggccatgga ggataagacc aagagtggcc tctaacccag   43260
tctgtccctg cacctttcac cgcaccacct tccgcccaga cctggagcta ctgtcctcac   43320
tgttgccgca gttgactggc cctgtgttgg agctgcctga ggcaatccgg ctcccctgg    43380 aggagctcat gatggaaggg gacctgcttg aggtgaccct ggatgagaac cacagcatct   43440
ggcagctgct gcaggctgga cagcctccag acctggacag aattcgcaca cttctggagg   43500
taggaagcgg ggtcacaggc agggcaggag atcaggtcca gcaggcaggg atcccagtac   43560
tgacgttttt cgccttgtgt gggtatgatt gcagctggaa aaatttgaac atcaagggag   43620
tcggacaagg agccgggctc tggagaggcg acggcggcgg cagaaggtgg atcagggtag   43680
aaacgttgag aatcttgttc aacaggagct tcagtcaaaa agggctcgga gctcagggat   43740
tatgtctcag gtgggccgag aagaagaaca ttatcaggag aaagcagacc gtgaaaatat   43800
gttcctgaca ccttccacag accacagccc tttcttgaaa ggaaaccaaa atagcttaca   43860
acacaaggat tcaggctctt cagctgcttg tccttcttta atgcctttgc tacaactctc   43920
ctactctgat gagcaacagt tgtgacagtg gcaccaaagg tcatttgtgg ttgttttttgt  43980 ttgtttgttt cttaaatcct actatctcct ggcctggacc tcagaaggag cttttttgctt  44040 atctataatt tttcactgcc aattttgat atcctctctc ctagagttac tgttaaaagg   44100
ttggttcgta aagtccacac cccgatgctc agaagtgtct tgccagcaac attcctgcta   44160
gcatacagga gtgatttcct aaaccagttt cattctagtc tgaatagga caaacaaatc    44220 ttgaggaagc ccaagtgcgt acctttattt ttgcccccac caccctcttt ctgtacttca   44280 attttttgttt gttttttgtt tttttgtccc tgtcataaaa tattttggtg cttcaaaact   44340
tgtaccttca ttgtacatcc ttttctttc tcccttggg tcttattata aagaagaca    44400 atgtacgttg taattaccaa aaagaatagg gaaaaacaag aatttcatga ctctacctgt   44460
ggtctatctt taatttcatt tcttttgtta aaaataaaac aatgagtatg tttggatact   44520
atgaatatga tttgaacttc ttaaattgta cgagtgaagg actgaggtta ggaaacaaca   44580
gtagcatggg tcaacgtaat ttttaatagt cttttcggg gcagtgggga agggtaaatt    44640
ttacttagaa aacatacatg agacttaggc caaggttaat gttttctcaa aggatgtcca   44700
gttgacccag caccagcaat agaaaactta cctgtcctac acttaattgc tttgtgcttt   44760
ttattgaaaa tctgttggct ggacttgcat gtgccaatat ctgagttaac ttgttgcatt   44820
gcatcattta actatgtgtc tgtccccctgt ggccagatca caatgtcttg gttacagtcg   44880
ctttataata agtcttacat cagggtagac agattcatct cacttttttg tttttcagat   44940
```

```
tgttttagca agttaagtca ccagctctct ttttcattat gtagtagctt ttgtgtccta    45000
aatctgatta agttgcactg acacaagtta tctccctcaa tattttctgt tctttcaact    45060
ggtgaataca atagctaatc taaatcattt gttgtaagaa ttcagtagga ttgatgtgta    45120
aatatttcag gtaaaccac tctattagta taccactaat tcaattcacg gttcttgttt     45180
tgtgtgtctc tgggtgatct aataatacag actgtattat acttctttta atccctttaa    45240
aggtgaacgc attctgtcat cctggattga atctctcgct tttccaccta ctccttgctg    45300
acttgagtca gtgtagaaca cgttattacc catagcattt ctcatgccta taatcatacc    45360
taccttcctt attgtctact cttttcacct ctttctttct ttgatactgt catagggaac    45420
tataattagc tttcccagta acaaagctat gcttggtgat gacctagtag agtagaaatt    45480
gcttcacctg tccaagtaca gtgtacttta ccttaccaca ccatagggac caggtaaaat    45540
atatagaaaa tcctgagata atttatctaa atctgagaat tgtcttcgaa atttcttttt    45600
tctcctcttc cataaatagg aggaaagtca tgattctcaa gccattacag attctctgac    45660
acttgttaac ggaaaattct gatgaggcat gatgagaact tctgcctata aaatctcac     45720 taaagttctg agtcacaaat tgttcacata cttcacagta agcaggcaat ccaatgtcag    45780
gacagttgta cacctttctt aggttgcctc ccctaattgg ggctgtattt gacatgaggg    45840
gccagttttg acactttta aaaccataca caaggatgca gcactaagtt tttgcacata     45900
ggcaagaatt tatcttgtga ttagaagtta gttatatgtt cattaagaaa catgacgaaa    45960
tctgcagcaa aaattgaatt tcataggcca ttcagtgttc tctgcgataa ttctaattca    46020
gaaaaaaatt gaatcttggt ttaaaaaaat tgtaataaaa ctttaccact ggtaagccag    46080
ctgtcttggt ctcttctgct gtgagaaaaa aatatatcag actgggcaat ttataaactt    46140
aaatatattg ctcacagttc acgttgtaaa catacacagc ataaacttct ggagggacct    46200
gcgccatacc tgggcccatt tcagccacag ctaatagagc caaggagtgc tgcaccagaa    46260
tttcggaaat caaggtttag ggtggtactg tgcagtgagc cccacgtcca agggcacttt    46320
gggcctcccc tttaaaactg tcaactttca agaccctaac taacactctg ggcctgtgat    46380
gggtatgaca tcaaagaact ccaaaatatt ttatggtaat tcttgttagg atgaatacca    46440
tctgactccc ttatgtctgc taatcttaac aaaatgttcc catggacaca cgcctatttt    46500
ctcctgaaca cgcttttca ttctt                                           46525
```

<210> SEQ ID NO 2
<211> LENGTH: 5595
<212> TYPE: DNA
<213> ORGANISM: Homo sapiens

<400> SEQUENCE: 2

```
cattttaaaa aagatccggc catactattt ttatcttgct ttttcgttct gtcgcagtac      60
tgtttaatat gagtccagcg acggctctgt gactgttttc ctctggtaaa atcgctcttg     120
cgtcctcagc gtttatctca ggtgcggaag gtctcacagg tttggaaata gcgccggaaa    180
aatcgatccg cggagtgaga cggctcgtac cacactgcag ggcccggagg tcaagatggt    240
ggctgtaaaa ctaggatccc tgacgattgc ttagcattaa ggcccgacat ggaaccgggg    300
tgtgacgagt tcctgccgcc accggagtgc ccggtttttg agcctagctg ggctgaattc    360
caagacccgc ttggctacat tgcgaaaata aggcccatag cagagaagtc tggcatctgc    420
aaaatccgcc caccgcgga ttggcagcct ccttttgcag tagaagttga caatttcaga     480
tttactcctc gcgtccaaag gctaaatgaa ctggaggccc aaactagagt gaaattgaac    540
```

-continued

```
tatttggatc agattgcaaa attctgggaa attcaaggct cctctttaaa gattcccaat      600
gtggagcgga agatcttgga cctctacagc cttagtaaga ttgtgattga ggaaggtggc      660
tatgaagcca tctgcaagga tcgtcggtgg gctcgagttg cccagcgtct ccactaccca      720
ccaggcaaaa acattggctc cctgctacga tcacattacg aacgcattat ttaccccta t     780 gaaatgtttc agtctggagc caaccatgtg caatgtaaca cacaccgtt tgacaatgag       840 gtaaaagata aggaatacaa gccccacagc atccccctta gacagtctgt gcagccttca      900
aagttcagca gctacagtcg acgggcaaaa aggctacagc ctgatccaga gcctacagag      960
gaggacattg agaagcatcc agagctaaag aagttacaga tatatgggcc aggtcccaaa      1020
atgatgggct tgggccttat ggctaaggat aaggataaga ctgtgcataa gaaagtcaca      1080
tgccccccaa ctgttacggt gaaggatgag caaagtggag gtgggaacgt gtcatcaaca      1140
ttgctcaagc agcacttgag cctagagccc tgcactaaga caaccatgca acttcgaaag      1200
aatcacagca gtgcccagtt tattgactca tatatttgcc aagtatgctc ccgtggggat      1260
gaagatgata agcttctttt ctgtgatggc tgtgatgaca attaccacat cttctgcttg      1320
ttaccacccc ttcctgaaat ccccagaggc atctggaggt gcccaaaatg tatcttggcg      1380
gagtgtaaac agcctcctga agcttttgga tttgaacagg ctacccagga gtacagtttg      1440
cagagttttg gtgaaatggc tgattccttc aagtccgact acttcaacat gcctgtacat      1500
atggtgccta cagaacttgt agagaaggaa ttctggaggc tggtgagcag cattgaggaa      1560
gacgtgacag ttgaatatgg agctgatatt cattccaaag aatttggcag tggctttcct      1620
gtcagcaata gcaaacaaaa cttatctcct gaggagaaga gacaaagtct cactgtgttg      1680
accaggctga tctcaagctt ctgggctcaa gcagtcctcc caccttggcc tcccaaagtg      1740
ttgggattac aggagtatgc gaccagtggt tggaacctga atgtgatgcc agtgctagat      1800
cagtctgttc tctgtcacat caatgcagac atctcaggca tgaaggtgcc ctggctgtac      1860
gtgggcatgg ttttctcagc attttgttgg catattgagg atcactggag ttactctatt      1920
aactatctgc attggggtga gccgaagacc tggtatggtg taccctccct ggcagcagag      1980
catttggagg aggtgatgaa gatgctgaca cctgagctgt tgatagcca gcctgatctc      2040 ctacaccagc ttgtcactct catgaatccc aacactttga tgtcccatgg tgtgccagtt      2100
gtccgcacaa accagtgtgc agggagtttt gtcatcactt ttcctcgtgc ttaccacagt      2160 ggtttttaacc aaggctacaa ttttgctgaa gctgtcaact tttgtactgc tgactggcta      2220
cctgctggac gccagtgcat tgaacactac cgccggctcc ggcgctattg tgtcttctcc      2280
cacgaggagc tcatctgcaa gatggctgcc ttcccagaga cgttggatct caatctagca      2340
gtagctgtgc acaaggagat gttcattatg gttcaggagg agcgacgtct acgaaaggcc      2400
cttttggaga agggcgtcac ggaggctgag cgagaggctt ttgagctgct cccagatgat      2460
gaacgccagt gcatcaagtg caagaccacg tgcttcttgt cagccctggc ctgctacgac      2520
tgcccagatg gccttgtatg cctttcccac atcaatgacc tctgcaagtg ctctagtagc      2580
cgacagtacc tccggtatcg gtacaccttg gatgagctcc ccaccatgct gcataaactg      2640
aagattcggg ctgagtcttt tgacacctgg gccaacaaag tgcgagtggc cttggaggtg      2700
gaggatggcc gtaaacgcag ctttgaagag ctaagggcac tggagtctga ggctcgtgag      2760
aggaggtttc ctaatagtga gctgcttcag cgactgaaga actgcctgag tgaggtggag      2820
gcttgtattg ctcaagtcct ggggctggtc agtggtcagg tggccaggat ggacactcca      2880
```

```
cagctgacct tgactgaact ccgggtcctt cttgagcaga tgggcagcct gccctgtgcc    2940
atgcatcaga ttggggatgt caaggatgtc ctggaacagg tggaggccta tcaagctgag    3000
gctcgtgagg ctctggccac actgccctct agtccagggc tattgcggtc cctgttggag    3060 aggggggcagc agctgggtgt agaggtgcct gaagcccatc agcttcagca gcaggtggag    3120
caggcgcaat ggctagatga agtgaagcag gccctggccc cttctgctca cagggctct    3180 ctggtcatca tgcaggggct tttggttatg ggtgccaaga tagcctccag cccttctgtg    3240
gacaaggccc gggctgagct gcaagaacta ctgaccattg cagagcgctg ggaagaaaag    3300
gctcatttct gcctggaggc caggcagaag catccaccag ccacattgga agccataatt    3360
cgtgagacag aaaacatccc tgttcacctg cctaacatcc aggctctcaa agaagctctg    3420
actaaggcac aagcttggat tgctgatgtg atgagatcc aaaatggtga ccactacccc    3480
tgtctagatg acttggaggg cctggtggct gtgggccggg acctgcctgt ggggctggaa    3540
gagctgagac agctagagct gcaggtattg acagcacatt cctggagaga gaaggcctcc    3600
aagacctttc tcaagaagaa ttcttgctac acactgcttg aggtgctttg cccgtgtgca    3660
gacgctggct cagacagcac caagcgtagc cggtggatgg agaaggcgct ggggttgtac    3720
cagtgtgaca cagagctgct ggggctgtct gcacaggacc tcagagaccc aggctctgtg    3780
attgtggcct tcaaggaagg ggaacagaag gagaaggagg gtatcctgca gctgcgtcgc    3840
accaactcag ccaagcccag tccactggca ccatccctca tggcctcttc tccgacttct    3900
atctgtgtgt gtgggcaggt gccagctggg gtgggagttc tgcagtgtga cctgtgtcag    3960
gactggttcc atgggcagtg tgtgtcagtg ccccatctcc tcacctctcc aaagcccagt    4020
ctcacttcat ctccactgct agcctggtgg gaatgggaca caaaattcct gtgtccactg    4080
tgtatgcgct cacgacggcc acgcctagag acaatcctag ccttgctggt tgccctgcag    4140
aggctgcccg tgcggctgcc tgagggtgag gcccttcagt gtctcacaga gagggccatt    4200
ggctggcaag accgtgccag aaaggctctg gcctctgaag atgtgactgc tctgttgcga    4260
cagctggctg agcttcgcca acagctacag gccaaaccca gaccagagga ggcctcagtc    4320
tacacttcag ccactgcctg tgaccctatc agagaaggca gtggcaacaa tatttctaag    4380
gtccaagggc tgctggagaa tggagacagt gtgaccagtc ctgagaacat ggctccagga    4440
aagggctctg acctggagct actgtcctca ctgttgccgc agttgactgg ccctgtgttg    4500
gagctgcctg aggcaatccg ggctcccctg gaggagctca tgatggaagg ggacctgctt    4560
gaggtgaccc tggatgagaa ccacagcatc tggcagctgc tgcaggctgg acagcctcca    4620
gacctggaca gaattcgcac acttctggag ctggaaaaat ttgaacatca agggagtcgg    4680
acaaggagcc gggctctgga gaggcgacgg cggcggcaga aggtggatca gggtagaaac    4740
gttgagaatc ttgttcaaca ggagcttcag tcaaaaaggg ctcggagctc agggattatg    4800
tctcaggtgg gccgagaaga agaacattat caggagaaag cagaccgtga aaatatgttc    4860
ctgacacctt ccacagacca cagcccttc ttgaaaggaa accaaaatag cttacaacac    4920
aaggattcag gctcttcagc tgcttgtcct tctttaatgc ctttgctaca actctcctac    4980
tctgatgagc aacagttgtg acagtggcac caaaggtcat tgtggttgt ttttgtttgt    5040 ttgtttctta aatcctacta tctcctggcc tggacctcag aaggagcttt tgcttatct    5100 ataatttttc actgccaatt tttgatatcc tctctcctag agttactgtt aaaaggttgg    5160
ttcgtaaagt ccacacccg atgctcagaa gtgtcttgcc agcaacattc ctgctagcat    5220
acaggagtga tttcctaaac cagtttcatt ctagtctgaa tagggacaaa caaatcttga    5280
```

```
ggaagcccaa gtgcgtacct ttattttttgc ccccaccacc ctctttctgt acttcaattt    5340
ttgtttgttt tttgttttttt tgtccctgtc ataaaatatt ttggtgcttc aaaacttgta    5400
ccttcattgt acatccttt cttttctccc cttgggtctt attataaaag aagacaatgt     5460
acgttgtaat taccaaaaag aatagggaaa aacaagaatt tcatgactct acctgtggtc    5520
tatctttaat ttcatttctt ttgttaaaaa taaaacaatg agtatgtttg gatactatga    5580
aaaaaaaaaa aaaaa                                                      5595

<210> SEQ ID NO 3
<211> LENGTH: 5502
<212> TYPE: DNA
<213> ORGANISM: Homo sapiens

<400> SEQUENCE: 3
cattttaaaa aagatccggc catactattt ttatcttgct ttttcgttct gtcgcagtac      60
tgtttaatat gagtccagcg acggctctgt gactgttttc ctctggtaaa atcgctcttg    120
cgtcctcagc gtttatctca ggtgcggaag gtctcacagg tttggaaata gcgccggaaa    180
aatcgatccg cggagtgaga cggctcgtac cacactgcag ggcccggagg tcaagatggt    240
ggctgtaaaa ctaggatccc tgacgattgc ttagcattaa ggcccgacat ggaaccgggg    300
tgtgacgagt tcctgccgcc accggagtgc ccggtttttg agcctagctg ggctgaattc    360
caagacccgc ttggctacat tgcgaaaata aggcccatag cagagaagtc tggcatctgc    420
aaaatccgcc cacccgcgga ttggcagcct ccttttgcag tagaagttga caatttcaga    480
tttactcctc gcgtccaaag gctaaatgaa ctggaggccc aaactagagt gaaattgaac    540
tatttggatc agattgcaaa attctgggaa attcaaggct cctcttttaaa gattcccaat    600 gtggagcgga agatcttgga cctctacagc cttagtaaga ttgtgattga ggaaggtggc    660
tatgaagcca tctgcaagga tcgtcggtgg gctcgagttg cccagcgtct ccactaccca    720
ccaggcaaaa acattggctc cctgctacga tcacattacg aacgcattat ttacccctat    780
gaaatgtttc agtctggagc caaccatgtg caatgtaaca cacacccgtt tgacaatgag    840
gtaaaagata aggaatacaa gccccacagc atccccctta gacagtctgt gcagccttca    900
aagttcagca gctacagtcg acgggcaaaa aggctacagc ctgatccaga gcctacagag    960
gaggacattg agaagcatcc agagctaaag aagttacaga tatatgggcc aggtcccaaa   1020
atgatgggct tgggccttat ggctaaggat aaggataaga ctgtgcataa gaaagtcaca   1080 tgcccccaa ctgttacggt gaaggatgag caaagtggag gtgggaacgt gtcatcaaca   1140
ttgctcaagc agcacttgag cctagagccc tgcactaaga caaccatgca acttcgaaag   1200
aatcacagca gtgcccagtt tattgactca tatatttgcc aagtatgctc ccgtggggat   1260
gaagatgata agcttctttt ctgtgatggc tgtgatgaca attaccacat cttctgcttg   1320
ttaccacccc ttcctgaaat ccccagaggc atctggaggt gcccaaaatg tatcttggcg   1380
gagtgtaaac agcctcctga agcttttgga tttgaacagg ctacccagga gtacagtttg   1440
cagagttttg gtgaaatggc tgattccttc aagtccgact acttcaacat gcctgtacat   1500
atggtgccta cagaacttgt agagaaggaa ttctggaggc tggtgagcag cattgaggaa   1560
gacgtgacag ttgaatatgg agctgatatt cattccaaag aatttggcag tggcttttcct   1620 gtcagcaata gcaaacaaaa cttatctcct gaggagaagg agtatgcgac cagtggttgg   1680
aacctgaatg tgatgccagt gctagatcag tctgttctct gtcacatcaa tgcagacatc   1740
```

```
tcaggcatga aggtgccctg gctgtacgtg ggcatggttt tctcagcatt ttgttggcat    1800
attgaggatc actggagtta ctctattaac tatctgcatt ggggtgagcc gaagacctgg    1860
tatggtgtac cctccctggc agcagagcat ttggaggagg tgatgaagat gctgacacct    1920
gagctgtttg atagccagcc tgatctccta caccagcttg tcactctcat gaatcccaac    1980
actttgatgt cccatggtgt gccagttgtc cgcacaaacc agtgtgcagg ggagtttgtc    2040
atcactttc ctcgtgctta ccacagtggt tttaaccaag ctacaatttt tgctgaagct    2100
gtcaacttt gtactgctga ctggctacct gctggacgcc agtgcattga acactaccgc    2160
cggctccggc gctattgtgt cttctcccac gaggagctca tctgcaagat ggctgccttc    2220
ccagagacgt tggatctcaa tctagcagta gctgtgcaca aggagatgtt cattatggtt    2280
caggaggagc gacgtctacg aaaggccctt ttggagaagg gcgtcacgga ggctgagcga    2340
gaggcttttg agctgctccc agatgatgaa cgccagtgca tcaagtgcaa gaccacgtgc    2400
ttcttgtcag ccctgcctg ctacgactgc ccagatggcc ttgtatgcct ttcccacatc    2460
aatgacctct gcaagtgctc tagtagccga cagtacctcc ggtatcggta cacccttggat    2520
gagctcccca ccatgctgca taaactgaag attcgggctg agtcttttga cacctgggcc    2580
aacaaagtgc gagtggcctt ggaggtggag gatggccgta acgcagctt tgaagagcta    2640
agggcactgg agtctgaggc tcgtgagagg aggtttccta atagtgagct gcttcagcga    2700
ctgaagaact gcctgagtga ggtggaggct tgtattgctc aagtcctggg gctggtcagt    2760
ggtcaggtgg ccaggatgga cactccacag ctgaccttga ctgaactccg ggtccttctt    2820
gagcagatgg gcagcctgcc ctgtgccatg catcagattg gggatgtcaa ggatgtcctg    2880
gaacaggtgg aggcctatca agctgaggct cgtgaggctc tggccacact gccctctagt    2940
ccagggctat tgcggtccct gttggagagg gggcagcagc tgggtgtaga ggtgcctgaa    3000
gcccatcagc ttcagcagca ggtggagcag cgcaatggc tagatgaagt gaagcaggcc    3060
ctggcccctt ctgctcacag gggctctctg gtcatcatgc aggggctttt ggttatgggt    3120
gccaagatag cctccagccc ttctgtggac aaggcccggg ctgagctgca agaactactg    3180
accattgcag agcgctggga agaaaaggct catttctgcc tggaggccag gcagaagcat    3240
ccaccagcca cattggaagc cataattcgt gagacagaaa acatccctgt tcacctgcct    3300
aacatccagg ctctcaaaga agctctgact aaggcacaag cttggattgc tgatgtggat    3360
gagatccaaa atggtgacca ctaccctgt ctagatgact tggagggcct ggtggctgtg    3420
ggccgggacc tgcctgtggg gctggaagag ctgagacagc tagagctgca ggtattgaca    3480
gcacattcct ggagagagaa ggcctccaag acctttctca agaagaattc ttgctacaca    3540
ctgcttgagg tgcttttgccc gtgtgcagac gctggctcag acagcaccaa gcgtagccgg    3600
tggatggaga aggcgctggg gttgtaccag tgtgacacag agctgctggg gctgtctgca    3660
caggacctca gagacccagg ctctgtgatt gtggccttca aggaagggga acagaaggag    3720
aaggagggta tcctgcagct gcgtcgcacc aactcagcca agcccagtcc actggcacca    3780
tccctcatgg cctcttctcc gacttctatc tgtgtgtgtg ggcaggtgcc agctggggtg    3840
ggagttctgc agtgtgacct gtgtcaggac tggttccatg ggcagtgtgt gtcagtgccc    3900
catctcctca cctctccaaa gcccagtctc acttcatctc cactgctagc ctggtgggaa    3960
tgggacacaa aattcctgtg tccactgtgt atgcgctcac gacggccacg cctagagaca    4020
atcctagcct tgctggttgc cctgcagagg ctgcccgtgc ggctgcctga gggtgaggcc    4080
cttcagtgtc tcacagagag ggccattggc tggcaagacc gtgccagaaa ggctctggcc    4140
```

```
tctgaagatg tgactgctct gttgcgacag ctggctgagc ttcgccaaca gctacaggcc    4200
aaacccagac cagaggaggc ctcagtctac acttcagcca ctgcctgtga ccctatcaga    4260
gaaggcagtg gcaacaatat ttctaaggtc caagggctgc tggagaatgg agacagtgtg    4320
accagtcctg agaacatggc tccaggaaag ggctctgacc tggagctact gtcctcactg    4380
ttgccgcagt tgactggccc tgtgttggag ctgcctgagg caatccgggc tcccctggag    4440
gagctcatga tggaagggga cctgcttgag gtgaccctgg atgagaacca cagcatctgg    4500
cagctgctgc aggctggaca gcctccagac ctggacagaa ttcgcacact tctggagctg    4560
gaaaaatttg aacatcaagg gagtcggaca aggagccggg ctctggagag cgacggcgg    4620 cggcagaagg tggatcaggg tagaaacgtt gagaatcttg ttcaacagga gcttcagtca    4680 aaagggctc ggagctcagg gattatgtct caggtgggcc gagaagaaga acattatcag    4740
gagaaagcag accgtgaaaa tatgttcctg acaccttcca cagaccacag cccttcttg    4800 aaaggaaacc aaaatagctt acaacacaag gattcaggct cttcagctgc ttgtccttct    4860
ttaatgcctt tgctacaact ctcctactct gatgagcaac agttgtgaca gtggcaccaa    4920
aggtcatttg tggttgtttt tgtttgtttg tttcttaaat cctactatct cctgcctgg    4980 acctcagaag gagcttttg cttatctata attttcact gccaattttt gatatcctct    5040
ctcctagagt tactgttaaa aggttggttc gtaaagtcca cacccgatg ctcagaagtg    5100 tcttgccagc aacattcctg ctagcataca ggagtgattt cctaaaccag tttcattcta    5160
gtctgaatag ggacaaacaa atcttgagga agcccaagtg cgtaccttta tttttgcccc    5220
caccacccct tttctgtact tcaattttg tttgtttttt gttttttgt ccctgtcata    5280 aaatattttg gtgcttcaaa acttgtacct tcattgtaca tccttttctt ttctcccctt    5340
gggtcttatt ataaaagaag acaatgtacg ttgtaattac caaaaagaat agggaaaaac    5400
aagaatttca tgactctacc tgtggtctat ctttaatttc atttcttttg ttaaaaataa    5460
aacaatgagt atgtttggat actatgaaaa aaaaaaaaaa aa                       5502

<210> SEQ ID NO 4
<211> LENGTH: 5331
<212> TYPE: DNA
<213> ORGANISM: Homo sapiens

<400> SEQUENCE: 4
cattttaaaa aagatccggc catactattt ttatcttgct ttttcgttct gtcgcagtac      60
tgtttaatat gagtccagcg acggctctgt gactgttttc ctctggtaaa atcgctcttg     120
cgtcctcagc gtttatctca ggtgcggaag gtctcacagg tttggaaata gcgccggaaa     180
aatcgatccg cggagtgaga cggctcgtac cacactgcag ggcccggagg tcaagatggt     240
ggctgtaaaa ctaggatccc tgacgattgc ttagcattaa ggcccgacat ggaaccgggg     300
tgtgacgagt cctgccgcc accggagtgc ccggttttg agcctagctg ggctgaattc     360
caagacccgc ttggctacat tgcgaaaata aggcccatag cagagaagtc tggcatctgc     420
aaaatccgcc cacccgcgga ttggcagcct ccttttgcag tagaagttga caatttcaga     480
tttactcctc gcgtccaaag gctaaatgaa ctggaggccc aaactagagt gaaattgaac     540
tatttggatc agattgcaaa attctgggaa attcaaggct cctcttttaaa gattcccaat     600 gtggagcgga agatcttgga cctctacagc cttagtaagc aatgtaacac acacccgttt     660
gacaatgagg taaaagataa ggaatacaag ccccacagca tccccttag acagtctgtg     720
```

| | |
|---|---|
| cagccttcaa agttcagcag ctacagtcga cgggcaaaaa ggctacagcc tgatccagag | 780 |
| cctacagagg aggacattga gaagcatcca gagctaaaga agttacagat atatgggcca | 840 |
| ggtcccaaaa tgatgggctt gggccttatg gctaaggata aggataagac tgtgcataag | 900 |
| aaagtcacat gccccccaac tgttacggtg aaggatgagc aaagtggagg tgggaacgtg | 960 |
| tcatcaacat tgctcaagca gcacttgagc ctagagccct gcactaagac aaccatgcaa | 1020 |
| cttcgaaaga atcacagcag tgcccagttt attgactcat atatttgcca agtatgctcc | 1080 |
| cgtggggatg aagatgataa gcttcttttc tgtgatggct gtgatgacaa ttaccacatc | 1140 |
| ttctgcttgt taccacccct tcctgaaatc cccagaggca tctggaggtg cccaaaatgt | 1200 |
| atcttggcgg agtgtaaaca gcctcctgaa gcttttggat ttgaacaggc tacccaggag | 1260 |
| tacagtttgc agagttttgg tgaaatggct gattccttca agtccgacta cttcaacatg | 1320 |
| cctgtacata tggtgcctac agaacttgta gagaaggaat tctggaggct ggtgagcagc | 1380 |
| attgaggaag acgtgacagt tgaatatgga gctgatattc attccaaaga atttggcagt | 1440 |
| ggctttcctg tcagcaatag caaacaaaac ttatctcctg aggagaagga gtatgcgacc | 1500 |
| agtggttgga acctgaatgt gatgccagtg ctagatcagt ctgttctctg tcacatcaat | 1560 |
| gcagacatct caggcatgaa ggtgccctgg ctgtacgtgg gcatggtttt ctcagcattt | 1620 |
| tgttggcata ttgaggatca ctggagttac tctattaact atctgcattg gggtgagccg | 1680 |
| aagacctggt atggtgtacc ctccctggca gcagagcatt tggaggaggt gatgaagatg | 1740 |
| ctgacacctg agctgtttga tagccagcct gatctcctac accagcttgt cactctcatg | 1800 |
| aatcccaaca ctttgatgtc ccatggtgtg ccagttgtcc gcacaaacca gtgtgcaggg | 1860 |
| gagtttgtca tcacttttcc tcgtgcttac cacagtggtt ttaaccaagg ctacaatttt | 1920 |
| gctgaagctg tcaacttttg tactgctgac tggctacctg ctggacgcca gtgcattgaa | 1980 |
| cactaccgcc ggctccggcg ctattgtgtc ttctcccacg aggagctcat ctgcaagatg | 2040 |
| gctgccttcc cagagacgtt ggatctcaat ctagcagtag ctgtgcacaa ggagatgttc | 2100 |
| attatggttc aggaggagcg acgtctacga aaggcccttt tggagaaggg cgtcacggag | 2160 |
| gctgagcgag aggcttttga gctgctccca gatgatgaac gccagtgcat caagtgcaag | 2220 |
| accacgtgct tcttgtcagc cctggcctgc tacgactgcc cagatggcct tgtatgcctt | 2280 |
| tcccacatca tgaccctctg caagtgctct agtagccgac agtacctccg gtatcggtac | 2340 |
| accttggatg agctccccac catgctgcat aaaactgaaga ttcgggctga gtcttttgac | 2400 |
| acctgggcca caaagtgcg agtggccttg gaggtggagg atggccgtaa acgcagcttt | 2460 |
| gaagagctaa gggcactgga gtctgaggct cgtgagagga ggtttcctaa tagtgagctg | 2520 |
| cttcagcgac tgaagaactg cctgagtgag gtggaggctt gtattgctca agtcctgggg | 2580 |
| ctggtcagtg gtcaggtggc caggatggac actccacagc tgaccttgac tgaactccgg | 2640 |
| gtccttcttg agcagatggg cagcctgccc tgtgccatgc atcagattgg ggatgtcaag | 2700 |
| gatgtcctgg aacaggtgga ggcctatcaa gctgaggctc gtgaggctct ggccacactg | 2760 |
| ccctctagtc cagggctatt gcggtccctg ttggagaggg ggcagcagct gggtgtagag | 2820 |
| gtgcctgaag cccatcagct tcagcagcag gtggagcagg cgcaatggct agatgaagtg | 2880 |
| aagcaggccc tggccccttc tgctcacagg ggctctctgg tcatcatgca ggggcttttg | 2940 |
| gttatgggtg ccaagatagc ctccagccct tctgtggaca aggcccgggc tgagctgcaa | 3000 |
| gaactactga ccattgcaga gcgctgggaa gaaaaggctc atttctgcct ggaggccagg | 3060 |
| cagaagcatc caccagccac attggaagcc ataattcgtg agacagaaaa catccctgtt | 3120 |

```
cacctgccta acatccaggc tctcaaagaa gctctgacta aggcacaagc ttggattgct    3180
gatgtggatg agatccaaaa tggtgaccac taccoctgtc tagatgactt ggagggcctg    3240
gtggctgtgg gccgggacct gcctgtgggg ctggaagagc tgagacagct agagctgcag    3300
gtattgacag cacattcctg gagagagaag gcctccaaga cctttctcaa gaagaattct    3360
tgctacacac tgcttgaggt gctttgcccg tgtgcagacg ctggctcaga cagcaccaag    3420
cgtagccggt ggatggagaa ggcgctgggg ttgtaccagt gtgacacaga gctgctgggg    3480
ctgtctgcac aggacctcag agacccaggc tctgtgattg tggccttcaa ggaaggggaa    3540
cagaaggaga aggagggtat cctgcagctg cgtcgcacca actcagccaa gcccagtcca    3600
ctggcaccat ccctcatggc ctcttctccg acttctatct gtgtgtgtgg gcaggtgcca    3660
gctggggtgg gagttctgca gtgtgacctg tgtcaggact ggttccatgg gcagtgtgtg    3720
tcagtgcccc atctcctcac ctctccaaag cccagtctca cttcatctcc actgctagcc    3780
tggtgggaat gggacacaaa attcctgtgt ccactgtgta tgcgctcacg acggccacgc    3840
ctagagacaa tcctagcctt gctggttgcc ctgcagaggc tgcccgtgcg gctgcctgag    3900
ggtgaggccc ttcagtgtct cacagagagg gccattggct ggcaagaccg tgccagaaag    3960
gctctggcct ctgaagatgt gactgctctg ttgcgacagc tggctgagct tcgccaacag    4020
ctacaggcca aacccagacc agaggaggcc tcagtctaca cttcagccac tgcctgtgac    4080
cctatcagag aaggcagtgg caacaatatt tctaaggtcc aagggctgct ggagaatgga    4140
gacagtgtga ccagtcctga aacatggctc caggaaaagg gctctgacct ggagctactg    4200
tcctcactgt tgccgcagtt gactggccct gtgttggagc tgcctgaggc aatccgggct    4260
ccoctgagg agctcatgat ggaagggac ctgcttgagg tgaccctgga tgagaaccac    4320
agcatctggc agctgctgca ggctggacag cctccagacc tggacagaat cgcacactt    4380
ctggagctgg aaaaatttga acatcaaggg agtcggacaa ggagccgggc tctggagagg    4440
cgacggcggc ggcagaaggt ggatcagggt agaaacgttg agaatcttgt tcaacaggag    4500
cttcagtcaa aaagggctcg gagctcaggg attatgtctc aggtgggccg agaagaagaa    4560
cattatcagg agaaagcaga ccgtgaaaat atgttcctga caccttccac agaccacagc    4620
cctttcttga aaggaaaacca aaatagctta caacacaagg attcaggctc ttcagctgct    4680
tgtccttctt taatgccttt gctacaactc tcctactctg atgagcaaca gttgtgacag    4740
tggcaccaaa ggtcatttgt ggttgttttt gtttgtttgt ttcttaaatc ctactatctc    4800
ctggcctgga cctcagaagg agcttttgc ttatctataa ttttttcactg ccaattttg    4860
atatcctctc tcctagagtt actgttaaaa ggttggttcg taaagtccac accccgatgc    4920
tcagaagtgt cttgccagca acattcctgc tagcatacag gagtgatttc ctaaaccagt    4980
ttcattctag tctgaatagg acaaacaaa tcttgaggaa gcccaagtgc gtacctttat    5040
ttttgccccc accaccctct ttctgtactt caatttttgt ttgttttttg ttttttgtc    5100
cctgtcataa aatattttgg tgcttcaaaa cttgtaccttt cattgtacat ccttttcttt    5160
tctccccttg ggtcttatta taaagaaga caatgtacgt tgtaattacc aaaaagaata    5220
gggaaaaaca agaatttcat gactctacct gtggtctatc tttaatttca tttctttgt    5280
taaaaataaa acaatgagta tgtttggata ctatgaaaaa aaaaaaaaaa a           5331
```

<210> SEQ ID NO 5
<211> LENGTH: 20
<212> TYPE: DNA

```
<213> ORGANISM: Homo sapiens

<400> SEQUENCE: 5
cgcagctttg aagagctaag                                               20

<210> SEQ ID NO 6
<211> LENGTH: 20
<212> TYPE: DNA
<213> ORGANISM: Homo sapiens

<400> SEQUENCE: 6
cagctgtgga gtgtccatcc                                               20

<210> SEQ ID NO 7
<211> LENGTH: 1570
<212> TYPE: PRT
<213> ORGANISM: Homo sapiens

<400> SEQUENCE: 7
```

Met Glu Pro Gly Cys Asp Glu Phe Leu Pro Pro Glu Cys Pro Val
1               5                   10                  15

Phe Glu Pro Ser Trp Ala Glu Phe Gln Asp Pro Leu Gly Tyr Ile Ala
            20                  25                  30

Lys Ile Arg Pro Ile Ala Glu Lys Ser Gly Ile Cys Lys Ile Arg Pro
        35                  40                  45

Pro Ala Asp Trp Gln Pro Pro Phe Ala Val Glu Val Asp Asn Phe Arg
    50                  55                  60

Phe Thr Pro Arg Val Gln Arg Leu Asn Glu Leu Glu Ala Gln Thr Arg
65                  70                  75                  80

Val Lys Leu Asn Tyr Leu Asp Gln Ile Ala Lys Phe Trp Glu Ile Gln
                85                  90                  95

Gly Ser Ser Leu Lys Ile Pro Asn Val Glu Arg Lys Ile Leu Asp Leu
            100                 105                 110

Tyr Ser Leu Ser Lys Ile Val Ile Glu Glu Gly Gly Tyr Glu Ala Ile
        115                 120                 125

Cys Lys Asp Arg Arg Trp Ala Arg Val Ala Gln Arg Leu His Tyr Pro
    130                 135                 140

Pro Gly Lys Asn Ile Gly Ser Leu Leu Arg Ser His Tyr Glu Arg Ile
145                 150                 155                 160

Ile Tyr Pro Tyr Glu Met Phe Gln Ser Gly Ala Asn His Val Gln Cys
                165                 170                 175

Asn Thr His Pro Phe Asp Asn Glu Val Lys Asp Lys Glu Tyr Lys Pro
            180                 185                 190

His Ser Ile Pro Leu Arg Gln Ser Val Gln Pro Ser Lys Phe Ser Ser
        195                 200                 205

Tyr Ser Arg Arg Ala Lys Arg Leu Gln Pro Asp Pro Glu Pro Thr Glu
    210                 215                 220

Glu Asp Ile Glu Lys His Pro Glu Leu Lys Lys Leu Gln Ile Tyr Gly
225                 230                 235                 240

Pro Gly Pro Lys Met Met Gly Leu Gly Leu Met Ala Lys Asp Lys Asp
                245                 250                 255

Lys Thr Val His Lys Lys Val Thr Cys Pro Pro Thr Val Thr Val Lys
            260                 265                 270

Asp Glu Gln Ser Gly Gly Gly Asn Val Ser Ser Thr Leu Leu Lys Gln
        275                 280                 285

His Leu Ser Leu Glu Pro Cys Thr Lys Thr Thr Met Gln Leu Arg Lys

```
              290                 295                 300
Asn His Ser Ser Ala Gln Phe Ile Asp Ser Tyr Ile Cys Gln Val Cys
305                 310                 315                 320

Ser Arg Gly Asp Glu Asp Lys Leu Leu Phe Cys Asp Gly Cys Asp
                325                 330                 335

Asp Asn Tyr His Ile Phe Cys Leu Leu Pro Pro Leu Pro Glu Ile Pro
                340                 345                 350

Arg Gly Ile Trp Arg Cys Pro Lys Cys Ile Leu Ala Glu Cys Lys Gln
                355                 360                 365

Pro Pro Glu Ala Phe Gly Phe Glu Gln Ala Thr Gln Glu Tyr Ser Leu
        370                 375                 380

Gln Ser Phe Gly Glu Met Ala Asp Ser Phe Lys Ser Asp Tyr Phe Asn
385                 390                 395                 400

Met Pro Val His Met Val Pro Thr Glu Leu Val Glu Lys Glu Phe Trp
                405                 410                 415

Arg Leu Val Ser Ser Ile Glu Glu Asp Val Thr Val Glu Tyr Gly Ala
                420                 425                 430

Asp Ile His Ser Lys Glu Phe Gly Ser Gly Phe Pro Val Ser Asn Ser
        435                 440                 445

Lys Gln Asn Leu Ser Pro Glu Glu Lys Arg Gln Ser Leu Thr Val Leu
450                 455                 460

Thr Arg Leu Ile Ser Ser Phe Trp Ala Gln Ala Val Leu Pro Pro Trp
465                 470                 475                 480

Pro Pro Lys Val Leu Gly Leu Gln Glu Tyr Ala Thr Ser Gly Trp Asn
                485                 490                 495

Leu Asn Val Met Pro Val Leu Asp Gln Ser Val Leu Cys His Ile Asn
                500                 505                 510

Ala Asp Ile Ser Gly Met Lys Val Pro Trp Leu Tyr Val Gly Met Val
        515                 520                 525

Phe Ser Ala Phe Cys Trp His Ile Glu Asp His Trp Ser Tyr Ser Ile
530                 535                 540

Asn Tyr Leu His Trp Gly Glu Pro Lys Thr Trp Tyr Gly Val Pro Ser
545                 550                 555                 560

Leu Ala Ala Glu His Leu Glu Glu Val Met Lys Met Leu Thr Pro Glu
                565                 570                 575

Leu Phe Asp Ser Gln Pro Asp Leu Leu His Gln Leu Val Thr Leu Met
                580                 585                 590

Asn Pro Asn Thr Leu Met Ser His Gly Val Pro Val Val Arg Thr Asn
        595                 600                 605

Gln Cys Ala Gly Glu Phe Val Ile Thr Phe Pro Arg Ala Tyr His Ser
610                 615                 620

Gly Phe Asn Gln Gly Tyr Asn Phe Ala Glu Ala Val Asn Phe Cys Thr
625                 630                 635                 640

Ala Asp Trp Leu Pro Ala Gly Arg Gln Cys Ile Glu His Tyr Arg Arg
                645                 650                 655

Leu Arg Arg Tyr Cys Val Phe Ser His Glu Glu Leu Ile Cys Lys Met
                660                 665                 670

Ala Ala Phe Pro Glu Thr Leu Asp Leu Asn Leu Ala Val Ala Val His
        675                 680                 685

Lys Glu Met Phe Ile Met Val Gln Glu Glu Arg Arg Leu Arg Lys Ala
690                 695                 700

Leu Leu Glu Lys Gly Val Thr Glu Ala Glu Arg Glu Ala Phe Glu Leu
705                 710                 715                 720
```

```
Leu Pro Asp Asp Glu Arg Gln Cys Ile Lys Cys Lys Thr Thr Cys Phe
                725                 730                 735

Leu Ser Ala Leu Ala Cys Tyr Asp Cys Pro Asp Gly Leu Val Cys Leu
            740                 745                 750

Ser His Ile Asn Asp Leu Cys Lys Cys Ser Ser Arg Gln Tyr Leu
        755                 760                 765

Arg Tyr Arg Tyr Thr Leu Asp Glu Leu Pro Thr Met Leu His Lys Leu
    770                 775                 780

Lys Ile Arg Ala Glu Ser Phe Asp Thr Trp Ala Asn Lys Val Arg Val
785                 790                 795                 800

Ala Leu Glu Val Glu Asp Gly Arg Lys Arg Ser Phe Glu Glu Leu Arg
                805                 810                 815

Ala Leu Glu Ser Glu Ala Arg Glu Arg Phe Pro Asn Ser Glu Leu
            820                 825                 830

Leu Gln Arg Leu Lys Asn Cys Leu Ser Glu Val Glu Ala Cys Ile Ala
        835                 840                 845

Gln Val Leu Gly Leu Val Ser Gly Gln Val Ala Arg Met Asp Thr Pro
    850                 855                 860

Gln Leu Thr Leu Thr Glu Leu Arg Val Leu Leu Glu Gln Met Gly Ser
865                 870                 875                 880

Leu Pro Cys Ala Met His Gln Ile Gly Asp Val Lys Asp Val Leu Glu
                885                 890                 895

Gln Val Glu Ala Tyr Gln Ala Glu Ala Arg Glu Ala Leu Ala Thr Leu
            900                 905                 910

Pro Ser Ser Pro Gly Leu Leu Arg Ser Leu Leu Glu Arg Gly Gln Gln
        915                 920                 925

Leu Gly Val Glu Val Pro Glu Ala His Gln Leu Gln Gln Gln Val Glu
    930                 935                 940

Gln Ala Gln Trp Leu Asp Glu Val Lys Gln Ala Leu Ala Pro Ser Ala
945                 950                 955                 960

His Arg Gly Ser Leu Val Ile Met Gln Gly Leu Leu Val Met Gly Ala
                965                 970                 975

Lys Ile Ala Ser Ser Pro Ser Val Asp Lys Ala Arg Ala Glu Leu Gln
            980                 985                 990

Glu Leu Leu Thr Ile Ala Glu Arg Trp Glu Glu Lys Ala His Phe Cys
        995                 1000                1005

Leu Glu Ala Arg Gln Lys His Pro Pro Ala Thr Leu Glu Ala Ile
     1010             1015                1020

Ile Arg Glu Thr Glu Asn Ile Pro Val His Leu Pro Asn Ile Gln
     1025             1030                1035

Ala Leu Lys Glu Ala Leu Thr Lys Ala Gln Ala Trp Ile Ala Asp
     1040             1045                1050

Val Asp Glu Ile Gln Asn Gly Asp His Tyr Pro Cys Leu Asp Asp
     1055             1060                1065

Leu Glu Gly Leu Val Ala Val Gly Arg Asp Leu Pro Val Gly Leu
     1070             1075                1080

Glu Glu Leu Arg Gln Leu Glu Leu Gln Val Leu Thr Ala His Ser
     1085             1090                1095

Trp Arg Glu Lys Ala Ser Lys Thr Phe Leu Lys Lys Asn Ser Cys
     1100             1105                1110

Tyr Thr Leu Leu Glu Val Leu Cys Pro Cys Ala Asp Ala Gly Ser
     1115             1120                1125
```

```
Asp Ser Thr Lys Arg Ser Arg Trp Met Glu Lys Ala Leu Gly Leu
    1130                1135                1140

Tyr Gln Cys Asp Thr Glu Leu Leu Gly Leu Ser Ala Gln Asp Leu
    1145                1150                1155

Arg Asp Pro Gly Ser Val Ile Val Ala Phe Lys Glu Gly Glu Gln
    1160                1165                1170

Lys Glu Lys Glu Gly Ile Leu Gln Leu Arg Arg Thr Asn Ser Ala
    1175                1180                1185

Lys Pro Ser Pro Leu Ala Pro Ser Leu Met Ala Ser Ser Pro Thr
    1190                1195                1200

Ser Ile Cys Val Cys Gly Gln Val Pro Ala Gly Val Gly Val Leu
    1205                1210                1215

Gln Cys Asp Leu Cys Gln Asp Trp Phe His Gly Gln Cys Val Ser
    1220                1225                1230

Val Pro His Leu Leu Thr Ser Pro Lys Pro Ser Leu Thr Ser Ser
    1235                1240                1245

Pro Leu Leu Ala Trp Trp Glu Trp Asp Thr Lys Phe Leu Cys Pro
    1250                1255                1260

Leu Cys Met Arg Ser Arg Arg Pro Arg Leu Glu Thr Ile Leu Ala
    1265                1270                1275

Leu Leu Val Ala Leu Gln Arg Leu Pro Val Arg Leu Pro Glu Gly
    1280                1285                1290

Glu Ala Leu Gln Cys Leu Thr Glu Arg Ala Ile Gly Trp Gln Asp
    1295                1300                1305

Arg Ala Arg Lys Ala Leu Ala Ser Glu Asp Val Thr Ala Leu Leu
    1310                1315                1320

Arg Gln Leu Ala Glu Leu Arg Gln Gln Leu Gln Ala Lys Pro Arg
    1325                1330                1335

Pro Glu Glu Ala Ser Val Tyr Thr Ser Ala Thr Ala Cys Asp Pro
    1340                1345                1350

Ile Arg Glu Gly Ser Gly Asn Asn Ile Ser Lys Val Gln Gly Leu
    1355                1360                1365

Leu Glu Asn Gly Asp Ser Val Thr Ser Pro Glu Asn Met Ala Pro
    1370                1375                1380

Gly Lys Gly Ser Asp Leu Glu Leu Leu Ser Ser Leu Leu Pro Gln
    1385                1390                1395

Leu Thr Gly Pro Val Leu Glu Leu Pro Glu Ala Ile Arg Ala Pro
    1400                1405                1410

Leu Glu Glu Leu Met Met Glu Gly Asp Leu Leu Glu Val Thr Leu
    1415                1420                1425

Asp Glu Asn His Ser Ile Trp Gln Leu Leu Gln Ala Gly Gln Pro
    1430                1435                1440

Pro Asp Leu Asp Arg Ile Arg Thr Leu Leu Glu Leu Glu Lys Phe
    1445                1450                1455

Glu His Gln Gly Ser Arg Thr Arg Ser Arg Ala Leu Glu Arg Arg
    1460                1465                1470

Arg Arg Arg Gln Lys Val Asp Gln Gly Arg Asn Val Glu Asn Leu
    1475                1480                1485

Val Gln Gln Glu Leu Gln Ser Lys Arg Ala Arg Ser Ser Gly Ile
    1490                1495                1500

Met Ser Gln Val Gly Arg Glu Glu His Tyr Gln Glu Lys Ala
    1505                1510                1515

Asp Arg Glu Asn Met Phe Leu Thr Pro Ser Thr Asp His Ser Pro
```

```
            1520                1525                1530

Phe Leu Lys Gly Asn Gln Asn  Ser Leu Gln His Lys  Asp Ser Gly
        1535                1540                1545

Ser Ser Ala Ala Cys Pro Ser  Leu Met Pro Leu Leu  Gln Leu Ser
        1550                1555                1560

Tyr Ser Asp Glu Gln Gln Leu
        1565                1570

<210> SEQ ID NO 8
<211> LENGTH: 1539
<212> TYPE: PRT
<213> ORGANISM: Homo sapiens

<400> SEQUENCE: 8

Met Glu Pro Gly Cys Asp Glu  Phe Leu Pro Pro Pro  Glu Cys Pro Val
1               5                    10                   15

Phe Glu Pro Ser Trp Ala Glu  Phe Gln Asp Pro Leu  Gly Tyr Ile Ala
                20                   25                   30

Lys Ile Arg Pro Ile Ala Glu  Lys Ser Gly Ile Cys  Lys Ile Arg Pro
            35                   40                   45

Pro Ala Asp Trp Gln Pro Pro  Phe Ala Val Glu Val  Asp Asn Phe Arg
        50                   55                   60

Phe Thr Pro Arg Val Gln Arg  Leu Asn Glu Leu Glu  Ala Gln Thr Arg
65                  70                   75                   80

Val Lys Leu Asn Tyr Leu Asp  Gln Ile Ala Lys Phe  Trp Glu Ile Gln
                85                   90                   95

Gly Ser Ser Leu Lys Ile Pro  Asn Val Glu Arg Lys  Ile Leu Asp Leu
                100                  105                  110

Tyr Ser Leu Ser Lys Ile Val  Ile Glu Glu Gly Gly  Tyr Glu Ala Ile
                115                  120                  125

Cys Lys Asp Arg Arg Trp Ala  Arg Val Ala Gln Arg  Leu His Tyr Pro
        130                  135                  140

Pro Gly Lys Asn Ile Gly Ser  Leu Leu Arg Ser His  Tyr Glu Arg Ile
145                 150                  155                  160

Ile Tyr Pro Tyr Glu Met Phe  Gln Ser Gly Ala Asn  His Val Gln Cys
                165                  170                  175

Asn Thr His Pro Phe Asp Asn  Glu Val Lys Asp Lys  Glu Tyr Lys Pro
                180                  185                  190

His Ser Ile Pro Leu Arg Gln  Ser Val Gln Pro Ser  Lys Phe Ser Ser
            195                  200                  205

Tyr Ser Arg Arg Ala Lys Arg  Leu Gln Pro Asp Pro  Glu Pro Thr Glu
        210                  215                  220

Glu Asp Ile Glu Lys His Pro  Glu Leu Lys Lys Leu  Gln Ile Tyr Gly
225                 230                  235                  240

Pro Gly Pro Lys Met Met Gly  Leu Gly Leu Met Ala  Lys Asp Lys Asp
                245                  250                  255

Lys Thr Val His Lys Lys Val  Thr Cys Pro Pro Thr  Val Thr Val Lys
                260                  265                  270

Asp Glu Gln Ser Gly Gly Gly  Asn Val Ser Ser Thr  Leu Leu Lys Gln
            275                  280                  285

His Leu Ser Leu Glu Pro Cys  Thr Lys Thr Thr Met  Gln Leu Arg Lys
        290                  295                  300

Asn His Ser Ser Ala Gln Phe  Ile Asp Ser Tyr Ile  Cys Gln Val Cys
305                 310                  315                  320
```

-continued

```
Ser Arg Gly Asp Glu Asp Lys Leu Leu Phe Cys Asp Gly Cys Asp
                325                 330                 335

Asp Asn Tyr His Ile Phe Cys Leu Leu Pro Pro Leu Pro Glu Ile Pro
            340                 345                 350

Arg Gly Ile Trp Arg Cys Pro Lys Cys Ile Leu Ala Glu Cys Lys Gln
        355                 360                 365

Pro Pro Glu Ala Phe Gly Phe Glu Gln Ala Thr Gln Glu Tyr Ser Leu
370                 375                 380

Gln Ser Phe Gly Glu Met Ala Asp Ser Phe Lys Ser Asp Tyr Phe Asn
385                 390                 395                 400

Met Pro Val His Met Val Pro Thr Glu Leu Val Glu Lys Glu Phe Trp
                405                 410                 415

Arg Leu Val Ser Ser Ile Glu Glu Asp Val Thr Val Glu Tyr Gly Ala
            420                 425                 430

Asp Ile His Ser Lys Glu Phe Gly Ser Gly Phe Pro Val Ser Asn Ser
        435                 440                 445

Lys Gln Asn Leu Ser Pro Glu Glu Lys Glu Tyr Ala Thr Ser Gly Trp
450                 455                 460

Asn Leu Asn Val Met Pro Val Leu Asp Gln Ser Val Leu Cys His Ile
465                 470                 475                 480

Asn Ala Asp Ile Ser Gly Met Lys Val Pro Trp Leu Tyr Val Gly Met
                485                 490                 495

Val Phe Ser Ala Phe Cys Trp His Ile Glu Asp His Trp Ser Tyr Ser
            500                 505                 510

Ile Asn Tyr Leu His Trp Gly Glu Pro Lys Thr Trp Tyr Gly Val Pro
        515                 520                 525

Ser Leu Ala Ala Glu His Leu Glu Glu Val Met Lys Met Leu Thr Pro
530                 535                 540

Glu Leu Phe Asp Ser Gln Pro Asp Leu Leu His Gln Leu Val Thr Leu
545                 550                 555                 560

Met Asn Pro Asn Thr Leu Met Ser His Gly Val Pro Val Val Arg Thr
                565                 570                 575

Asn Gln Cys Ala Gly Glu Phe Val Ile Thr Phe Pro Arg Ala Tyr His
            580                 585                 590

Ser Gly Phe Asn Gln Gly Tyr Asn Phe Ala Glu Ala Val Asn Phe Cys
        595                 600                 605

Thr Ala Asp Trp Leu Pro Ala Gly Arg Gln Cys Ile Glu His Tyr Arg
610                 615                 620

Arg Leu Arg Arg Tyr Cys Val Phe Ser His Glu Glu Leu Ile Cys Lys
625                 630                 635                 640

Met Ala Ala Phe Pro Glu Thr Leu Asp Leu Asn Leu Ala Val Ala Val
                645                 650                 655

His Lys Glu Met Phe Ile Met Val Gln Glu Glu Arg Arg Leu Arg Lys
            660                 665                 670

Ala Leu Leu Glu Lys Gly Val Thr Glu Ala Glu Arg Glu Ala Phe Glu
        675                 680                 685

Leu Leu Pro Asp Asp Glu Arg Gln Cys Ile Lys Cys Lys Thr Thr Cys
690                 695                 700

Phe Leu Ser Ala Leu Ala Cys Tyr Asp Cys Pro Asp Gly Leu Val Cys
705                 710                 715                 720

Leu Ser His Ile Asn Asp Leu Cys Lys Cys Ser Ser Ser Arg Gln Tyr
                725                 730                 735

Leu Arg Tyr Arg Tyr Thr Leu Asp Glu Leu Pro Thr Met Leu His Lys
```

-continued

```
                740                 745                 750
Leu Lys Ile Arg Ala Glu Ser Phe Asp Thr Trp Ala Asn Lys Val Arg
            755                 760                 765

Val Ala Leu Glu Val Glu Asp Gly Arg Lys Arg Ser Phe Glu Glu Leu
770                 775                 780

Arg Ala Leu Glu Ser Glu Ala Arg Glu Arg Arg Phe Pro Asn Ser Glu
785                 790                 795                 800

Leu Leu Gln Arg Leu Lys Asn Cys Leu Ser Glu Val Glu Ala Cys Ile
            805                 810                 815

Ala Gln Val Leu Gly Leu Val Ser Gly Gln Val Ala Arg Met Asp Thr
            820                 825                 830

Pro Gln Leu Thr Leu Thr Glu Leu Arg Val Leu Leu Glu Gln Met Gly
            835                 840                 845

Ser Leu Pro Cys Ala Met His Gln Ile Gly Asp Val Lys Asp Val Leu
            850                 855                 860

Glu Gln Val Glu Ala Tyr Gln Ala Glu Ala Arg Glu Ala Leu Ala Thr
865                 870                 875                 880

Leu Pro Ser Ser Pro Gly Leu Leu Arg Ser Leu Leu Glu Arg Gly Gln
            885                 890                 895

Gln Leu Gly Val Glu Val Pro Glu Ala His Gln Leu Gln Gln Gln Val
            900                 905                 910

Glu Gln Ala Gln Trp Leu Asp Glu Val Lys Gln Ala Leu Ala Pro Ser
            915                 920                 925

Ala His Arg Gly Ser Leu Val Ile Met Gln Gly Leu Leu Val Met Gly
            930                 935                 940

Ala Lys Ile Ala Ser Ser Pro Ser Val Asp Lys Ala Arg Ala Glu Leu
945                 950                 955                 960

Gln Glu Leu Leu Thr Ile Ala Glu Arg Trp Glu Lys Ala His Phe
            965                 970                 975

Cys Leu Glu Ala Arg Gln Lys His Pro Pro Ala Thr Leu Glu Ala Ile
            980                 985                 990

Ile Arg Glu Thr Glu Asn Ile Pro  Val His Leu Pro Asn  Ile Gln Ala
            995                 1000                1005

Leu Lys  Glu Ala Leu Thr Lys  Ala Gln Ala Trp Ile  Ala Asp Val
            1010                1015                1020

Asp Glu  Ile Gln Asn Gly Asp  His Tyr Pro Cys Leu  Asp Asp Leu
            1025                1030                1035

Glu Gly  Leu Val Ala Val Gly  Arg Asp Leu Pro Val  Gly Leu Glu
            1040                1045                1050

Glu Leu  Arg Gln Leu Glu Leu  Gln Val Leu Thr Ala  His Ser Trp
            1055                1060                1065

Arg Glu  Lys Ala Ser Lys Thr  Phe Leu Lys Lys Asn  Ser Cys Tyr
            1070                1075                1080

Thr Leu  Leu Glu Val Leu Cys  Pro Cys Ala Asp Ala  Gly Ser Asp
            1085                1090                1095

Ser Thr  Lys Arg Ser Arg Trp  Met Glu Lys Ala Leu  Gly Leu Tyr
            1100                1105                1110

Gln Cys  Asp Thr Glu Leu Leu  Gly Leu Ser Ala Gln  Asp Leu Arg
            1115                1120                1125

Asp Pro  Gly Ser Val Ile Val  Ala Phe Lys Glu Gly  Glu Gln Lys
            1130                1135                1140

Glu Lys  Glu Gly Ile Leu Gln  Leu Arg Arg Thr Asn  Ser Ala Lys
            1145                1150                1155
```

```
Pro Ser Pro Leu Ala Pro Ser Leu Met Ala Ser Ser Pro Thr Ser
    1160                1165             1170

Ile Cys Val Cys Gly Gln Val Pro Ala Gly Val Gly Val Leu Gln
    1175                1180             1185

Cys Asp Leu Cys Gln Asp Trp Phe His Gly Gln Cys Val Ser Val
    1190                1195             1200

Pro His Leu Leu Thr Ser Pro Lys Pro Ser Leu Thr Ser Ser Pro
    1205                1210             1215

Leu Leu Ala Trp Trp Glu Trp Asp Thr Lys Phe Leu Cys Pro Leu
    1220                1225             1230

Cys Met Arg Ser Arg Pro Arg Leu Glu Thr Ile Leu Ala Leu
    1235                1240             1245

Leu Val Ala Leu Gln Arg Leu Pro Val Arg Leu Pro Glu Gly Glu
    1250                1255             1260

Ala Leu Gln Cys Leu Thr Glu Arg Ala Ile Gly Trp Gln Asp Arg
    1265                1270             1275

Ala Arg Lys Ala Leu Ala Ser Glu Asp Val Thr Ala Leu Leu Arg
    1280                1285             1290

Gln Leu Ala Glu Leu Arg Gln Gln Leu Gln Ala Lys Pro Arg Pro
    1295                1300             1305

Glu Glu Ala Ser Val Tyr Thr Ser Ala Thr Ala Cys Asp Pro Ile
    1310                1315             1320

Arg Glu Gly Ser Gly Asn Asn Ile Ser Lys Val Gln Gly Leu Leu
    1325                1330             1335

Glu Asn Gly Asp Ser Val Thr Ser Pro Glu Asn Met Ala Pro Gly
    1340                1345             1350

Lys Gly Ser Asp Leu Glu Leu Leu Ser Ser Leu Leu Pro Gln Leu
    1355                1360             1365

Thr Gly Pro Val Leu Glu Leu Pro Glu Ala Ile Arg Ala Pro Leu
    1370                1375             1380

Glu Glu Leu Met Met Glu Gly Asp Leu Leu Glu Val Thr Leu Asp
    1385                1390             1395

Glu Asn His Ser Ile Trp Gln Leu Leu Gln Ala Gly Gln Pro Pro
    1400                1405             1410

Asp Leu Asp Arg Ile Arg Thr Leu Leu Glu Leu Glu Lys Phe Glu
    1415                1420             1425

His Gln Gly Ser Arg Thr Arg Ser Arg Ala Leu Glu Arg Arg Arg
    1430                1435             1440

Arg Arg Gln Lys Val Asp Gln Gly Arg Asn Val Glu Asn Leu Val
    1445                1450             1455

Gln Gln Glu Leu Gln Ser Lys Arg Ala Arg Ser Ser Gly Ile Met
    1460                1465             1470

Ser Gln Val Gly Arg Glu Glu His Tyr Gln Glu Lys Ala Asp
    1475                1480             1485

Arg Glu Asn Met Phe Leu Thr Pro Ser Thr Asp His Ser Pro Phe
    1490                1495             1500

Leu Lys Gly Asn Gln Asn Ser Leu Gln His Lys Asp Ser Gly Ser
    1505                1510             1515

Ser Ala Ala Cys Pro Ser Leu Met Pro Leu Leu Gln Leu Ser Tyr
    1520                1525             1530

Ser Asp Glu Gln Gln Leu
    1535
```

<210> SEQ ID NO 9
<211> LENGTH: 1482
<212> TYPE: PRT
<213> ORGANISM: Homo sapiens

<400> SEQUENCE: 9

```
Met Glu Pro Gly Cys Asp Glu Phe Leu Pro Pro Glu Cys Pro Val
1               5                   10                  15

Phe Glu Pro Ser Trp Ala Glu Phe Gln Asp Pro Leu Gly Tyr Ile Ala
                20                  25                  30

Lys Ile Arg Pro Ile Ala Glu Lys Ser Gly Ile Cys Lys Ile Arg Pro
            35                  40                  45

Pro Ala Asp Trp Gln Pro Pro Phe Ala Val Glu Val Asp Asn Phe Arg
50                  55                  60

Phe Thr Pro Arg Val Gln Arg Leu Asn Glu Leu Glu Ala Gln Thr Arg
65                  70                  75                  80

Val Lys Leu Asn Tyr Leu Asp Gln Ile Ala Lys Phe Trp Glu Ile Gln
                85                  90                  95

Gly Ser Ser Leu Lys Ile Pro Asn Val Glu Arg Lys Ile Leu Asp Leu
            100                 105                 110

Tyr Ser Leu Ser Lys Gln Cys Asn Thr His Pro Phe Asp Asn Glu Val
        115                 120                 125

Lys Asp Lys Glu Tyr Lys Pro His Ser Ile Pro Leu Arg Gln Ser Val
130                 135                 140

Gln Pro Ser Lys Phe Ser Ser Tyr Ser Arg Arg Ala Lys Arg Leu Gln
145                 150                 155                 160

Pro Asp Pro Glu Pro Thr Glu Glu Asp Ile Glu Lys His Pro Glu Leu
                165                 170                 175

Lys Lys Leu Gln Ile Tyr Gly Pro Gly Pro Lys Met Met Gly Leu Gly
            180                 185                 190

Leu Met Ala Lys Asp Lys Asp Lys Thr Val His Lys Lys Val Thr Cys
        195                 200                 205

Pro Pro Thr Val Thr Val Lys Asp Glu Gln Ser Gly Gly Gly Asn Val
210                 215                 220

Ser Ser Thr Leu Leu Lys Gln His Leu Ser Leu Glu Pro Cys Thr Lys
225                 230                 235                 240

Thr Thr Met Gln Leu Arg Lys Asn His Ser Ser Ala Gln Phe Ile Asp
                245                 250                 255

Ser Tyr Ile Cys Gln Val Cys Ser Arg Gly Asp Glu Asp Asp Lys Leu
            260                 265                 270

Leu Phe Cys Asp Gly Cys Asp Asp Asn Tyr His Ile Phe Cys Leu Leu
        275                 280                 285

Pro Pro Leu Pro Glu Ile Pro Arg Gly Ile Trp Arg Cys Pro Lys Cys
290                 295                 300

Ile Leu Ala Glu Cys Lys Gln Pro Pro Glu Ala Phe Gly Phe Glu Gln
305                 310                 315                 320

Ala Thr Gln Glu Tyr Ser Leu Gln Ser Phe Gly Glu Met Ala Asp Ser
                325                 330                 335

Phe Lys Ser Asp Tyr Phe Asn Met Pro Val His Met Val Pro Thr Glu
            340                 345                 350

Leu Val Glu Lys Glu Phe Trp Arg Leu Val Ser Ser Ile Glu Glu Asp
        355                 360                 365

Val Thr Val Glu Tyr Gly Ala Asp Ile His Ser Lys Glu Phe Gly Ser
370                 375                 380
```

```
Gly Phe Pro Val Ser Asn Ser Lys Gln Asn Leu Ser Pro Glu Glu Lys
385                 390                 395                 400

Glu Tyr Ala Thr Ser Gly Trp Asn Leu Asn Val Met Pro Val Leu Asp
                405                 410                 415

Gln Ser Val Leu Cys His Ile Asn Ala Asp Ile Ser Gly Met Lys Val
            420                 425                 430

Pro Trp Leu Tyr Val Gly Met Val Phe Ser Ala Phe Cys Trp His Ile
        435                 440                 445

Glu Asp His Trp Ser Tyr Ser Ile Asn Tyr Leu His Trp Gly Glu Pro
    450                 455                 460

Lys Thr Trp Tyr Gly Val Pro Ser Leu Ala Ala Glu His Leu Glu Glu
465                 470                 475                 480

Val Met Lys Met Leu Thr Pro Glu Leu Phe Asp Ser Gln Pro Asp Leu
                485                 490                 495

Leu His Gln Leu Val Thr Leu Met Asn Pro Asn Thr Leu Met Ser His
            500                 505                 510

Gly Val Pro Val Val Arg Thr Asn Gln Cys Ala Gly Glu Phe Val Ile
        515                 520                 525

Thr Phe Pro Arg Ala Tyr His Ser Gly Phe Asn Gln Gly Tyr Asn Phe
    530                 535                 540

Ala Glu Ala Val Asn Phe Cys Thr Ala Asp Trp Leu Pro Ala Gly Arg
545                 550                 555                 560

Gln Cys Ile Glu His Tyr Arg Arg Leu Arg Arg Tyr Cys Val Phe Ser
                565                 570                 575

His Glu Glu Leu Ile Cys Lys Met Ala Ala Phe Pro Glu Thr Leu Asp
            580                 585                 590

Leu Asn Leu Ala Val Ala Val His Lys Glu Met Phe Ile Met Val Gln
        595                 600                 605

Glu Glu Arg Arg Leu Arg Lys Ala Leu Leu Glu Lys Gly Val Thr Glu
    610                 615                 620

Ala Glu Arg Glu Ala Phe Glu Leu Leu Pro Asp Asp Glu Arg Gln Cys
625                 630                 635                 640

Ile Lys Cys Lys Thr Thr Cys Phe Leu Ser Ala Leu Ala Cys Tyr Asp
                645                 650                 655

Cys Pro Asp Gly Leu Val Cys Leu Ser His Ile Asn Asp Leu Cys Lys
            660                 665                 670

Cys Ser Ser Ser Arg Gln Tyr Leu Arg Tyr Arg Tyr Thr Leu Asp Glu
        675                 680                 685

Leu Pro Thr Met Leu His Lys Leu Lys Ile Arg Ala Glu Ser Phe Asp
    690                 695                 700

Thr Trp Ala Asn Lys Val Arg Val Ala Leu Glu Val Glu Asp Gly Arg
705                 710                 715                 720

Lys Arg Ser Phe Glu Glu Leu Arg Ala Leu Ser Glu Ala Arg Glu
                725                 730                 735

Arg Arg Phe Pro Asn Ser Glu Leu Leu Gln Arg Leu Lys Asn Cys Leu
            740                 745                 750

Ser Glu Val Glu Ala Cys Ile Ala Gln Val Leu Gly Leu Val Ser Gly
        755                 760                 765

Gln Val Ala Arg Met Asp Thr Pro Gln Leu Thr Leu Thr Glu Leu Arg
    770                 775                 780

Val Leu Leu Glu Gln Met Gly Ser Leu Pro Cys Ala Met His Gln Ile
785                 790                 795                 800
```

```
Gly Asp Val Lys Asp Val Leu Glu Gln Val Glu Ala Tyr Gln Ala Glu
            805                 810                 815

Ala Arg Glu Ala Leu Ala Thr Leu Pro Ser Ser Pro Gly Leu Leu Arg
        820                 825                 830

Ser Leu Leu Glu Arg Gly Gln Gln Leu Gly Val Glu Val Pro Glu Ala
        835                 840                 845

His Gln Leu Gln Gln Gln Val Glu Gln Ala Gln Trp Leu Asp Glu Val
    850                 855                 860

Lys Gln Ala Leu Ala Pro Ser Ala His Arg Gly Ser Leu Val Ile Met
865                 870                 875                 880

Gln Gly Leu Leu Val Met Gly Ala Lys Ile Ala Ser Ser Pro Ser Val
            885                 890                 895

Asp Lys Ala Arg Ala Glu Leu Gln Glu Leu Leu Thr Ile Ala Glu Arg
        900                 905                 910

Trp Glu Glu Lys Ala His Phe Cys Leu Glu Ala Arg Gln Lys His Pro
        915                 920                 925

Pro Ala Thr Leu Glu Ala Ile Ile Arg Glu Thr Glu Asn Ile Pro Val
        930                 935                 940

His Leu Pro Asn Ile Gln Ala Leu Lys Glu Ala Leu Thr Lys Ala Gln
945                 950                 955                 960

Ala Trp Ile Ala Asp Val Asp Glu Ile Gln Asn Gly Asp His Tyr Pro
            965                 970                 975

Cys Leu Asp Asp Leu Glu Gly Leu Val Ala Val Gly Arg Asp Leu Pro
        980                 985                 990

Val Gly Leu Glu Glu Leu Arg Gln Leu Glu Leu Gln Val Leu Thr Ala
        995                 1000                 1005

His Ser Trp Arg Glu Lys Ala Ser Lys Thr Phe Leu Lys Lys Asn
    1010                1015                1020

Ser Cys Tyr Thr Leu Leu Glu Val Leu Cys Pro Cys Ala Asp Ala
    1025                1030                1035

Gly Ser Asp Ser Thr Lys Arg Ser Arg Trp Met Glu Lys Ala Leu
    1040                1045                1050

Gly Leu Tyr Gln Cys Asp Thr Glu Leu Leu Gly Leu Ser Ala Gln
    1055                1060                1065

Asp Leu Arg Asp Pro Gly Ser Val Ile Val Ala Phe Lys Glu Gly
    1070                1075                1080

Glu Gln Lys Glu Lys Glu Gly Ile Leu Gln Leu Arg Arg Thr Asn
    1085                1090                1095

Ser Ala Lys Pro Ser Pro Leu Ala Pro Ser Leu Met Ala Ser Ser
    1100                1105                1110

Pro Thr Ser Ile Cys Val Cys Gly Gln Val Pro Ala Gly Val Gly
    1115                1120                1125

Val Leu Gln Cys Asp Leu Cys Gln Asp Trp Phe His Gly Gln Cys
    1130                1135                1140

Val Ser Val Pro His Leu Leu Thr Ser Pro Lys Pro Ser Leu Thr
    1145                1150                1155

Ser Ser Pro Leu Leu Ala Trp Trp Glu Trp Asp Thr Lys Phe Leu
    1160                1165                1170

Cys Pro Leu Cys Met Arg Ser Arg Arg Pro Arg Leu Glu Thr Ile
    1175                1180                1185

Leu Ala Leu Leu Val Ala Leu Gln Arg Leu Pro Val Arg Leu Pro
    1190                1195                1200

Glu Gly Glu Ala Leu Gln Cys Leu Thr Glu Arg Ala Ile Gly Trp
```

-continued

```
            1205                1210                1215
Gln Asp Arg Ala Arg Lys Ala Leu Ala Ser Glu Asp Val Thr Ala
    1220                1225                1230
Leu Leu Arg Gln Leu Ala Glu Leu Arg Gln Gln Leu Gln Ala Lys
    1235                1240                1245
Pro Arg Pro Glu Glu Ala Ser Val Tyr Thr Ser Ala Thr Ala Cys
    1250                1255                1260
Asp Pro Ile Arg Glu Gly Ser Gly Asn Asn Ile Ser Lys Val Gln
    1265                1270                1275
Gly Leu Leu Glu Asn Gly Asp Ser Val Thr Ser Pro Glu Asn Met
    1280                1285                1290
Ala Pro Gly Lys Gly Ser Asp Leu Glu Leu Leu Ser Ser Leu Leu
    1295                1300                1305
Pro Gln Leu Thr Gly Pro Val Leu Glu Leu Pro Glu Ala Ile Arg
    1310                1315                1320
Ala Pro Leu Glu Glu Leu Met Met Glu Gly Asp Leu Leu Glu Val
    1325                1330                1335
Thr Leu Asp Glu Asn His Ser Ile Trp Gln Leu Leu Gln Ala Gly
    1340                1345                1350
Gln Pro Pro Asp Leu Asp Arg Ile Arg Thr Leu Leu Glu Leu Glu
    1355                1360                1365
Lys Phe Glu His Gln Gly Ser Arg Thr Arg Ser Arg Ala Leu Glu
    1370                1375                1380
Arg Arg Arg Arg Arg Gln Lys Val Asp Gln Gly Arg Asn Val Glu
    1385                1390                1395
Asn Leu Val Gln Gln Glu Leu Gln Ser Lys Arg Ala Arg Ser Ser
    1400                1405                1410
Gly Ile Met Ser Gln Val Gly Arg Glu Glu His Tyr Gln Glu
    1415                1420                1425
Lys Ala Asp Arg Glu Asn Met Phe Leu Thr Pro Ser Thr Asp His
    1430                1435                1440
Ser Pro Phe Leu Lys Gly Asn Gln Asn Ser Leu Gln His Lys Asp
    1445                1450                1455
Ser Gly Ser Ser Ala Ala Cys Pro Ser Leu Met Pro Leu Leu Gln
    1460                1465                1470
Leu Ser Tyr Ser Asp Glu Gln Leu
    1475                1480
```

COMPOSITIONS AND METHODS FOR SCREENING AND DIAGNOSIS OF PROSTATE CANCER

CROSS-REFERENCE TO RELATED APPLICATIONS

This application is a division of U.S. application Ser. No. 16/066,876, filed Jun. 28, 2018, which is a U.S. National Phase application, filed under 35 U.S.C. § 371, of national stage entry of International No. PCT/US16/69382, filed Dec. 30, 2016 which claims the benefit of U.S. Provisional Application No. 62/273,946, filed Dec. 31, 2015, the contents of each are incorporated herein by reference in their entireties.

BACKGROUND

Prostate cancer is the most common non-skin cancer and second most common cause of cancer mortality in men in the United States. Most prostate cancer is initially androgen dependent, i.e. prostate cancer cells require androgen for continued proliferation. Androgen deprivation therapy (ADT) through either surgery or medical treatment rapidly leads to apoptosis of androgen-dependent cancer cells. ADT has been the mainstay of treatment for metastatic hormone sensitive prostate cancer (mHSPC) for more than 70 years.

In many cases, however, some cancer cells survive and become androgen independent or unresponsive, leading to recurrence of prostate cancer. Chemotherapy has been reserved for metastatic castration-resistant prostate cancer (mCRPC), a type of androgen-independent prostate cancer. Taxanes and DNA damaging agents are two major classes of chemotherapeutics used for treating prostate cancer. Among these drugs docetaxel, a taxane, is currently a first-line therapy for mCRPC. Docetaxel imparts about a 2 month prolongation of median overall survival (OS) over mitoxantrone, a DNA damaging agent. While drug resistance to docetaxel arises, new medicines further prolong OS in the post-docetaxel setting. For example, cabazitaxel, a newly developed taxane, improves median OS by 2.4 months from 12.7 months to 15.1 months over mitoxantrone in docetaxel-resistant patients.

A recent clinical trial explored the benefit of treating hormone-sensitive cancers more aggressively in the beginning. This ECOG led trial, E3805: CHAARTED, showed that docetaxel given at the time of starting ADT for mHSPC improved OS by 13 months from 44 to 57 months. These findings were confirmed by the STAMPEDE trial conducted in the United Kingdom. It is unknown why docetaxel deployed with concurrent ADT improves OS to such a dramatic degree for patients with naive mHSPC. The present invention identifies a mechanism underlying the clinical benefit and develops a strategy of patient stratification, sparing some patients from the long-term side effects of ADT without losing efficacy.

SUMMARY

The present disclosure provides a method of screening for and diagnosing prostate cancer and methods of selecting a treatment for prostate cancer, the method comprising:
(a) measuring the expression level of KDM5D in a sample from the subject;
(b) comparing the measured expression level of KDM5D in the sample from the subject to a reference expression level of KDM5D in a control sample, wherein administration of a taxane and an androgen deprivation therapy (ADT) does not provide a higher likelihood of improvement than administration of a taxane without ADT or administration of ADT without a taxane if the expression level of KDM5D in the sample from the subject is the same as or higher than the reference expression level of KDM5D in the control sample.

In some embodiments, the control sample is a normal prostate tissue or a primary prostate tumor. In some embodiments, the control sample is LNCaP cells.

In some embodiments, the prostate cancer is a hormone-naive prostate cancer. In some embodiments, the prostate cancer is hormone-sensitive prostate cancer. In some embodiments, the prostate cancer is castration-resistant prostate cancer. In some embodiments, the prostate cancer is hormone-refractory prostate cancer. In some embodiments, the prostate cancer is metastatic.

In some embodiments, the subject is a human.

In some embodiments, the sample is from a cancerous lesion. In certain embodiments, the sample comprises circulating tumor cells.

In some embodiments, the expression levels are RNA expression levels.

In some embodiments, the expression levels are protein expression levels.

In some embodiments, the taxane is selected from the group consisting of paclitaxel, docetaxel, protaxel, larotaxel, cabazitaxel, Abraxane, Ortataxel, Genexol, DJ-927 and BMS-184476. In some particular embodiments, the taxane is docetaxel.

In some embodiments, the androgen receptor antagonist is selected from the group consisting of flutamide, nilutamide, enzalutamide, bicalutamide, ketonazole, abiraterone, abiraterone acetate, orteronel, finasteride, dutasteride, bexlosteride, izonsteride, turosteride, episteride, dexamethasone, prednisone, leuprolide, goserelin, triptorelin, histrelin and estrogen. In some particular embodiments, the androgen receptor antagonist is enzalutamide.

In some embodiments, the improvement comprises improvement in one or more symptoms of a prostate cancer. In some particular embodiments, the symptoms of a prostate cancer comprise difficulty in urinating, blood in urine, erectile dysfunction, pain in the hips, pain in the back, pain the chest, weakness, numbness and incontinence.

In some embodiments, the improvement comprises a decrease in cancer load.

In some embodiments, a therapeutically effective amount of a taxane is administered to the subject following the steps (a) and (b). In some particular embodiments where the subject is already undergoing a taxane treatment, the treatment may continue, or a different taxane may be substituted.

The present disclosure also provides a method of screening for and diagnosing prostate cancer and methods of selecting a treatment for prostate cancer, the method comprising:
(a) measuring the expression level of KDM5D in a sample from the subject;
(b) comparing the measured expression level of KDM5D in the sample from the subject to a reference expression level of KDM5D in a control sample, wherein administration of a taxane and an androgen deprivation therapy (ADT) provides a higher likelihood of improvement than administration of a taxane without ADT or administration of ADT without a taxane if the expression level of KDM5D in the sample from the subject is lower than the reference level in the control sample.

In some embodiments, the control sample is a normal prostate tissue or a primary prostate tumor. In some embodiments, the control sample is LNCaP cells.

In some embodiments, the prostate cancer is a hormone-naive prostate cancer. In some embodiments, the prostate cancer is hormone-sensitive prostate cancer. In some embodiments, the prostate cancer is castration-resistant prostate cancer. In some embodiments, the prostate cancer is hormone-refractory prostate cancer. In some embodiments, the prostate cancer is metastatic.

In some embodiments, the subject is a human.

In some embodiments, the sample is from a cancerous lesion. In certain embodiments, the sample comprises circulating tumor cells.

In some embodiments, the expression levels are RNA expression levels.

In some embodiments, the expression levels are protein expression levels.

In some embodiments, the taxane is selected from the group consisting of paclitaxel, docetaxel, protaxel, larotaxel, cabazitaxel, Abraxane, Ortataxel, Genexol, DJ-927 and BMS-184476. In some particular embodiments, the taxane is docetaxel. In some particular embodiments, docetaxel is administered at a dose of about 10 to 70 mg/m.sup.2. In some particular embodiments, docetaxel is administered at a dose of about 10 to 50 mg/m.sup.2.

In some embodiments, the androgen receptor antagonist is selected from the group consisting of flutamide, nilutamide, enzalutamide, bicalutamide, ketonazole, abiraterone, abiraterone acetate, orteronel, finasteride, dutasteride, bexlosteride, izonsteride, turosteride, episteride, dexamethasone, prednisone, leuprolide, goserelin, triptorelin, histrelin and estrogen. In some particular embodiments, the androgen receptor antagonist is enzalutamide.

In some embodiments, the improvement comprises improvement in one or more symptoms of a prostate cancer. In some particular embodiments, the symptoms of a prostate cancer comprise difficulty in urinating, blood in urine, erectile dysfunction, pain in the hips, pain in the back, pain the chest, weakness, numbness and incontinence.

In some embodiments, the improvement comprises a decrease in cancer load.

In some embodiments, a therapeutically effective amount of a taxane and a therapeutically effective amount of an androgen deprivation therapy are administered to the subject following the steps (a) and (b). In some particular embodiments where the subject is already undergoing a taxane treatment, an androgen deprivation therapy is added to the ongoing taxane to make the taxane more effective. In some particular embodiments where the subject is already undergoing an ADT, a taxane is administered in addition to achieve a better therapeutic effect. In some particular embodiments where the subject is already undergoing both treatments, the treatments may continue, or a different taxane and/or a different ADT may be substituted for the existing taxane and/or ADT. The combination therapy can be provided in a single or multiple dosage forms.

In one aspect, the present disclosure provides a method of measuring expression of KDM5D in a subject having prostate cancer, the method comprising measuring the binding of a probe in a sample from the subject, wherein the probe specifically hybridizes to a DNA having the sequence set forth in SEQ ID NO: 2, 3, or 4, thereby measuring expression of KDM5D in the subject.

In some embodiments, the prostate cancer is a hormone-naive prostate cancer. In some embodiments, the prostate cancer is hormone-sensitive prostate cancer. In some embodiments, the prostate cancer is castration-resistant prostate cancer. In some embodiments, the prostate cancer is hormone-refractory prostate cancer. In some embodiments, the prostate cancer is metastatic.

In some embodiments, the subject is a human. In some embodiments, the sample is from a cancerous lesion. In certain embodiments, the sample comprises circulating tumor cells.

In some embodiments, the method further comprises administering to the subject a therapeutically effective amount of a taxane if the expression of KDM5D is the same as or higher than the reference expression level of KDM5D in a control sample.

In some embodiments, the method further comprises administering to the subject a therapeutically effective amount of a taxane and an ADT if the expression of KDM5D is lower than the reference expression level of KDM5D in a control sample. In some embodiments, the ADT is selected from the group consisting of flutamide, nilutamide, enzalutamide, bicalutamide, ketonazole, abiraterone, abiraterone acetate, orteronel, finasteride, dutasteride, bexlosteride, izonsteride, turosteride, episteride, dexamethasone, prednisone, leuprolide, goserelin, triptorelin, histrelin and estrogen. In some embodiments, the ADT is enzalutamide.

In some embodiments, the taxane is selected from the group consisting of paclitaxel, docetaxel, protaxel, larotaxel, cabazitaxel, Abraxane, Ortataxel, Genexol, DJ-927 and BMS-184476. In some embodiments, the taxane is docetaxel.

In some embodiments, the control sample is a normal prostate tissue or a primary prostate tumor. In some embodiments, the control sample is LNCaP cells.

In some embodiments, the probe comprises the sequence set forth in SEQ ID NO: 5 or 6.

The present disclosure also provides a kit comprising:
(a) a reagent for reverse transcription of an RNA molecule,
(b) two or more primers, wherein one primer comprises a polynucleotide that hybridizes to the sense strand of a DNA target that has a sequence selected from the group consisting of SEQ ID NO: 2, NO: 3 and NO: 4, and the other primer comprises a polynucleotide that hybridizes to the anti-sense strand of the DNA target, and (3) a reagent for amplification of a DNA sequence. In some particular embodiments, the primers comprise a primer comprising SEQ ID NO: 5 and a primer comprising SEQ ID NO: 6.

In another aspect, the present disclosure provides a method of measuring expression of KDM5D in a subject having prostate cancer, the method comprising measuring the binding of an antibody in a sample from the subject, wherein the antibody specifically binds to KDM5D, thereby measuring expression of KDM5D in the subject.

In some embodiments, the prostate cancer is a hormone-naive prostate cancer. In some embodiments, the prostate cancer is hormone-sensitive prostate cancer. In some embodiments, the prostate cancer is castration-resistant prostate cancer. In some embodiments, the prostate cancer is hormone-refractory prostate cancer. In some embodiments, the prostate cancer is metastatic.

In some embodiments, the subject is a human. In some embodiments, the sample is from a cancerous lesion. In certain embodiments, the sample comprises circulating tumor cells.

In some embodiments, the method further comprises administering to the subject a therapeutically effective amount of a taxane if the expression of KDM5D is the same as or higher than the reference expression level of KDM5D in a control sample. In some embodiments, the method further comprises administering to the subject a therapeutically effective amount of a taxane and an ADT if the expression of KDM5D is lower than the reference expression level of KDM5D in a control sample. In some embodiments, the ADT is selected from the group consisting of flutamide, nilutamide, enzalutamide, bicalutamide, ketonazole, abiraterone, abiraterone acetate, orteronel, finasteride, dutasteride, bexlosteride, izonsteride, turosteride, episteride, dexamethasone, prednisone, leuprolide, goserelin, triptorelin, histrelin and estrogen. In some embodiments, the ADT is enzalutamide.

In some embodiments, the taxane is selected from the group consisting of paclitaxel, docetaxel, protaxel, larotaxel, cabazitaxel, Abraxane, Ortataxel, Genexol, DJ-927 and BMS-184476. In some embodiments, the taxane is docetaxel.

In some embodiments, the control sample is a normal prostate tissue or a primary prostate tumor. In some embodiments, the control sample is LNCaP cells.

The present disclosure also provides a kit comprising an antibody that specifically binds to KDM5D and reagents for the detection of the antibody.

BRIEF DESCRIPTION OF THE DRAWINGS

FIG. 4 is a series of graphs showing histone modification genes that are differentially expressed in LAPC4 and LNCaP, wherein KDM5D is identified as a lead candidate.

FIG. 5 is a graph showing the expression levels of KDM5D protein in 10 prostate cancer cell lines.

FIG. 10 is a set of Western blot images showing co-immunoprecipitation between KDM5D and AR in the nuclear fraction of cell lysate.

FIG. 13 is a set of graphs showing clinical progression of prostate cancer in patients with higher versus lower KDM5D expression in the Grasso cohort. For each graph in parts A, B, and C, the upper curve is the survival curve of patients with high KDM5D expression ("High Gene Exp (n=15)"), and the lower curve is the survival curve of patients with low KDM5D expression ("Low Gene Exp (n=16)").

DETAILED DESCRIPTION

Figure 1:
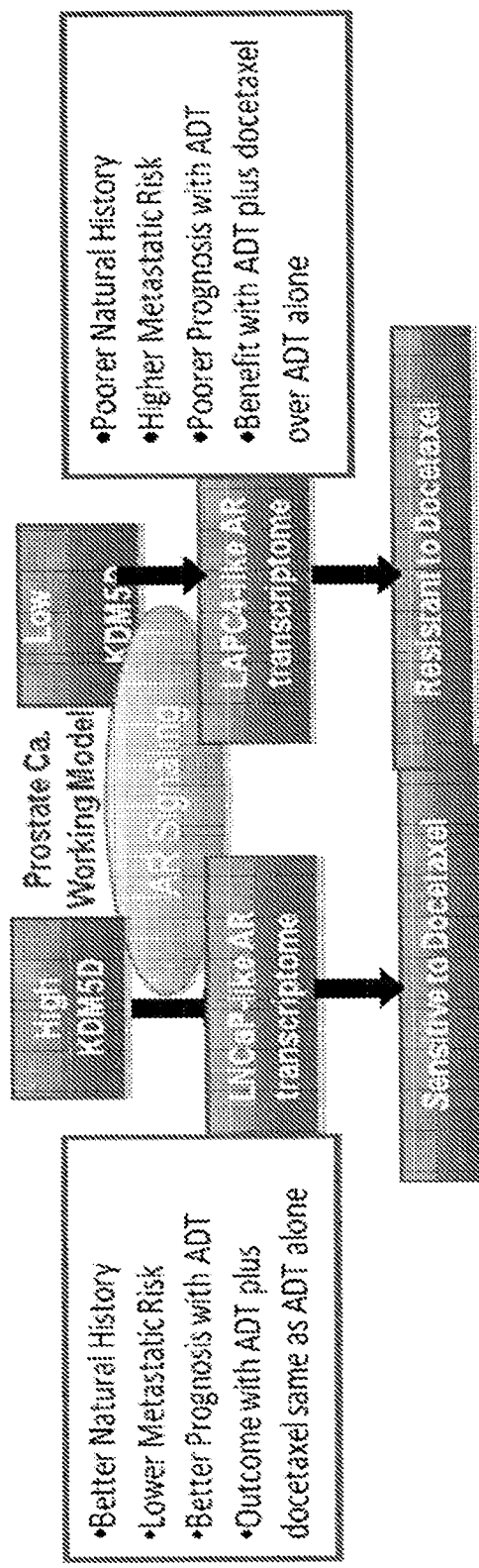
FIG. 1 is a diagram showing the relationship between KDM5D expression level, androgen receptor (AR)-dependent transcriptome, and sensitivity to docetaxel.

The present disclosure provides a correlation between KDM5D expression and androgen receptor (AR)-dependent taxane resistance of prostate cancer. A lower level of KDM5D is associated with reduced sensitivity of prostate cancer cells to a taxane in an androgen-supplemented environment. Growth inhibition of these cells can be achieved by a combination of taxane and androgen deprivation. In comparison, a higher level of KDM5D is associated with taxane sensitivity in the presence of androgen, wherein androgen deprivation or AR inhibition leads to no or little additional cytotoxicity.

The disclosure provides statistical evidence that KDM5D expression is significantly lower in metastatic prostate cancer than in normal prostate or primary prostate tumors. It also provides a correlation between lower KDM5D expression and more aggressive clinical course of prostate cancer in human patients.

In certain embodiments, the expression level of KDM5D is examined using a sample of prostate cancer that has been removed by surgery. The expression level is compared to a reference level. If it is the same or higher than the reference level, administration of a taxane and an ADT does not provide a higher likelihood of improvement than administration of a taxane without ADT or ADT without a taxane. In this case administration of either a taxane or ADT alone may be preferred over the combination to avoid docetaxel or ADT-associated side effects. If KDM5D expression level is lower than the reference level, administration of a taxane and an ADT provides a higher likelihood of improvement than administration of a taxane or ADT alone, and thus the combination therapy is preferred over a taxane single therapy or ADT single agent therapy.

In certain embodiments, the taxane is paclitaxel, docetaxel, cabazitaxel, protaxel, larotaxel, ortataxel, Abraxane and Genexol, DJ-927 or BMS-184476. In a preferred embodiment, the taxane is docetaxel.

In certain embodiments, the ADT is orchiectomy, prostatectomy, degarelix, abiraterone, leuprolide, goserelin, triptorelin, histrelin, flutamide, bicalutamide, nilutamide, enzalutamide, apalutamide, cyproterone, abiraterone, topilutamide, galeterone, orteronel, BAY1841788, ORM-15341, finasteride, dutasteride, bexlosteride, izonsteride, turosteride, episteride, an estrogen, megestrol, chlormadinone, ketoconazole, dexamethasone or prednisone. In a preferred embodiment, the ADT is enzalutamide.

In certain embodiments, the sample is examined while it is scored according to the Gleason pathological grading. In a preferred embodiment, the expression level of KDM5D is measured by immunohistochemistry. In another embodiment, one or more other tumor antigens (e.g. prostate-specific antigen) are examined simultaneously, either by a similar method or by a different method.

In certain embodiments, the comparison of KDM5D expression level with a reference level is followed by a treatment. Where KDM5D level is the same or higher than the reference level, and a taxane is to be administered for castration resistant prostate cancer, the treatment may continue, as taxane alone added to the ongoing castration. Where KDM5D level is lower than the reference level, an androgen receptor inhibitor is added to the ongoing taxane therapy to make the taxane more effective.

The treatment(s) can be combined with other therapies appropriate for the treatment of prostate cancer. Treatments for prostate cancer include prostactomy, cryotherapy, radiation therapy, ADT, chemotherapy and immunotherapy. Chemotherapy includes, but is not limited to, alkylating agents (e.g., nitrogen mustard, cyclophosphamide, melphalan, busulfan, dacarbazine, procarbazine, etc.), antimetabolites (e.g., methotrexate, mercaptopurine, thioguanine, fluorouracil, etc.), antibiotics (e.g., doxorubicin, daunorubicin, bleomycin, etc.)

and alkaloids (e.g., vincristine, vinblastine, vindesine, taxanes, etc.). Immunotherapy includes, but is not limited to, an agent that increases an immune response (e.g. a T cell checkpoint inhibitor) and a cancer vaccine (e.g. Sipuleucel-T). Any of these compounds can be co-administered with any of the therapies disclosed herein.

In certain embodiments, where KDM5D level is lower than the reference level, a lower dose of docetaxel than 75 mg/m.sup.2, the dose approved by FDA, is administered in combination with an ADT. In one embodiment, the dose of docetaxel is about 20 to 70 mg/m.sup.2. In another embodiment, the dose of docetaxel is about 20 to 50 mg/m.sup.2.

As used herein, a "subject" within the context of the present invention encompasses, but is not limited to, a mammal, e.g. a human, a domestic animal or a livestock including a cat, a dog, a cattle and a horse.

"A prostate cancer" encompasses, but is not limited to, a localized primary prostate tumor, a metastatic prostate cancer, a hormone-naive prostate cancer, a hormone-sensitive prostate cancer, a castration-resistant prostate cancer, a prostate adenocarcinoma, and a neuroendocrine prostate cancer.

"A hormone-naive prostate cancer" encompasses, but is not limited to, a prostate cancer that has not been treated with an ADT.

"A hormone-sensitive prostate cancer" encompasses, but is not limited to, a prostate cancer whose growth can be inhibited by an ADT.

"A castration-resistant prostate cancer" encompasses, but is not limited to, a prostate cancer that is able to grow and/or progress despite an ADT.

"A hormone-refractory prostate cancer" encompasses, but is not limited to, a prostate cancer whose growth and/or progression are not inhibited by an ADT.

"A metastatic prostate cancer" encompasses, but is not limited to, a cancer of prostate origin that spreads to one or more other parts of the body.

"A sample" encompasses, but is not limited to, a sample from a cancerous lesion, a sample from a cancer draining lymph node, a body fluid such as blood, serum, plasma, urine, semen, lymph, and peritoneal fluid.

"A cancerous lesion" encompasses, but is not limited to, a tissue, organ or structure wherein prostate cancer locates. It may be in or attached to a prostate, or at a metastatic site.

"Circulating tumor cells" encompass, but are not limited to, cells with a tumor origin in the circulating blood stream. In certain embodiments, the circulating tumor cells are enriched from the blood (e.g., by affinity to certain tumor cell markers).

"The expression level of KDM5D" means the amount of KDM5D mRNA or the amount of KDM5D protein. The amount of KDM5D mRNA, including SEQ ID NO: 2, 3 and 4, can be measured by polymerase chain reaction (PCR) following reverse transcription, nucleic acid hybridization methods such as microarray, and RNA sequencing methods. The primers for the method of PCR measurement (SEQ ID NO: 5 and 6) amplify all three transcript variants of KDM5D (SEQ ID NO: 2, 3, and 4). The amount of KDM5D protein (SEQ ID NO: 7, 8, and 9) can be measured by mass spectrometry or by antibody-based methods, such as immunohistochemistry, enzyme-linked immunosorbent assay (ELISA), Western blotting, flow cytometry, and immuno-electron microscopy.

"A reference level" means the amount of KDM5D mRNA or protein in a normal organ, tissue or cell, which encompasses but is not limited to a normal prostate, a primary prostate tumor or a prostate cancer from a subject who has not received an ADT/taxane combination therapy. "A reference level" also encompasses the amount of KDM5D mRNA or protein in an immortalized cell, such as an LNCaP cell, a 22RV1 cell, a PC3 cell and a DU145 cell in 10% fetal bovine serum (FBS) media.

"The same as or higher than the reference level" means the amount of KDM5D mRNA or protein is higher than 99%, 100%, 110%, 120%, 130%, 140%, 150%, 200%, 300%, 500% or 1000% of the reference level.

"Lower than the reference level" means the amount of KDM5D mRNA or protein is lower than 95%, 90%, 80%, 70%, 60%, 50%, 40%, 30%, 20% or 10% of the reference level.

"A symptom of a prostate cancer" encompasses, but is not limited to, difficulty urinating, blood in urine, erectile dysfunction, pain in the hips, pain in the back, pain the chest, weakness, numbness and incontinence.

"Improvement of a symptom of prostate cancer" includes, but is not limited to, alleviation of a symptom of a prostate cancer, a shrink of cancer size, a reduction of cancer-associated inflammation and/or cachexia, an absence of cancer growth during a period within which an untreated such cancer would grow, an absence of metastatic progression during a period within which an untreated such cancer would metastasize or expand.

"A decrease in cancer load" includes, but is not limited to, a decreased number of cancer cells, a decreased size of a tumor, and/or a decreased amount of cancer in the body.

The cancer load may be determined by measuring the tumor size and/or by measuring a tumor antigen. A commonly used tumor antigen for prostate cancer is prostate-specific antigen (PSA).

"An androgen deprivation therapy" encompasses, but is not limited to, (1) surgical castration e.g. orchiectomy; (2) medical castration e.g. luteinizing hormone-releasing hormone (LHRH) agonists and antagonists, including degarelix, abiraterone, leuprolide, goserelin, triptorelin and histrelin; (3) androgen receptor antagonists including flutamide, bicalutamide, nilutamide, enzalutamide, apalutamide, cyproterone, abiraterone, topilutamide, galeterone, orteronel, BAY1841788, ORM-15341; (4) 5.alpha.-reductase inhibitors including finasteride, dutasteride, bexlosteride, izonsteride, turosteride and episteride; and (5) other androgen-suppressing drugs including estrogens, megestrol, chlormadinone, ketoconazole, dexamethasone and prednisone. These compounds can be used in their final non-salt form or in the form of a pharmaceutically acceptable salt, which can be derived from various organic and inorganic acids and bases by procedures known in the art.

"A therapeutically effective amount" of surgical, medical castration or other androgen-suppressing drugs according to the invention is an amount that is sufficient to reduce the level of testosterone or dihydrotestosterone. "A therapeutically effective amount" of a 5.alpha.-reductase inhibitor is an amount that is sufficient to reduce the level of dihydrotestosterone. "A therapeutically effective amount" of an androgen receptor antagonist is an amount that is sufficient to improve a symptom of prostate cancer either alone or in combination with one or more other therapies.

"A taxane" encompasses, but is not limited to, paclitaxel, docetaxel, cabazitaxel, protaxel, larotaxel, ortataxel, Abraxane and Genexol, DJ-927 and BMS-184476. These compounds can be used in their final non-salt form or in the form of a pharmaceutically acceptable salt, which can be derived from various organic and inorganic acids and bases by procedures known in the art.

"A therapeutically effective amount" of a taxane refers to an amount sufficient to improve a symptom of prostate cancer either alone or in combination with one or more other therapies. It depends on a number of factors, including, for example, the age and weight of the animal, the precise condition that requires treatment, and its severity, the nature of the formulation and the method of administration, and is ultimately determined by the treating doctor or vet. However, an effective amount of a taxane according to the invention for the treatment of prostate cancer is generally in the range from 1 to 1000 mg/m.sup.2 of body surface area of the recipient per infusion every 21 days and particularly typically at 10-200 mg/m.sup.2 of body surface area of the recipient per infusion every 21 days. Thus, the actual amount per infusion for an adult human with about 1.7 m.sup.2 of body surface area is about 17-340 mg. An effective amount of a salt or solvate or of a physiologically functional derivative thereof can be determined as the fraction of the effective amount of the compound according to the invention per se.

"A reagent for reverse transcription of an RNA molecule" encompasses, but is not limited to, a reverse transcriptase, an RNase inhibitor, a primer that hybridizes to a KDM5D mRNA sequence, a primer that hybridizes to an adenosine oligonucleotide, and a buffer solution that provides a suitable chemical environment for optimum activity, binding kinetics, and stability of the reverse transcriptase. The reagents can be provided in the form of a solution, a concentrated solution, or powder.

"A reagent for amplification of a DNA sequence" includes, but is not limited to, (1) a heat-stable DNA polymerase, (2) deoxynucleotide triphosphates (dNTPs), (3) a buffer solution, providing a suitable chemical environment for optimum activity, binding kinetics, and stability of the DNA polymerase, (4) bivalent cations such as magnesium or manganese ions, and (5) and monovalent cations, such as potassium ions. The reagents can be provided in the form of a solution, a concentrated solution, or powder. The target DNA sequence can be amplified by polymerase chain reaction (PCR). PCR relies on thermal cycling, which consists of cycles of repeated heating and cooling of the reaction for DNA denaturation, annealing and enzymatic elongation of the amplified DNA. First, the strands of the DNA are separated at a high temperature in a process called DNA melting or denaturing. Next, the temperature is lowered, allowing the primers and the strands of DNA to selectively anneal, creating templates for the polymerase to amplify the target DNA. Next, at a working temperature of the DNA polymerase, template-dependent DNA synthesis occurs. These steps are repeated.

"A primer" refers to a short, single-stranded DNA sequence that binds to a target DNA sequence and enables addition of new deoxyribonucleotides by DNA polymerase at the 3' end. According to certain embodiments, the forward primer is 18-35, 19-32 or 21-31 nt in length. The nucleotide sequence of the forward primer is not limited, so long as it specifically hybridizes with part of or an entire target site, and its Tm value may be within a range of 50.degree. C. to 72.degree. C., in particular may be within a range of 58.degree. C. to 61.degree. C., and may be within a range of 59.degree. C. to 60.degree. C. The nucleotide sequence of the primer may be manually designed to confirm the Tm value using a primer Tm prediction tool.

"An antibody that specifically binds to KDM5D" encompasses, but is not limited to, an antiserum, an polyclonal antibody, an monoclonal antibody, an antigen-binding fragment of an antibody, a variable fragment of an antibody, and a protein that binds to an epitope of KDM5D specifically.

"Reagents for the detection of the antibody" encompasses, but are not limited to, a fluorescent agent, a catalyst that catalyzes a luminescent reaction, a catalyst that catalyzes a colorimetric reaction, and an electron-dense agent. The reagents may be linked to the antibody covalently or associated with the antibody noncovalently through an intermolecular interaction or through one or more intermediates. The intermediate includes an agent comprising a moiety that binds to the antibody.

By "RNA" is meant a sequence of two or more covalently bonded, naturally occurring or modified ribonucleotides. One example of a modified RNA included within this term is phosphorothioate RNA.

By "DNA" is meant a sequence of two or more covalently bonded, naturally occurring or modified deoxyribonucleotides.

By a "nucleic acid" is meant any two or more covalently bonded nucleotides or nucleotide analogs or derivatives. As used herein, this term includes, without limitation, DNA, RNA, and PNA. The term "nucleic acid" may include a modified nucleic acid, and, accordingly, nucleic acid and modified nucleic acid may be used interchangeably.

In one aspect, the present disclosure provides a method of measuring expression of KDM5D in a subject having prostate cancer. In certain embodiments, the method comprises measuring the binding of a probe in a sample from the subject, wherein the probe specifically hybridizes to a DNA having the sequence set forth in SEQ ID NO: 2, 3, or 4, thereby measuring expression of KDM5D in the subject. In certain embodiments, the probe comprises a polynucleotide that hybridizes to the sense strand of a DNA target that has a sequence selected from the group consisting of SEQ ID NOs: 2-4. In certain embodiment, the sample from the subject comprises a nucleic acid (e.g., DNA) from the subject. In certain embodiments, the sample from the subject comprises a nucleic acid (e.g., DNA) amplified from a nucleic acid (e.g., DNA, RNA) from the subject.

In certain embodiments, the method comprises measuring the binding of an antibody in a sample from the subject, wherein the antibody specifically binds to KDM5D, thereby measuring expression of KDM5D in the subject. In certain embodiments, the antibody is conjugated (e.g., covalently conjugated) to a detection moiety. In certain embodiments, the binding of the antibody in the sample is measured by contacting the antibody with the sample, optionally further comprising contacting a molecule with the sample, wherein the molecule comprises a detection moiety. In certain embodiments, the detection moiety is a fluorescent moiety. In certain embodiments, the detection moiety is an enzyme that catalyzes a chemical reaction, wherein the chemical reaction causes a change in a signal. In certain embodiments, the signal is an optical signal (e.g., absorbance, fluorescence, and luminescence).

Furthermore, in accordance with the present disclosure there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

The present disclosure also provides recombinant expression vectors which include the synthetic, genomic, or cDNA-derived nucleic acid fragments of the invention, i.e. polynucleotides encoding the mabs of the invention. The nucleotide sequence coding for any of the sequences provided herein can be inserted into an appropriate expression vector, i.e., a vector that contains the necessary elements for the transcription and translation of the inserted protein-coding sequence. The necessary transcriptional and translational signals can also be supplied by the native or source gene and/or its flanking regions.

A variety of host vector systems may be utilized to express the recombinant expression vectors of the invention. These include, but are not limited to, mammalian cell systems infected with recombinant virus (e.g., vaccinia virus, adenovirus, retroviruses, etc.); mammalian cell systems transfected with recombinant plasmids; insect cell systems infected with recombinant virus (e.g., baculovirus); microorganisms such as yeast containing yeast expression vectors, or bacteria transformed with recombinant bacteriophage DNA, recombinant plasmid DNA, or cosmid DNA (see, for example, Goeddel, 1990).

Mammalian expression vectors may comprise non-transcribed elements such as origin of replication, a suitable promoter and enhancer linked to the recombinant nucleic acid to be expressed, and other 5' or 3' flanking sequences such as ribosome binding sites, a polyadenylation sequence, splice donor and acceptor sites, and transcriptional termination sequences.

The transcriptional and translational control sequences in mammalian expression vector systems to be used in transforming vertebrate cells may be provided by viral sources. For example, commonly used promoters and enhancers are derived from Polyoma virus, Adenovirus, Simian Virus 40 (SV40), and human cytomegalovirus, including the cytomegalovirus immediate-early gene 1 promoter and enhancer (CMV).

The following examples are provided to further elucidate the advantages and features of the present application, but are not intended to limit the scope of the application. The examples are for illustrative purposes only.

EXAMPLES

Example 1

Figure 2:
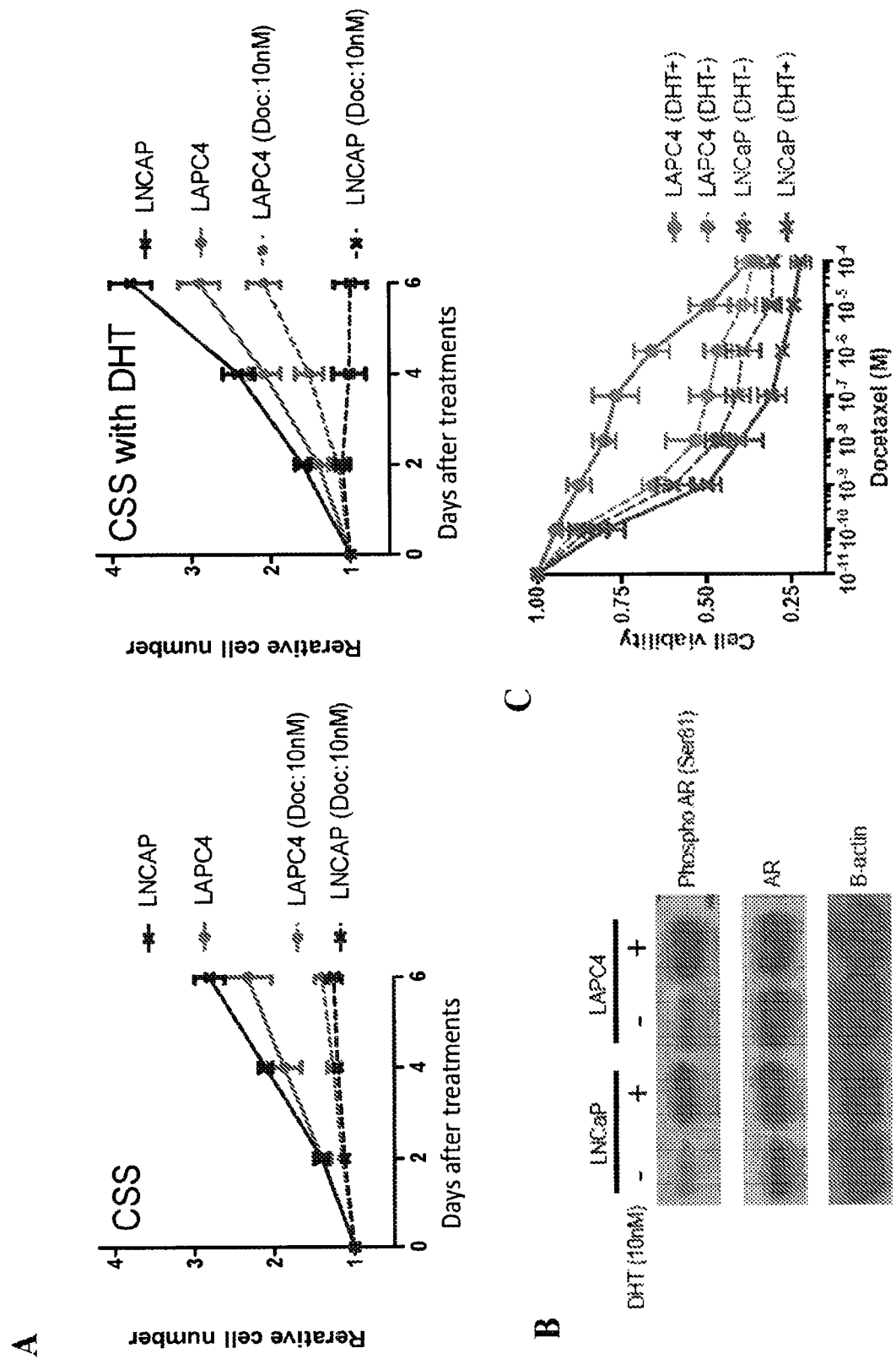
FIG. 2 is a series of graphs showing the toxicity of docetaxel on two prostate cancer cell lines, LAPC4 and LNCaP, in the presence or absence of dihydro-testosterone (DHT).
Figure 2:
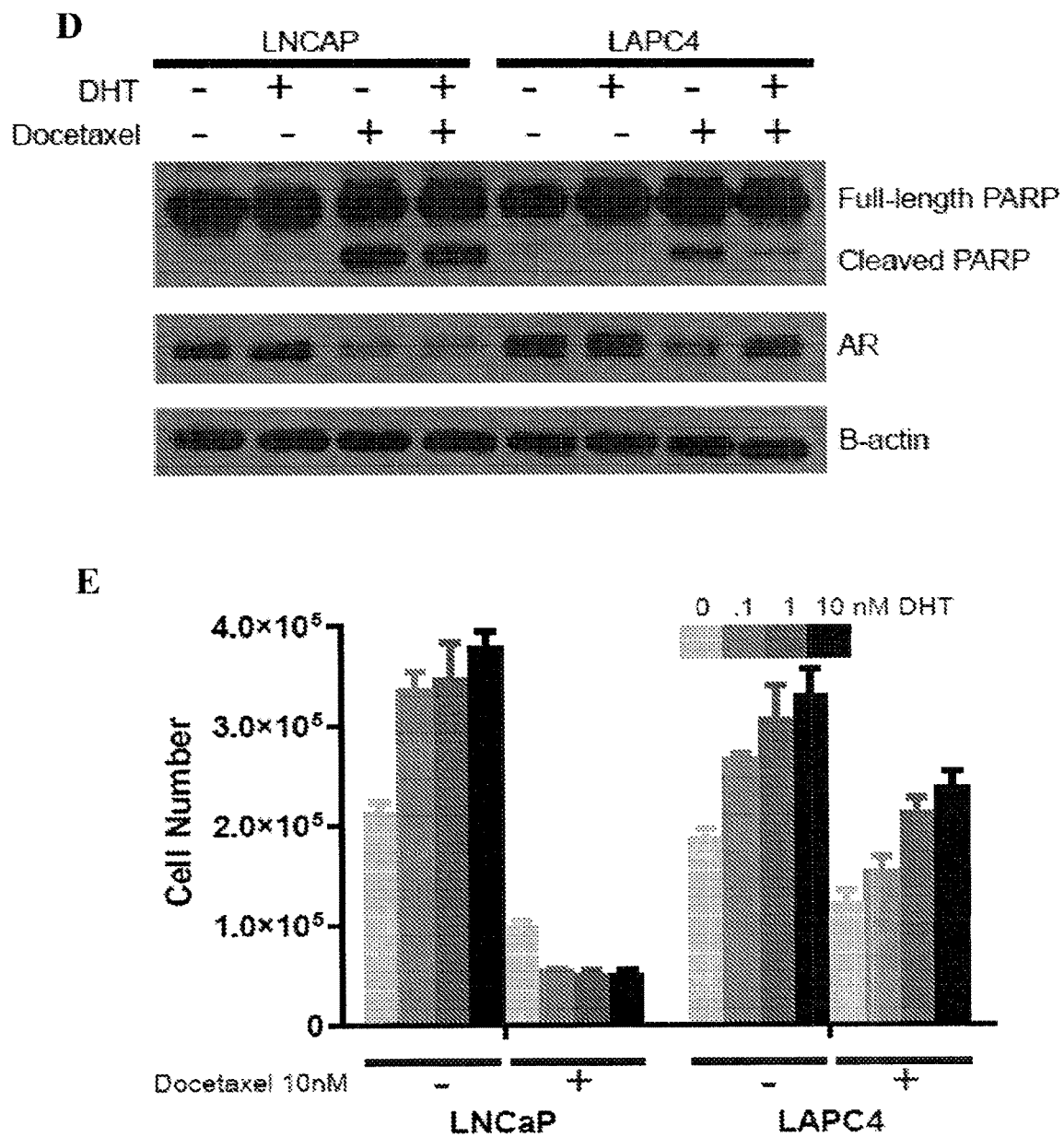

The Sensitivity to Docetaxel of LAPC4 Cells, but Not of LNCaP Cells, was Dependent on the Absence of Androgen Receptor Signaling To interrogate the differential sensitivity to docetaxel of prostate cancer cells, two prostate cancer cell lines, LNCaP and LAPC4, were compared. As shown in FIG. 2, part A, both cell lines were sensitive to 10 nM docetaxel in the absence of dihydro-testosterone (DHT), a ligand of androgen receptor (AR). However, the activation of AR by 10 nM DHT led to a restoration of cell growth in the presence of docetaxel in LAPC4 cells but not LNCaP cells, though AR was expressed and activated (as indicated by Ser 81 phosphorylation) in both cell lines (FIG. 2, part B). The viability of LAPC4 cells in a range of 0.01 nM to 0.1 mM of docetaxel, as measured by Trypan Blue exclusion, was markedly increased by DHT, whereas the viability of LNCaP cells against docetaxel was not significantly affected by DHT (FIG. 2, part C). PARP cleavage, a marker of apoptosis, was also specifically reduced by DHT in LAPC4 cells upon docetaxel treatment (FIG. 2, part D). The impact of DHT treatment on the docetaxel sensitivity of LAPC4 was dose-dependent (FIG. 2, part E).

Figure 3:
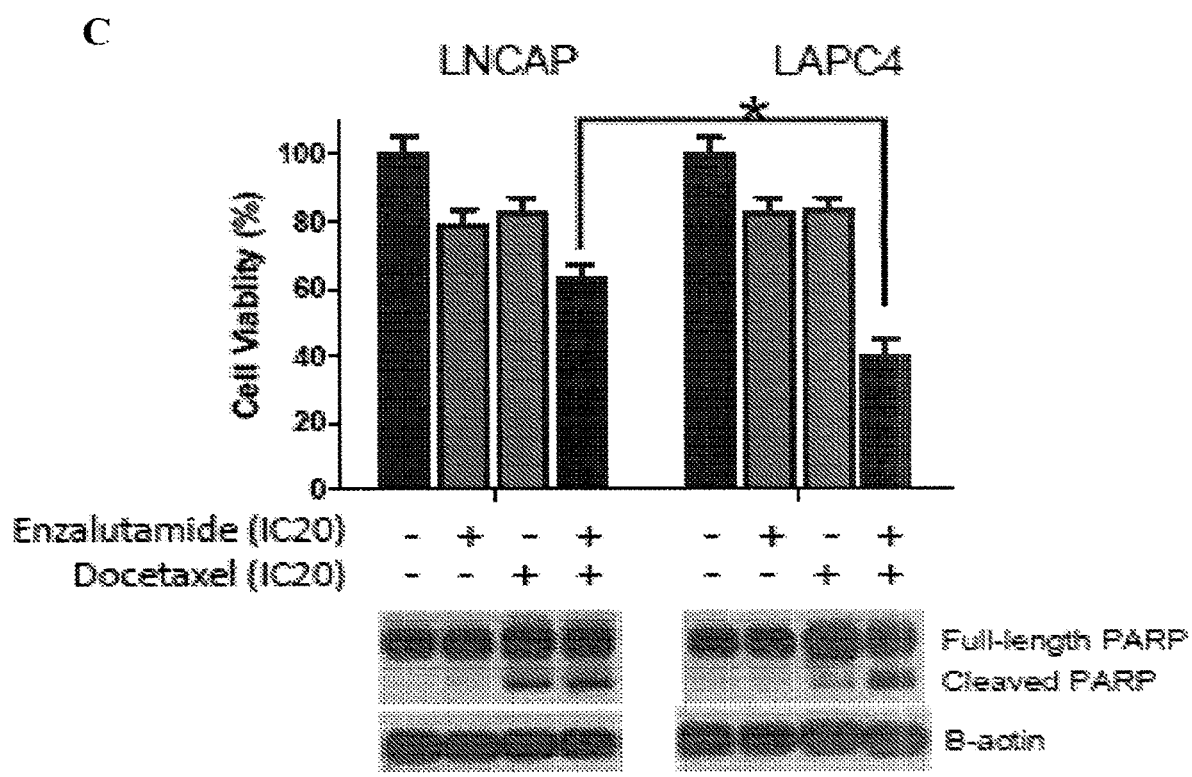
FIG. 3 is a series of graphs showing the toxicity of docetaxel on two prostate cancer cell lines, LAPC4 and LNCaP, in the presence or absence of AR antagonist enzalutamide.

To demonstrate that the DHT-induced docetaxel resistance in LAPC4 is mediated by AR signaling, we examined whether blocking AR activity in LAPC4 by enzalutamide, an AR antagonist, could inhibit DHT-induced docetaxel insensitivity. Despite the presence of a physiologically high concentration of docetaxel (10 nM), LAPC4 cells proliferated with DHT stimulation. Enzalutamide treatment abolished DHT-induced AR activation (FIG. 3, part B) and resensitized the cells to docetaxel in the presence of DHT (FIG. 3, part A), suggesting that the involvement of AR signaling in DHT modulated docetaxel resistance in LAPC4. The viability of LAPC4 cells treated with docetaxel in DHT supplemented media was substantially reduced by enzalutamide. An IC.sub.20 concentration of docetaxel (5 nM) and an IC.sub.20 concentration of enzalutamide (20 .mu.M) inhibited the growth of LAPC4 cells by about 60% after 6 days of treatment. In comparison, an IC.sub.20 concentration of docetaxel (0.5 nM) and an IC.sub.20 concentration of enzalutamide (10 .mu.M) inhibited the growth of LNCaP cells by about 40% after 6 days of treatment (FIG. 3, part C).

Example 2

KDM5D was Differentially Expressed in LAPC4 and LNCaP Cells

The results in Example 1 suggest that some prostate cancer cells, like LAPC4, may activate AR regulated genes which contribute to docetaxel resistance, and inhibition of AR signaling may sensitize these cells to docetaxel. In an effort to identify master regulators of the AR-dependent genes, RNA sequencing analyses were performed using LAPC4 and LNCaP cells cultured with or without DHT exposure for 48 hours. The analyses were focused on 236 genes in four epigenetic GO terms (GO:0016573 histone acetylation, GO:0016575 histone deacetylation, GO:0016571 histone methylation, and GO:0016577 histone demethylation).

Seven genes were identified with Bonferroni correction comparing mRNA expression level in those cell lines (X axis) and adjusted P value (Y axis) (FIG. 4, part A). Knockdown of these seven genes by siRNA (small-interfering RNA) was performed in LNCaP or LAPC4, based on the expression of the relevant gene. Of the seven genes, only knockdown of KDM5D in LNCaP significantly altered docetaxel sensitivity in the presence of 10 nM DHT compared with an siRNA negative control (GI50 10.46.+−.1.27 and 1.28.+−.0.79 nM in si-KDM5D and si-control, respectively, logtwofold change (Log 2FC) 3.19.+−.0.74] (FIG. 4, part B).

The differential expression of DKMSD across prostate cancer cell lines was also demonstrated at the protein level. LAPC4 expressed a lower amount of KDM5D than other cell lines such as LNCaP in 10% FBS media (FIG. 5).

Example 3

KDM5D Antagonized AR-Dependent Docetaxel Resistance

Figure 6A:
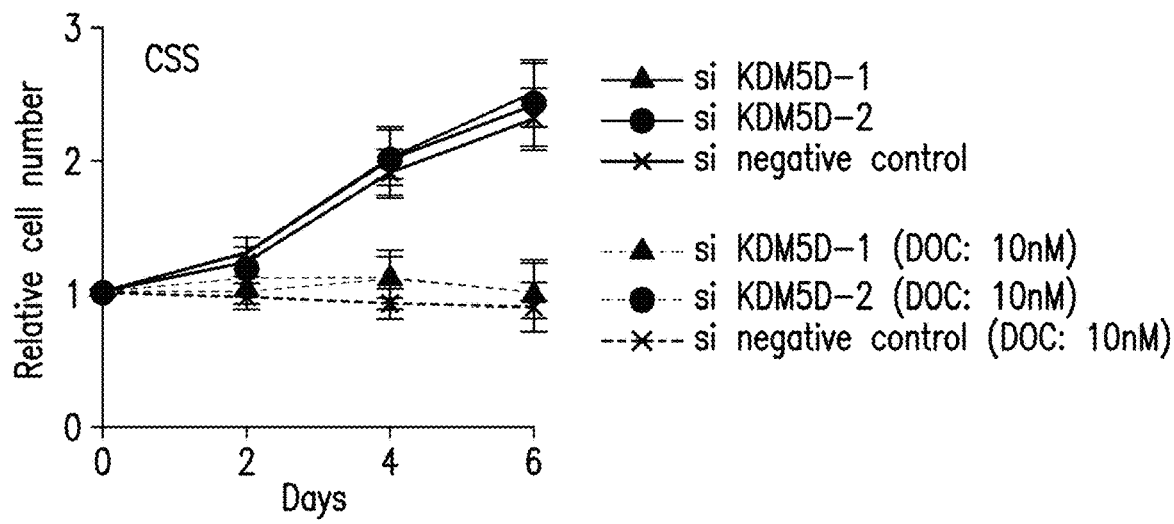
FIG. 6A, FIG. 6B, and FIG. 6C are a series of graphs showing an increase of DHT-dependent resistance to docetaxel of LNCaP cells expressing KDM5D siRNAs.
Figure 6B:
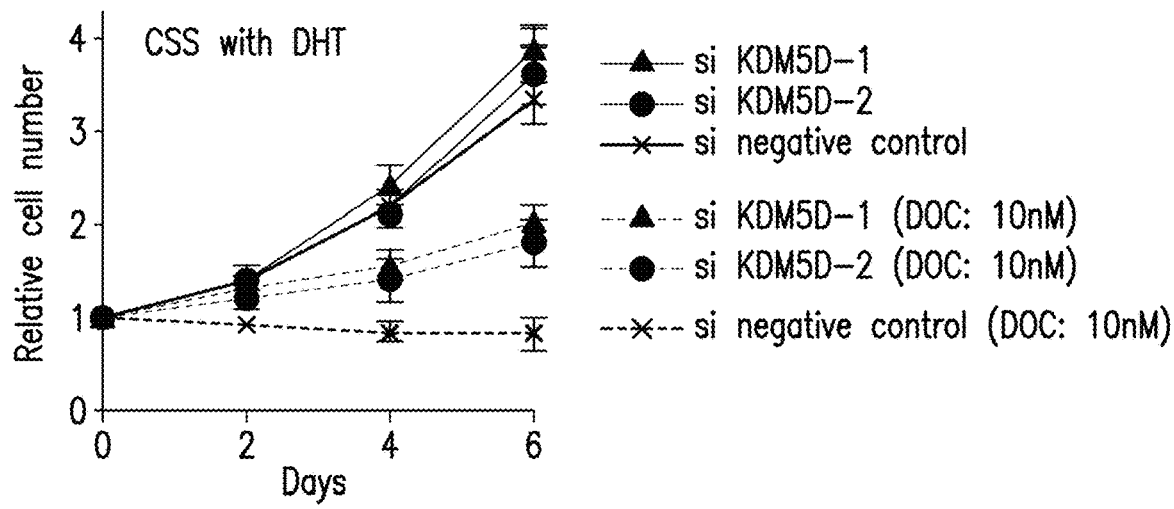
Figure 6C:
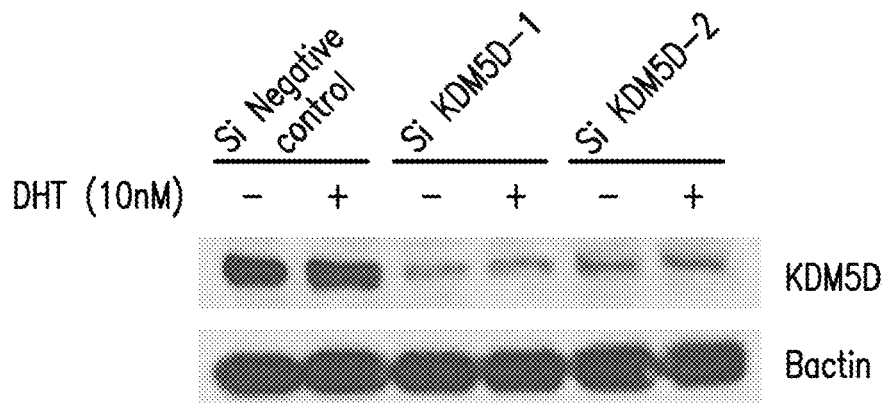

To explore whether the higher expression level of KDM5D could account for the higher sensitivity of LNCaP cells to docetaxel in DHT supplemented media, the effect of KDM5D knockdown was examined. As shown in FIG. 6, knockdown of KDM5D with siRNAs reduced docetaxel sensitivity of LNCaP cells cultured in DHT supplemented media.

The change in sensitivity by KDM5D siRNA did not occur in the absence of DHT, suggesting that KDM5D is a master regulator of the AR dependent genes involved in docetaxel sensitivity.

Figure 7A:
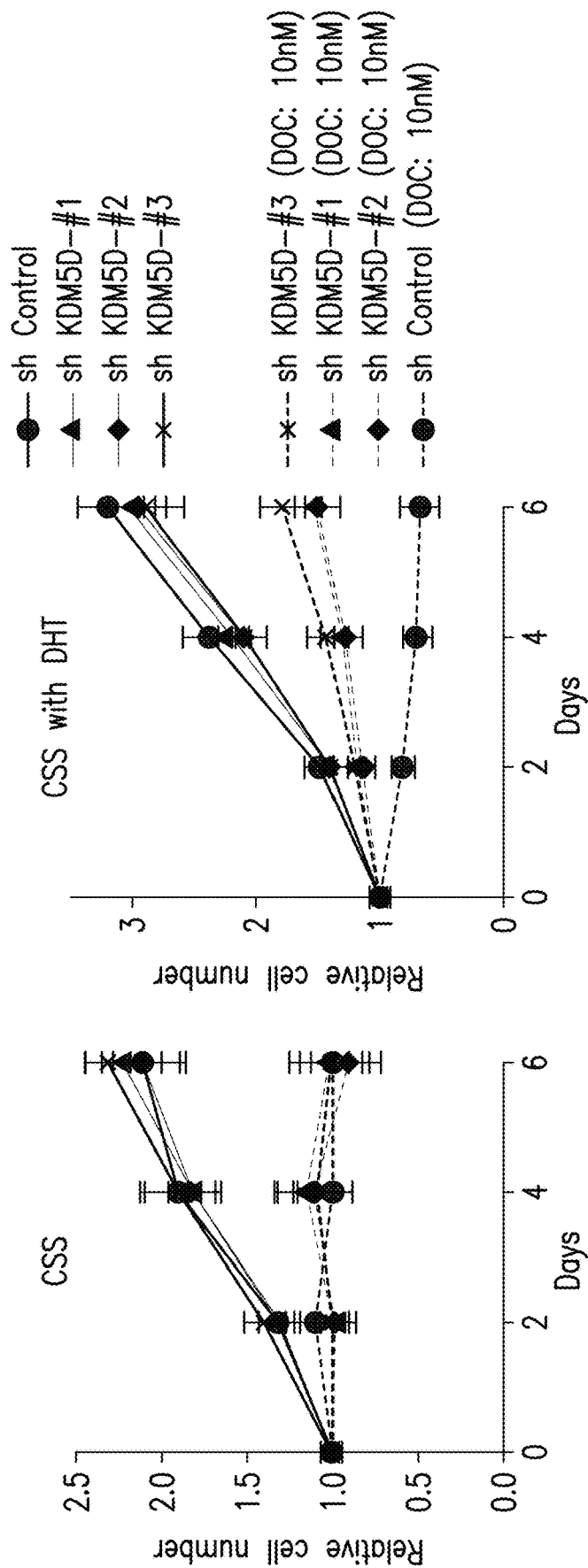
FIG. 7A, FIG. 7B, and FIG. 7C are a series of graphs showing an increase of DHT-dependent resistance to docetaxel of LNCaP cells expressing KDM5D shRNAs.
Figure 7B:
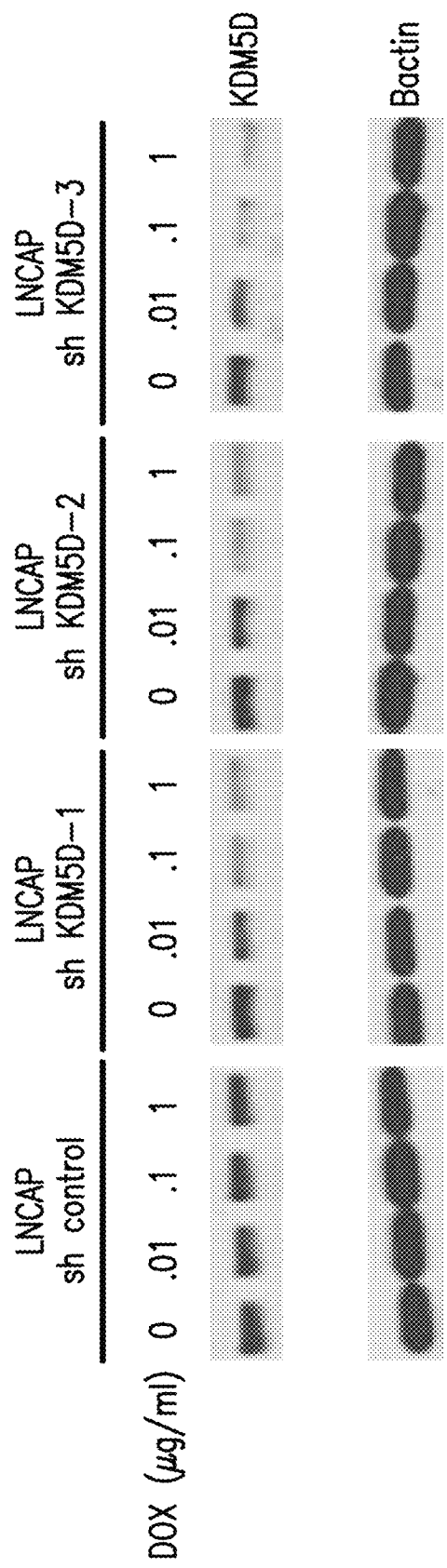
Figure 7C:
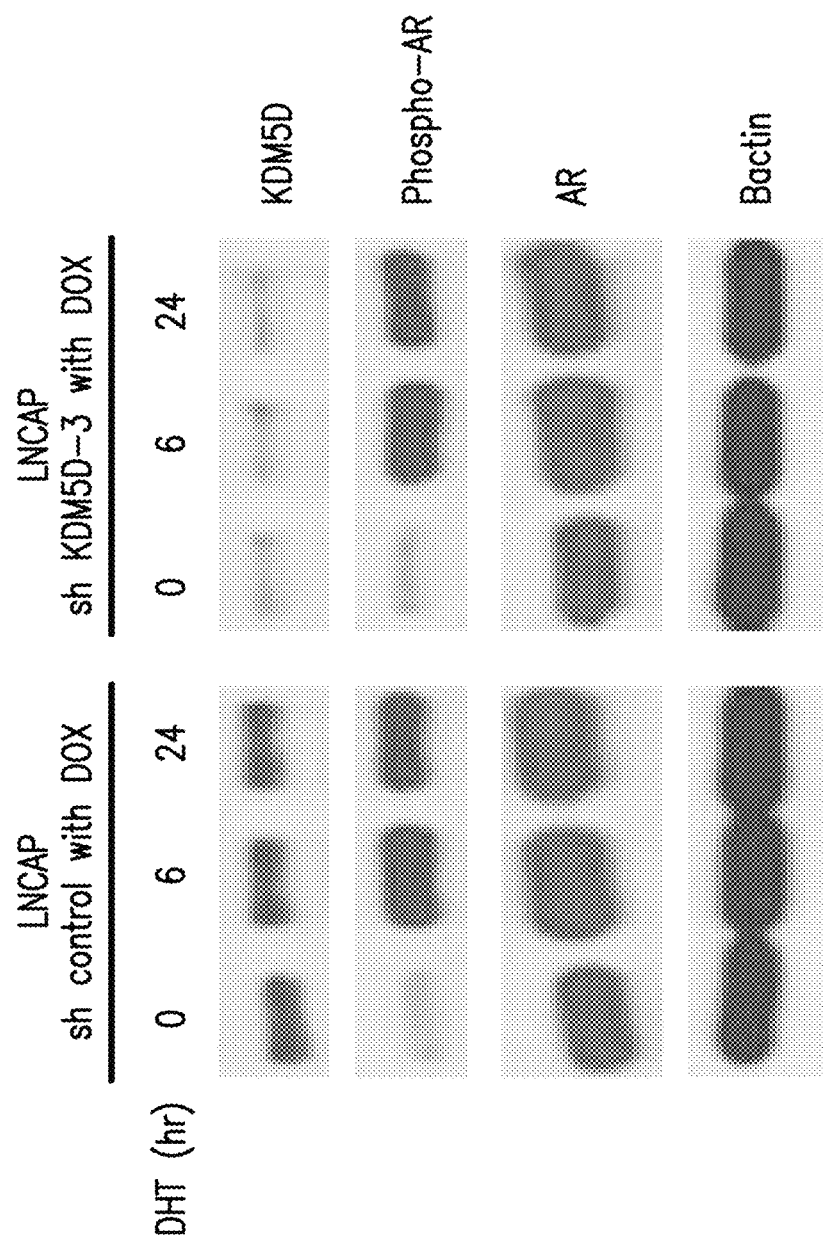

The results were confirmed using Tet-On inducible KDM5D shRNAs. As shown in FIG. 7, part B, all three shRNAs effectively reduced KDM5D expression in LNCaP cells after being induced by 0.1 .mu.g/ml doxycycline for 6 days. All these shRNAs reduced the docetaxel sensitivity of LNCaP cells cultured in DHT supplemented media, whereas the sensitivity of the cells in DHT-free media was not affected (FIG. 7, part A). Notably, KDM5D did not alter AR protein expression or phosphorylation in LNCaP cells that were exposed to 10 nM DHT after a 48-hour culture in DHT-free media (FIG. 7, part C). Instead, KDM5D may antagonize AR-dependent docetaxel resistance by modulating the expression of AR-regulated genes.

Example 4

Overexpression of KDM5D Restores Docetaxel Sensitivity

Figure 8A:
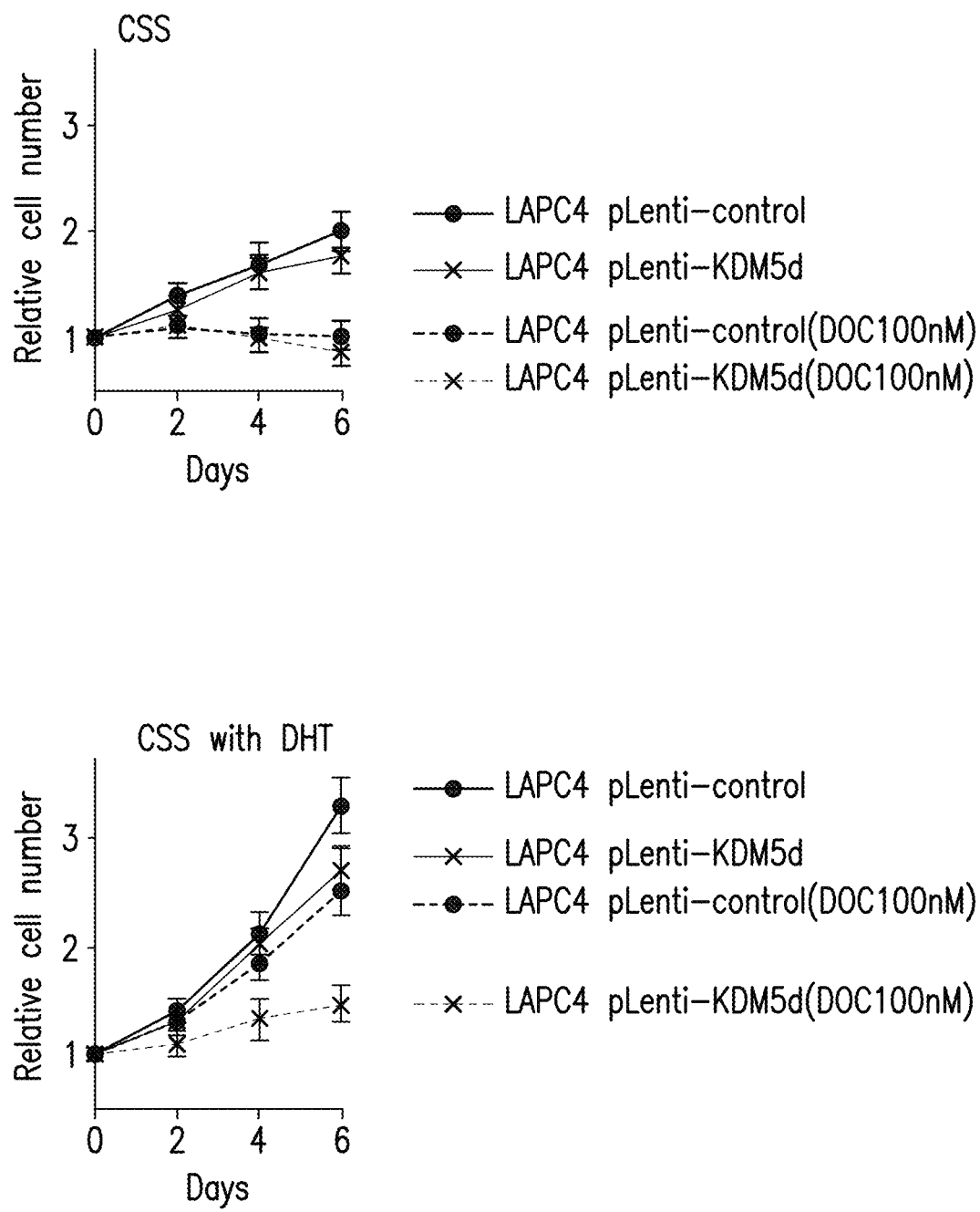
FIG. 8A, FIG. 8B, and FIG. 8C are a series of graphs showing a reduction of DHT-dependent resistance to docetaxel of LAPC4 cells overexpressing KDM5D.
Figure 8B:
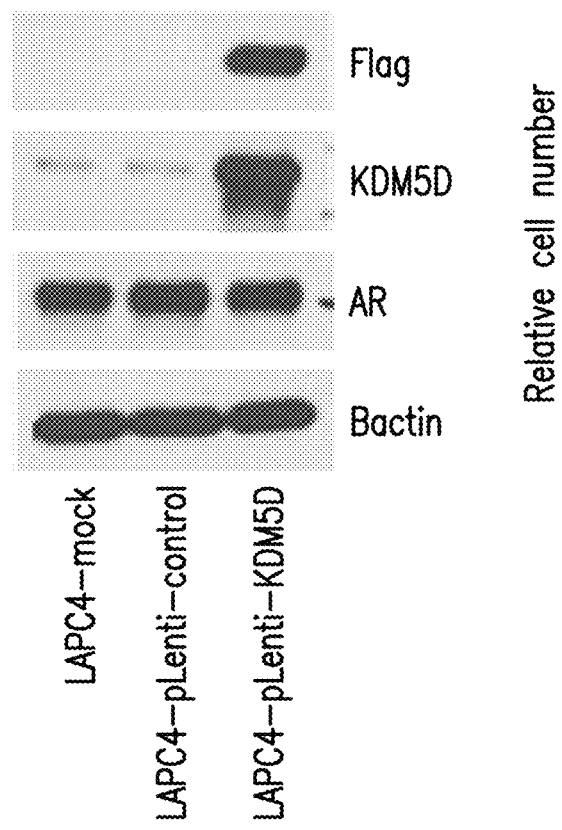
Figure 8C:
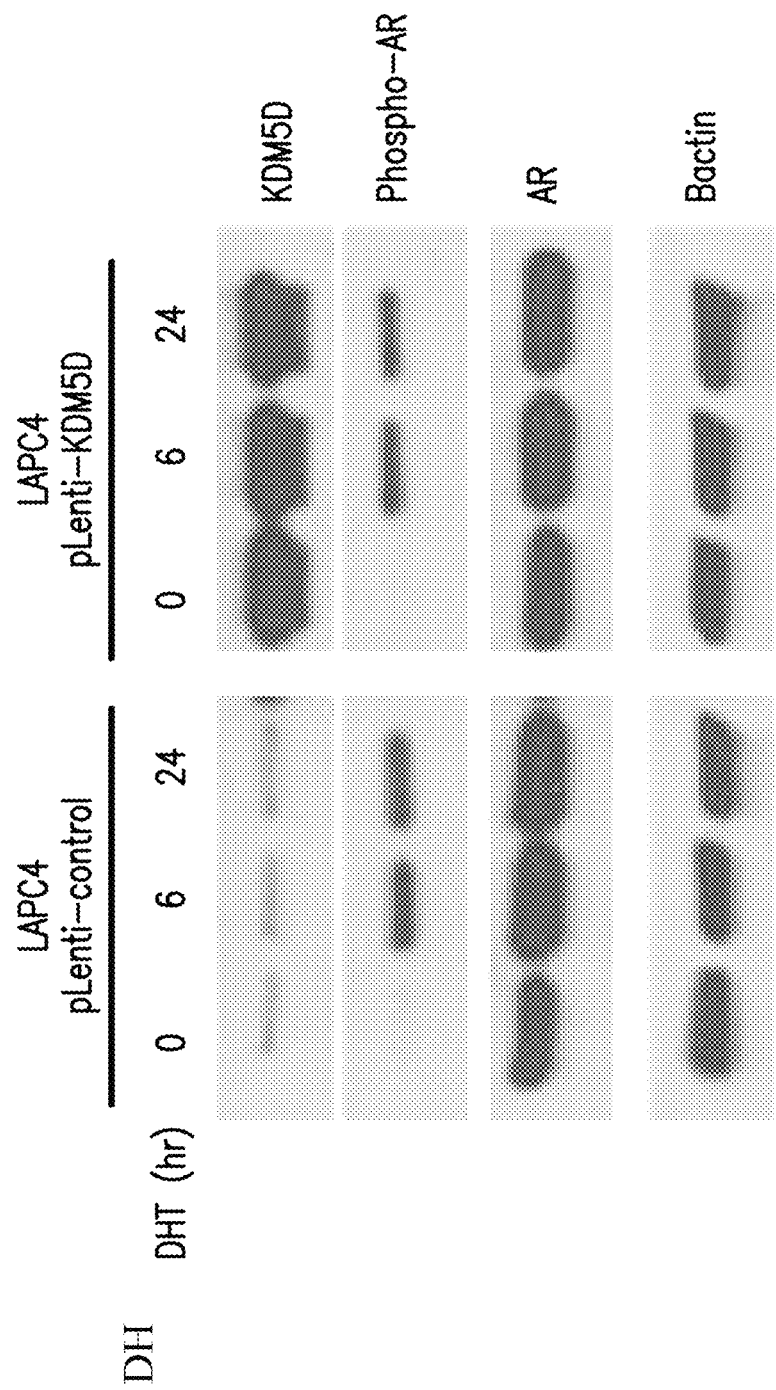

To explore whether the lower expression level of KDM5D could account for the lower sensitivity of LAPC4 cells to docetaxel in DHT supplemented media, the effect of KDM5D overexpression was examined. As shown in FIG. 8, parts A and B, overexpression of KDM5D restored docetaxel sensitivity of LAPC4 cells cultured in DHT supplemented media. KDM5D did not alter AR protein expression or phosphorylation in LNCaP cells that were exposed to 10 nM DHT after a 48-hour culture in DHT-free media (FIG. 8, part C). Instead, KDM5D may modulate the expression of AR-regulated genes that contribute to docetaxel resistance.

Figure 9:
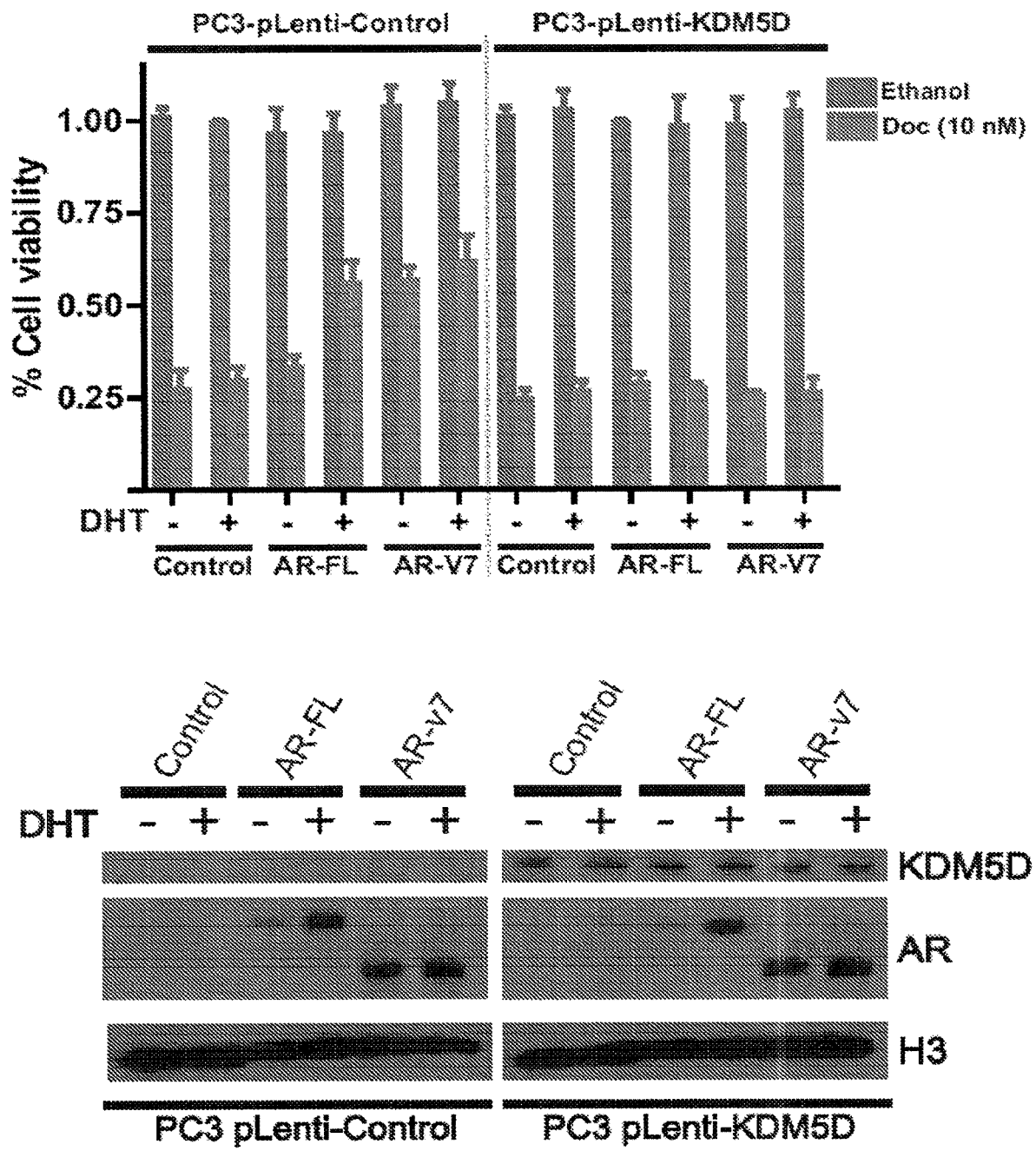
FIG. 9 is a graph and an image of Western blot showing that KDM5D and AR cooperate in rendering docetaxel sensitivity.
Figure 11A:
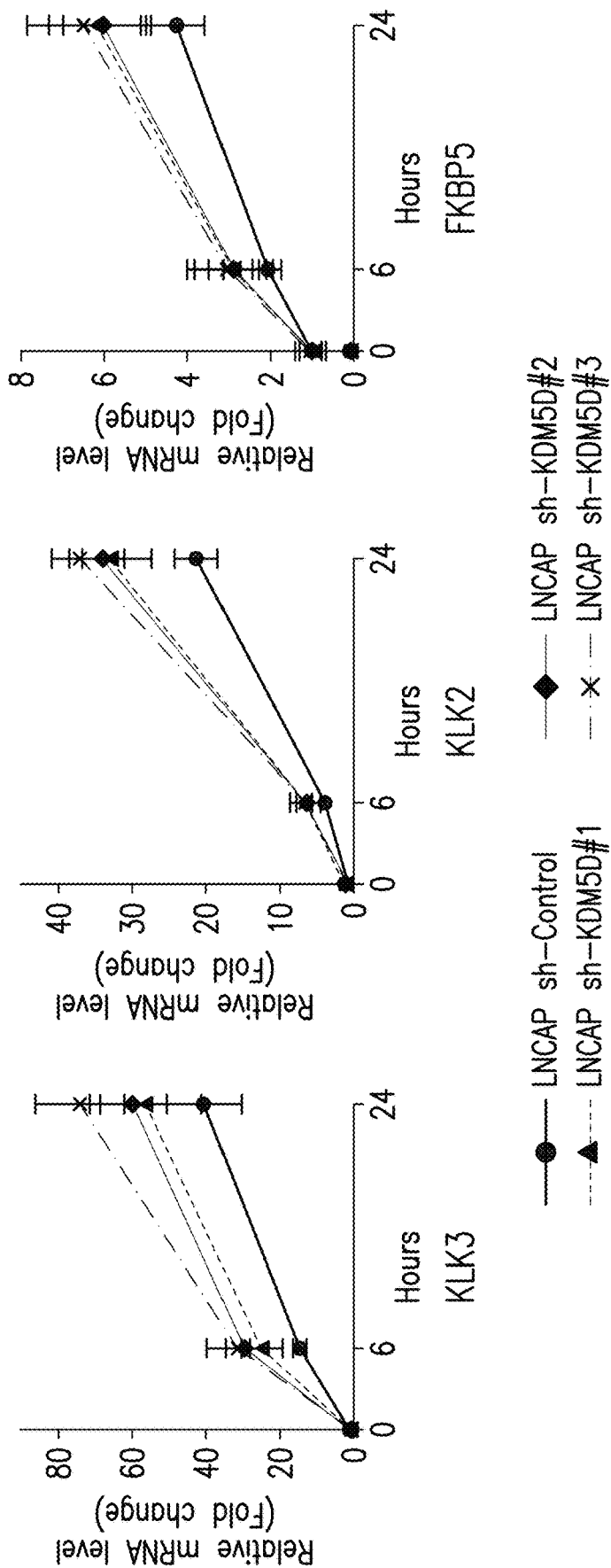
FIG. 11A, FIG. 11B, FIG. 11C, FIG. 11D, FIG. 11E, and FIG. 11F are a set of graphs showing regulation of AR-driven transcription by KDM5D. In the H3K4me3-ChIP bar graphs in FIG. 11B, FIG. 11C, and FIG. 11D, for each probe ("P1," "P2," "P3," and "P4"), the bar on the left represents the ChIP value of samples from LNCaP cells transduced with control shRNA ("sh-Control"), and the bar on the right represents the ChIP value of samples from LNCaP cells transduced with KDM3D shRNA #3 ("sh-KDM3D#3"). In the AR-ChIP bar graphs in FIG. 11B, FIG. 11C, and FIG. 11D, for each probe ("P1," "P2," "P3," and "P4"), the two bars on the left represents the ChIP value of samples from LNCaP cells transduced with control shRNA ("sh-Control") cultured in the absence ("−") or presence ("+") of DHT, and the two bars on the right represents the ChIP value of samples from LNCaP cells transduced with KDM3D shRNA #3 ("sh-KDM3D#3") cultured in the absence ("−") or presence ("+") of DHT.
Figure 11B:
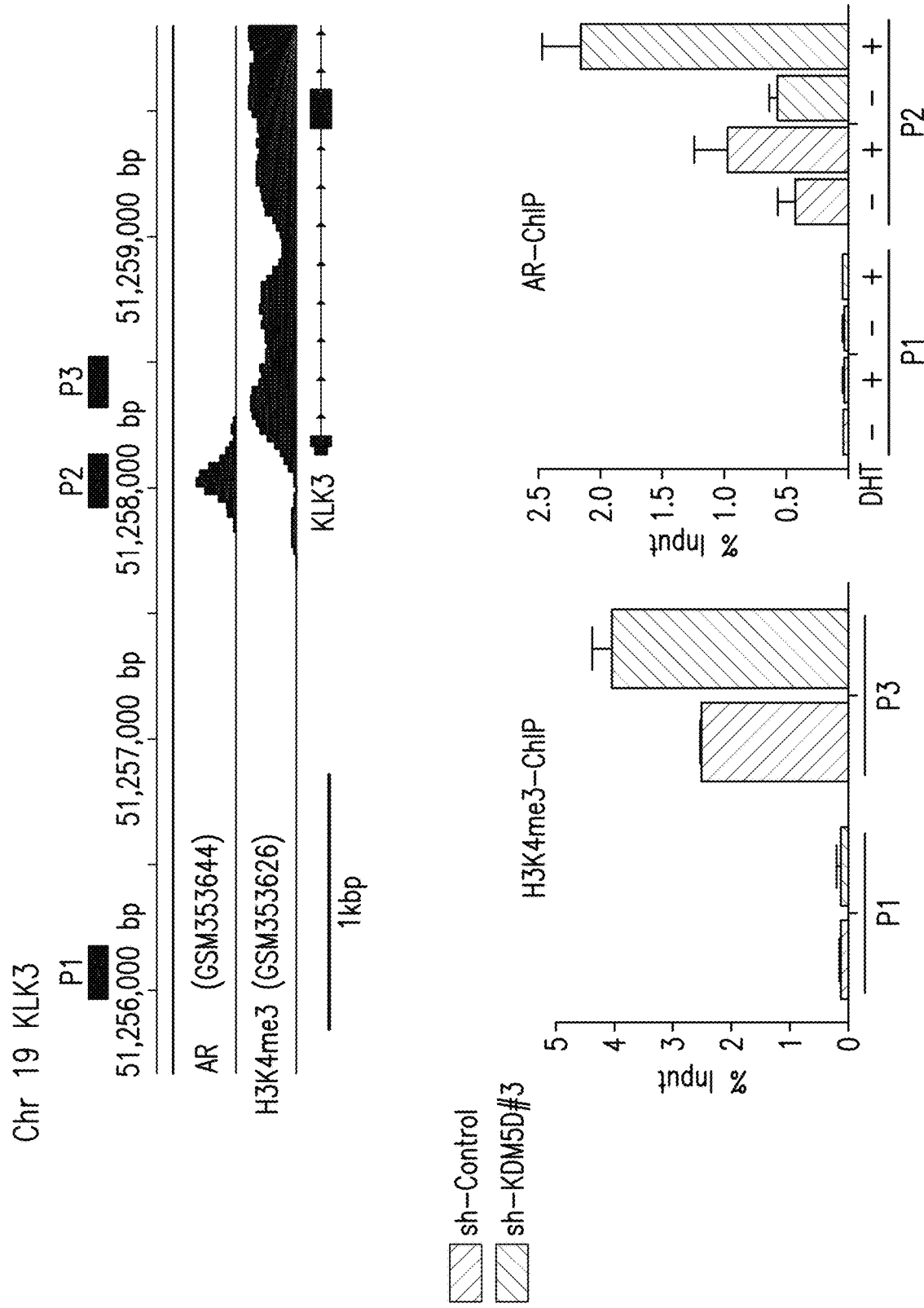
Figure 11C:
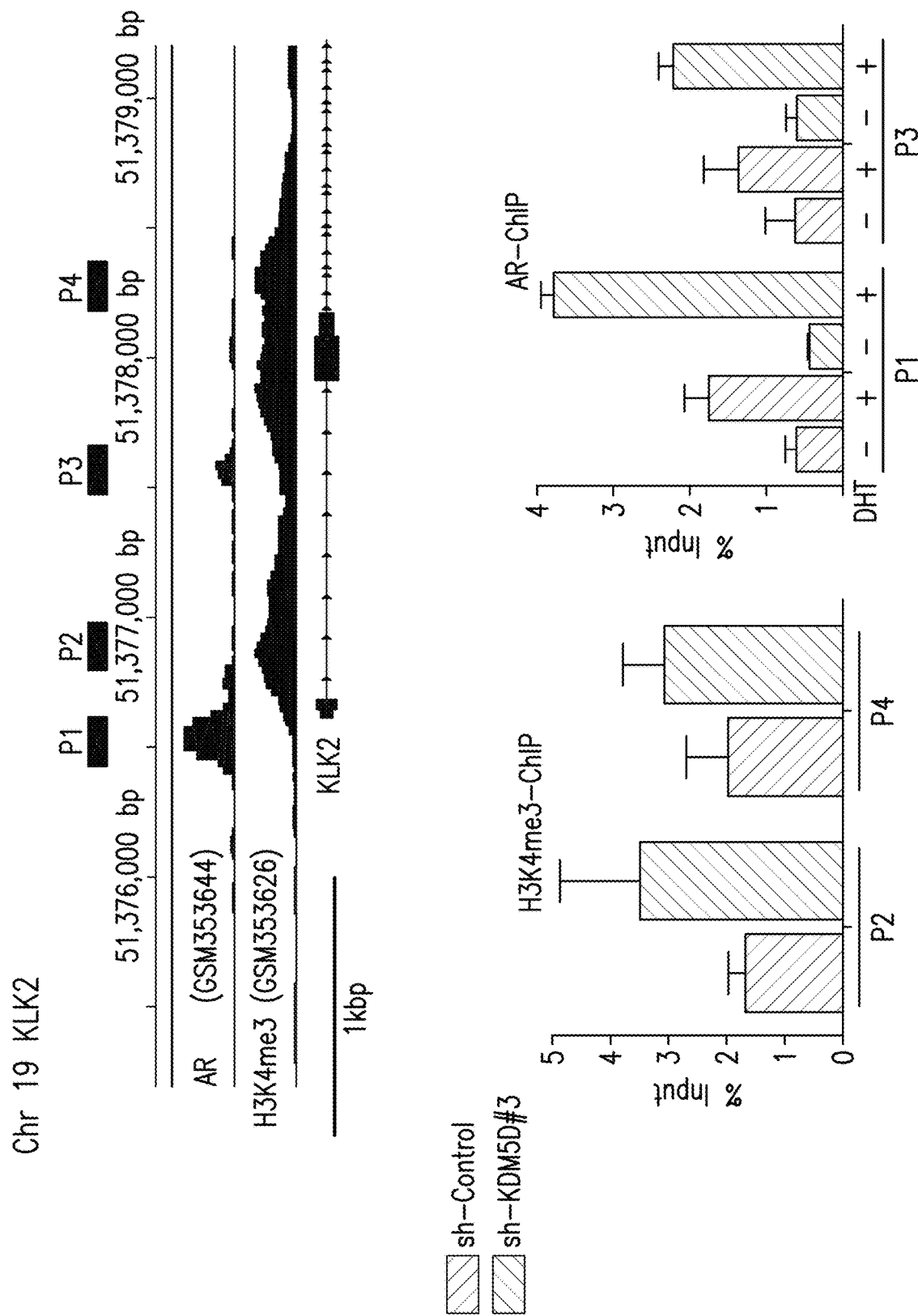
Figure 11D:
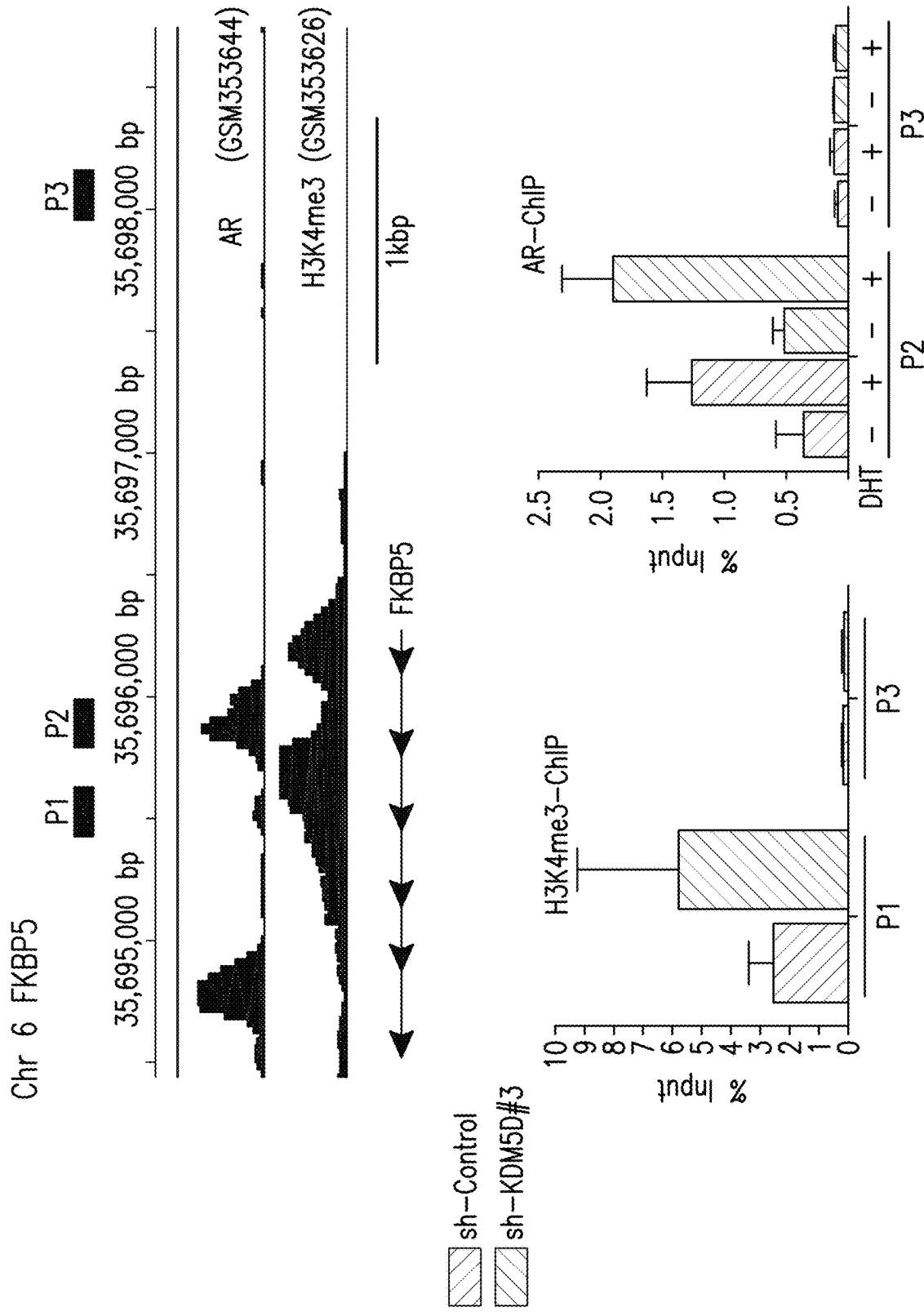
Figure 11F:
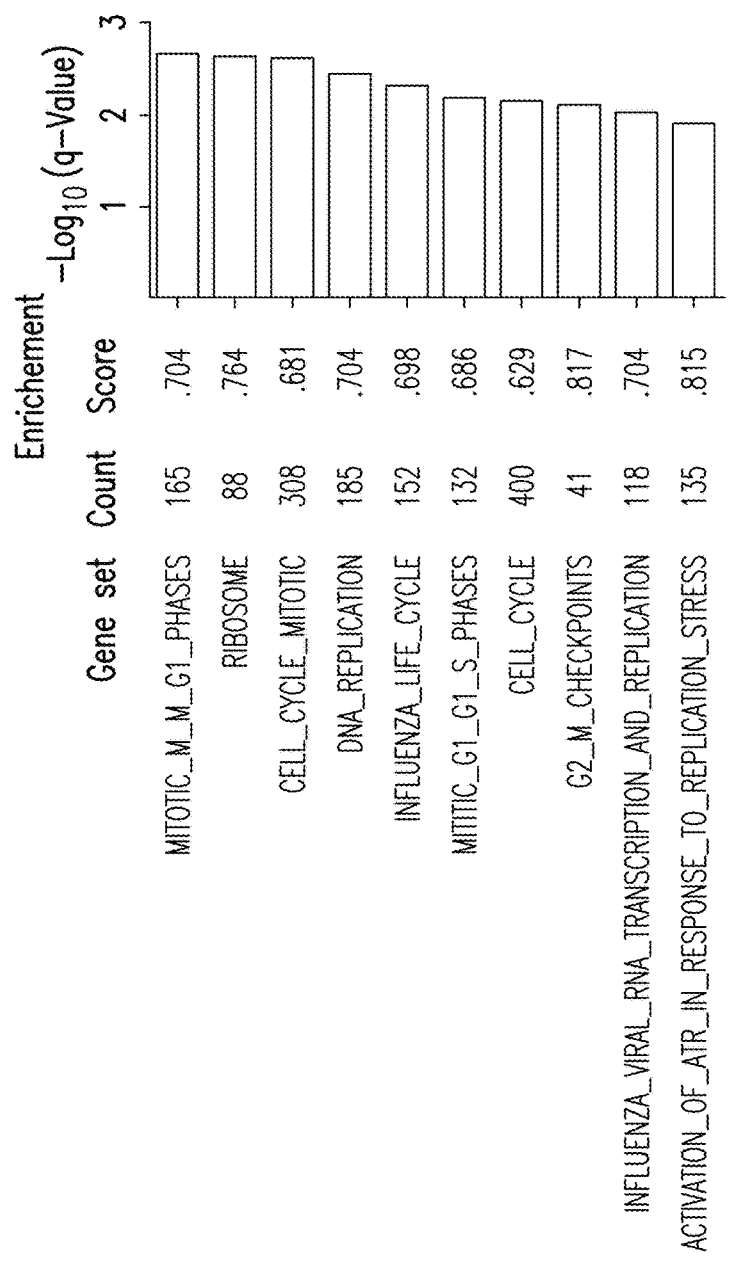
Figure 11E:
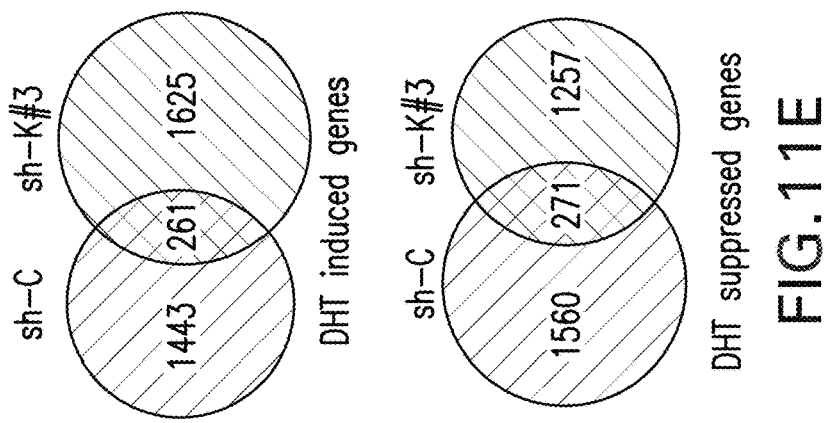

To further demonstrate that KDM5D modulates docetaxel sensitivity with AR activity in the nucleus, the PC3 cell line, which is AR-negative and have deletion of the KDM5D region on the Y chromosome, was used. Full-length AR (AR-FL) and a truncated splice isoform AR-v7 were introduced into PC3 cells. As shown in FIG. 9, expression of AR-FL in KDM5D-negative PC3 cells resulted in greater docetaxel resistance with DHT stimulation but not without DHT stimulation, whereas expression of AR-v7, a constitutively active AR, conferred docetaxel resistance regardless of DHT stimulation. Notably, ectopic expression of KDM5D in PC3 cells restored docetaxel sensitivity even in the presence of AR-FL or AR-v7 expression (FIG. 9), suggesting that KDM5D antagonized factors downstream of AR in the AR signaling pathway.

Example 5

KDM5D Interacts with Nuclear AR

To examine whether KDM5D interacts with AR or AR-associated machinery, coimmunoprecipitation (co-IP) of nuclear protein was conducted using a KDM5D-Flag-tagged LAPC4 cell line. Direct interaction between ectopically expressed KDM5D and AR in the nucleus was observed (FIG. 10, part A). Furthermore, endogenous interaction between KDM5D and AR was detected in LNCaP (FIG. 10, part B). This result suggested a physical interaction between KDM5D and AR in the nucleus.

Example 6

KDM5D Regulates AR Transcriptional Activity

While we do not wish to be bound by theory, this example provides an explanation of how KDM5D regulates AR-dependent docetaxel resistance. Quantitative PCR (QT-PCR) was used to assess the expression levels of several known androgen-regulated genes in LNCaP cells with and without KDM5D knockdown (FIG. 11, part A). KDM5D expression impacted androgen-responsive genes with DHT stimulation, demonstrating a relationship between KDM5D and AR signaling. Because KDM5D has been shown to be capable of demethylating H3K4me3 and me2 marks, the effect of KDM5D knockdown on the levels H3K4 trimethylation and AR binding in the promoter regions of AR-regulated genes was examined. As shown in FIG. 11, parts B-D, H3K4me3 levels in the promoter regions of AR-regulated genes KLK3, KLK2, and FKBPS were increased by knockdown of KDM5D, and AR binding to those promoter regions was more prominent with DHT stimulation, suggesting that knockdown of KDM5D increased H3K4me3 marks, which were recognized as active transcription marks enhancing AR transcriptional activity. RNA-seq analysis showed that knockdown of KDM5D in LNCaP cells led to altered expression of a number of AR-regulated genes (FIG. 11, part E), suggesting a role of KDM5D in modulating the AR transcriptome. A gene set enrichment analysis (GSEA) was performed and the mitosis/cell cycle-related pathways were the most significantly up-regulated gene sets (FIG. 11, part F).

Example 7

Figure 12:
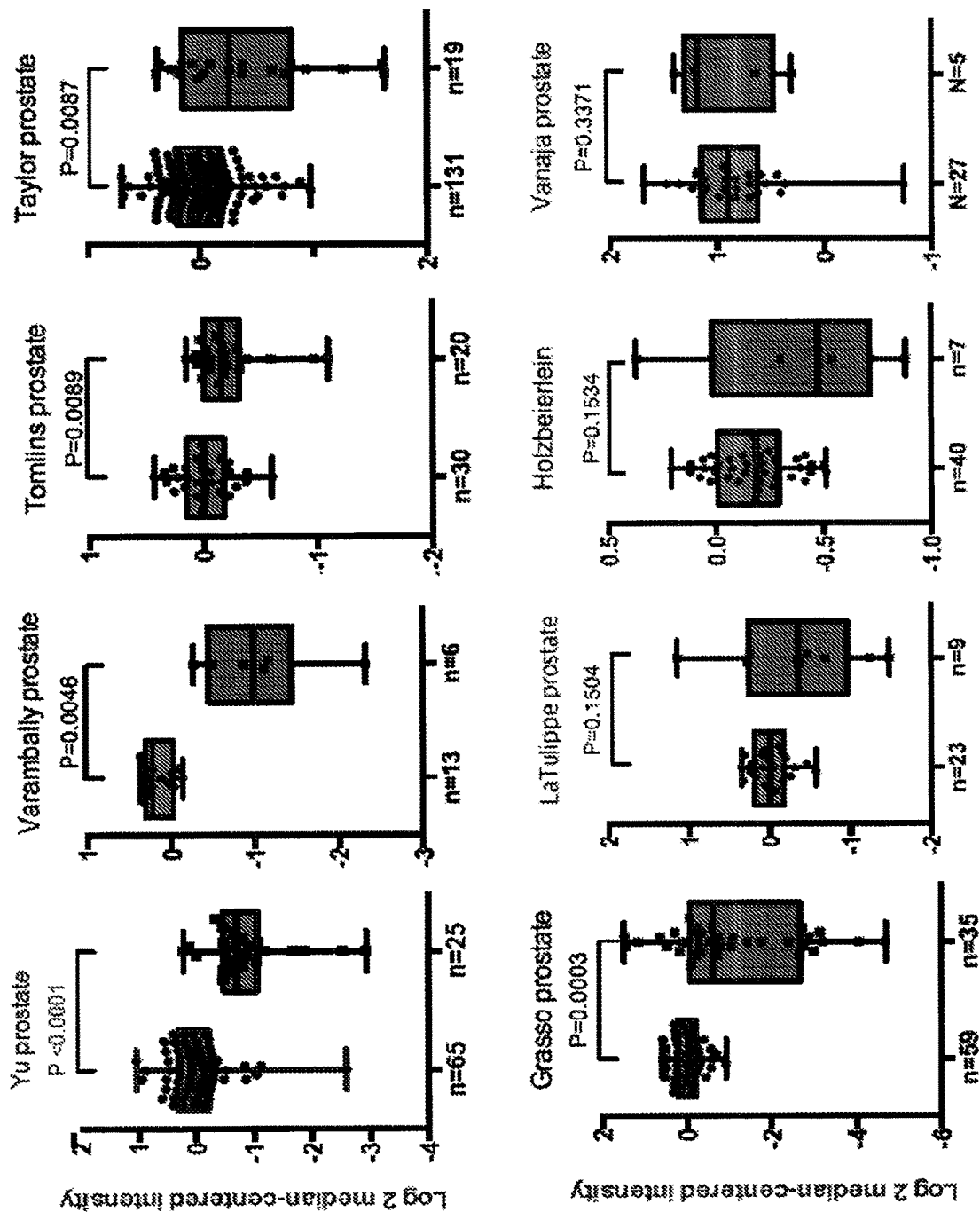
FIG. 12 is a set of graphs showing significantly lower KDM5D expression levels in metastatic sites compared to normal prostate and primary tumors. For each dataset, the bar on the left represents the KDM5D expression level in primary prostate cancer, and the bar on the right represents the KDM5D expression level in castration-resistant prostate cancer (CRPC).

Low Expression Level of KDM5D is Associated with Prostate Cancer Metastasis and Poor Clinical Prognosis To assess the clinical relevance of KDM5D expression in prostate cancer, publicly available datasets in Oncomine were examined. Eight cohorts included mRNA expression levels of KDM5D in normal prostate, primary and metastatic prostate carcinoma. This allowed an assessment of the clinical significance of KDM5D (Table 1). Seven of the eight datasets showed decreased expression levels of KDM5D in CRPC compared with hormone-naive primary cancer, among which the decrease was significantly in five datasets. Two of the remaining three cohorts with smaller sample sizes also showed a similar trend of KDM5D expression level (FIG. 12).

TABLE 1

KDM5D expression in metastatic versus primary prostate cancer in public datasets

| Dataset/Cohort | Gene Expression Omnibus | Log2FC* | P value** |
|---|---|---|---|
| Grasso cohort | GSE35988 | −1.036 | 0.0003 |
| LaTulippe cohort | GSE68882 | −0.3005 | 0.1504 |
| Yu cohort | GSE6919 | −0.85297 | <0.0001 |
| Tomlins cohort | GSE6099 | −0.20936 | 0.0089 |
| Taylor cohort | GSE21034 | −0.38625 | 0.0087 |
| Varambally cohort | GSE3325 | −1.18607 | 0.0046 |
| Vanaja cohort | available in Oncomine | 0.09836 | 0.3371 |
| Holzbeierlein cohort | available in Oncomine | −0.18439 | 0.1534 |

*Fold change was calculated by dividing the average value of KDM5D for metastatic prostate cancer by the average value for primary prostate cancer, and logarithm of the fold change to the base 2 was provided.
**P values were calculated by one-tailed unpaired t test with Welch's correction between metastatic PCa and primary PCa.

One of the eight cohorts, the Grasso cohort, extensively investigated copy-number alteration (CNA) in primary cancer (11 patients) and CRPC (48 patients). Thirteen of 48 CRPC patients (27.1%) had KDM5D deletion, whereas no patients with primary tumors had KDM5D deletion (Table 2). Patients with decreased expression of KDM5D in their CRPC tumors had significantly shorter OS from time of diagnosis or first hormone therapy (FIG. 13, parts A and B). In this small cohort of 31 patients, there was a trend toward shorter survival from time of chemotherapy initiation with lower KDM5D expression (FIG. 13, part C).

Notably, of the 31 CRPC patients with gene expression profiling, a significant correlation between KDM5D mRNA expression level and CNA was found after determining the exon coverage ratio, indicating that less KDM5D expression in CRPC tumors is likely attributable to genetic alteration than epigenetic silencing or posttranslational modification (FIG. 13, part D). No significant correlation between AR and KDM5D expression levels was seen in the Taylor, Crasso, and Robinson cohorts, suggesting that aberrations of AR and attenuated KDM5D expression in CRPC were independent events.

TABLE 2

Baseline characteristics of the patients in the Grasso cohort
Baseline Characteristics of the Patients

| Characteristics | Low KDM5D n = 16 | High KDM5D n = 15 |
|---|---|---|
| Age-y | | |
| Median | 66.5 | 73 |
| Range | 53-78 | 58-85 |
| Median Mutation Count | 59 | 40 |
| Serum PSA Level-ng/ml | | |
| Median | 458 | 324 |
| Range | 12-7336 | 11-8083 |
| Prior Treatment for Prostate cancer-no. (%) | | |
| No local therapy | 8 (50.0) | 3 (20.0) |
| Prostatectomy (n) | 3 (18.7) | 5 (33.3) |
| Radiation (n) | 8 (50.0) | 11 (73.3) |

While lower KDM5D expression indicated poorer prognosis with ADT alone, our results suggested that KDM5D-low cells were sensitive to docetaxel in DHT-free conditions. As illustrated in FIG. 1, androgen is required for maintaining the KDM5D-low LAPC4-like AR transcriptome that contributed to docetaxel resistance. Therefore, a combination therapy of ADT and docetaxel may improve the clinical outcome.

Example 8

Materials and Methods

Cell Culture:
The prostate cancer cell lines LNCaP (ATCC® CRL-1740™), 22RV1 (ATCC® CRL-2505™), VCAP (ATCC® CRL-2876™), PC3 (ATCC® CRL-1435™), DU-145 (ATCC® HTB-81™) were obtained from the American Type Culture Collection (ATCC). LNCaP-Abl cell line was provided by Zoran Culig (Innsbruck Medical University). LNCaP-C42 cell line was obtained from ViroMed Laboratories (Minneapolis). LNCaP-104R2 cell line was provided by Shutsung Liao (University of Chicago), and LAPC-4 cell line was provided by Charles Sawyers (Memorial Sloan Kettering Cancer Center). These cells were maintained with 10% fetal bovine serum (FBS) (LNCaP, LNCaP-C42, LMCaP-AI, VCAP, 22RV1, LAPC4, PC3, and DU145) or 10% charcoal-stripped serum (CSS) (LNCaP-Abl, and LNCaP-104R2) at 37 c in 5% CO2.

Quantitative RT-PCR, DNA Extraction, and RNA-Seq Library Preparation:
RNA was isolated using TRIzol (Invitrogen) according to the manufacturer's protocol followed by quantification using Nanodrop spectrophotometer, and 1 ug of RNA was Reverse-transcribed using High Capacity cDNA Reverse Transcription Kit (Applied Biosystems). DNA was isolated using QIAamp DNA Mini Kit (Qiagen). Quantitative PCR was performed in an ABI 7300 sequence detector. Product formation was detected by incorporation of SYBR green I using ROX as a passive reference. The expression data were normalized with GAPDH in each sample. Experiments were repeated and analyzed three times. For RNA-seq, polyA+ RNA were purified using the polyA spin mRNA isolation kit (NEB) followed by library preparation for 40 ng of purified RNA. RNA fragmentation, first and second strand cDNA synthesis, end repair processing were performed using NEB-Next ultra RNA library prep kit for Illumina (NEB). Adaptor was ligated to the fragments for multiplex samples using NEBNext multiplex oligos for Illumina index primers (NEB) and the libraries were amplified by 14 cycles of PCR. The products were size-fractionated by running on 8% polyacrylamide gel, and final libraries were purified from the gel. Fragment sizes were validate by using the High Sensitivity DNA kit (Agilent Technologies) on an Agilent 2100 Bioanalyzer. Biological triplicate were sequenced by Illumina Nextseq 500 (SR75) at the Dana Farber Cancer Institute Center for Cancer Computational Biology Core Facility.

RNA Interference and Lentiviral Transduction:

MGC Human KDM5D Sequence-xVerified cDNA (BC144102) was purchased from Dharmacon. Individual shRNAs were designed using Enhanced Direct® for licensees considering mismatch potential >0.3 and longest common factor (LCF)<9. Control siRNA (siControl) and siRNAs targeting interested genes (ON TARGET Plus™ siRNA) were purchased from Dharmacon (Catalog numbers are listed in supplementary table). SiRNA transfections were performed using Lipofectamine RNAImax (Invitrogen). Twenty-four hours before transfection, cells are seeded to six well plates. The cells are transfected with 50 nM siRNA as described in the manufacturer's protocol and maintained for 48 hrs followed by the designed experiments. For lentiviral transduction, pLKO-Teton-puro and pLenti-CMyc-DDK-IRES-Puro were transfected with psPAX2 packaging and pMD2. G envelope plasmid to HEK293FT cells using Lipofectamine 3000 (Invitrogen) for 2 days. Then cells were infected with viral supernatants (filtered through a 0.45 .mu.m filter) in the presence of 8 ug/ml polybrene. For sh-RNAs, Spin-infection protocol was applied using 6 well plates at 2700 rpm for 60 min, followed by incubation at 37 c. The next day, medium was changed to fresh medium, and the cells transduced with virus were incubated for 3 days, followed by selection using puromycin (1-1.5 ng/ml).

Immunoblotting, Cell Fractionation, and Co-Immunoprecipitation:

Whole cell lysates were collected and lysed in radio immunoprecipitation assay (RIPA) lysis buffer with proteinase inhibitor cocktail (Thermo Scientific), and sonicated using BioruptorStandard® for 5 min. For cellular protein fractionation, hypotonic lysis buffer [50 mM Hepes-Naoh pH 7.5, 10% Glycerol, 0.5% NP40, 0.25% TritonX-100, proteinase inhibitor cocktail (Thermo Scientific, Waltham, Mass.)] were used for extracting cytoplasmic proteins. Nuclei pellets were washed by cold PBS once and dissolved in high salt nuclear extraction buffer [0.1% SDS, 10 mM Tris-HCl, 150 mM NaCl, 0.1% Triton-X, proteinase inhibitor cocktail (Thermo Scientific)] and sonicated using BioruptorStandard® for 5 min followed by gentle agitation for 30 min at 4 c. After centrifugation at 13200 rpm for 5 min, supernatant were collected as nuclear fractions. Proteins were subjected on 4-15% SDS-polyacrylamide gels before being transferred onto nitrocellulose or polyvinylidene difluoride membrane (Millipore). For co-immunoprecipitation, nuclear pellet of 8*10 6 cells were lysed in nuclear lysis buffer [10 mM Hepes-NaOH pH 8, 1.5 mM MgCl2, 25% Glycerol, 0.5% NP-40, 0.42 M NaCl, 0.2 mM EDTA, 0.5 mM DTT], followed by disruption using U-100 inslin syringe 26 G (Becton Dickinson). After centrifugation (13200 rpm) for 10 min, nuclear fraction was diluted using dilution buffer (20 mM Tris-HCl pH 8.0, 1.5 mM MgCl2, 0.2 mM EDTA, 0.5% NP-40), and MgCl and DNase (NEB) were added for final concentration of 3 mM for Mg2+ and 20 U/ml for DNase, followed by 37 c incubation for 30 min. Dynabeads Protein G (Life Technologies) (30 ul) was used to pre-clear for 60 min at 4 c with gentle rotation. Then, ten percent of lysate was taken as input, and the rest was incubated with 5 ug of primary antibodies (KDM5D: NB100-93292 (0.2 ug/ul), AR: SC-816X (2 ug/ul), Flag: TA50011-100 (1:200), Rabbit-IgG: SC-2027 (0.4 ug/ul), Mouse-igG: SC-2025 (0.4 ug/ul)) overnight. The next day, 50 ul of Dynabeads Protein G was added and incubated for 2 hours at 4 c with gentle rotation.

Precipitated protein were washed using Low Salt Co-IP Wash Buffer (20 mM Tris-HCl pH 8.0, 150 mM NaCl, 1.5 mM MgCl2, 0.5% NP-40, 0.2 mM EDTA) twice, and 30 ul of NuPAGE LDS SAMPLE Buffer with DTT (Boston BioRads) was added and heated at 95 c for 5 min. Supernatants were immunoblotted for the indicated proteins.

Bioinformatics Analysis: The whole genome heat map of differential AR stimulation of LNCaP and LAPC4 was created by using Gene-E, software from the Broad Institute (www.broadinstitute.org/cancer/software/GENE-E/). GO term analysis were employed to examine the impact of AR stimulation of LNCaP and LAPC4 (DAVID bioinformatics resources). A volcano plot was used to effectively identify seven candidate genes among 236 histone modification genes, which demonstrated the significance (Bonferroni Corrected P-values from t-tests) and magnitude (Two Fold Changes) of the gene expression difference between LNCaP and LAPC4.

Sequence Listing

SEQ ID NO: 1—human KDM5D genomic sequence
SEQ ID NO: 2—human KDM5D mRNA sequence, transcript variant 1
SEQ ID NO: 3—human KDM5D mRNA sequence, transcript variant 2
SEQ ID NO: 4—human KDM5D mRNA sequence, transcript variant 3
SEQ ID NO: 5—a primer for amplifying a human KDM5D DNA fragment CGCAGCTTTGAAGAGCTAAG
SEQ ID NO: 6—a primer for amplifying a human KDM5D DNA fragment CAGCTGTGGAGTGTCCATCC
SEQ ID NO: 7—human KDM5D protein sequence, isoform 1
SEQ ID NO: 8—human KDM5D protein sequence, isoform 2
SEQ ID NO: 9—human KDM5D protein sequence, isoform 3

The invention claimed is:

1. A method of treating prostate cancer in a subject in need thereof, comprising:
   (a) comparing a protein expression level of KDM5D in a sample from the subject to a protein expression level of KDM5D in a control sample, and
   (b) when the protein expression level of KDM5D in the sample from the subject is the same as or higher than the protein expression level of KDM5D in the control sample, then administering a taxane without androgen deprivation therapy (ADT) to the subject or administering ADT without a taxane,
   and when the protein expression level of KDM5D in the sample from the subject is lower than the protein expression level in the control sample, administering taxane and an ADT to the subject.

2. The method of claim 1, wherein the control sample is a normal prostate tissue or a primary prostate tumor.

3. The method of claim 1, wherein the control sample is LNCaP cells.

4. The method of claim 1, wherein the prostate cancer is a hormone-naive prostate cancer, hormone-sensitive prostate cancer, castration-resistant prostate cancer, hormone-refractory prostate cancer, or metastatic prostate cancer.

5. The method of claim 1, wherein the sample from the subject is from a cancerous lesion or circulating tumor cells.

6. The method of claim 1, wherein the treatment results in an improvement in one or more of the prostate cancer subject's symptoms selected from the group consisting of: difficulty in urinating, blood in urine, erectile dysfunction, pain in the hips, pain in the back, pain the chest, weakness, numbness, and incontinence.

7. A method of measuring expression of KDM5D in a subject having prostate cancer, the method comprising:
  measuring the binding of an antibody in a sample from the subject, wherein the antibody specifically binds to KDM5D, thereby measuring expression of KDM5D in the subject, and
  administering to the subject a therapeutically effective amount of a taxane without ADT or ADT without a taxane if the expression of KDM5D is the same as or higher than a reference expression level of KDM5D in a control sample; or
  administering to the subject a therapeutically effective amount of a taxane and an ADT if the expression of KDM5D is lower than the reference expression level of KDM5D in a control sample.

8. The method of claim 7, wherein the prostate cancer is a hormone-naive prostate cancer, hormone-sensitive prostate cancer, castration-resistant prostate cancer, or hormone-refractory prostate cancer.

9. The method of claim 7, wherein:
  (a) the prostate cancer is metastatic;
  (b) the subject is a human;
  (c) the sample is from a cancerous lesion, or
  (d) the sample comprises circulating tumor cells.

10. The method of claim 7, wherein the ADT is selected from the group consisting of flutamide, nilutamide, enzalutamide, bicalutamide, ketonazole, abiraterone, abiraterone acetate, orteronel, finasteride, dutasteride, bexlosteride, izonsteride, turosteride, episteride, dexamethasone, prednisone, leuprolide, goserelin, triptorelin, histrelin and estrogen.

11. The method of claim 7, wherein the taxane is selected from the group consisting of paclitaxel, docetaxel, protaxel, larotaxel, cabazitaxel, Abraxane, Ortataxel, Genexol, DJ-927 and BMS-184476.

12. The method of claim 7, wherein the control sample is a normal prostate tissue or a primary prostate tumor.

13. The method of claim 7, wherein the control sample is LNCaP cells.

14. The method of claim 1, wherein the treatment results in a decrease in cancer load.

15. The method of claim 1, wherein the subject is a human.

16. The method of claim 1, wherein the taxane is docetaxel.

17. The method of claim 16, wherein the docetaxel is administered at a dose of 10 to 70 $mg/m^2$.

18. The method of claim 7, wherein the taxane is docetaxel.

19. The method of claim 18, wherein the docetaxel is administered at a dose of 10 to 70 $mg/m^2$.

* * * * *